(12) United States Patent
Encell et al.

(10) Patent No.: US 11,293,047 B2
(45) Date of Patent: Apr. 5, 2022

(54) LUCIFERASE SEQUENCES UTILIZING INFRARED-EMITTING SUBSTRATES TO PRODUCE ENHANCED LUMINESCENCE

(71) Applicant: PROMEGA CORPORATION, Madison, WI (US)

(72) Inventors: Lance P. Encell, Fitchburg, WI (US); Mary P. Hall, Waunakee, WI (US); Keith V. Wood, Madison, WI (US); Monika G. Wood, Madison, WI (US)

(73) Assignee: Promega Corporation, Madison, WI (US)

( * ) Notice: Subject to any disclaimer, the term of this patent is extended or adjusted under 35 U.S.C. 154(b) by 0 days.

(21) Appl. No.: 16/725,586

(22) Filed: Dec. 23, 2019

(65) Prior Publication Data

US 2020/0115735 A1    Apr. 16, 2020

Related U.S. Application Data

(63) Continuation of application No. 15/644,876, filed on Jul. 10, 2017, now Pat. No. 10,550,420, which is a continuation of application No. 14/851,608, filed on Sep. 11, 2015, now Pat. No. 9,732,373.

(60) Provisional application No. 62/049,150, filed on Sep. 11, 2014.

(51) Int. Cl.
| | |
|---|---|
| *C12Q 1/66* | (2006.01) |
| *G01N 33/542* | (2006.01) |
| *C12N 9/02* | (2006.01) |
| *G01N 21/64* | (2006.01) |
| *G01N 33/68* | (2006.01) |

(52) U.S. Cl.
CPC ............. *C12Q 1/66* (2013.01); *C12N 9/0069* (2013.01); *G01N 21/6428* (2013.01); *G01N 33/542* (2013.01); *G01N 33/6803* (2013.01); *C12Y 113/12007* (2013.01); *G01N 2021/6432* (2013.01); *G01N 2021/6439* (2013.01); *G01N 2333/90241* (2013.01)

(58) Field of Classification Search
CPC ........... C12N 9/02; C12Q 1/66; G01N 21/763
See application file for complete search history.

(56) References Cited

U.S. PATENT DOCUMENTS

| | | |
|---|---|---|
| 5,049,358 A | 9/1991 | Lau |
| 5,196,524 A | 3/1993 | Gustafson et al. |
| 5,219,737 A | 6/1993 | Kajiyama et al. |
| 5,229,285 A | 7/1993 | Kajiyama et al. |
| 5,480,789 A | 1/1996 | Firoozabady et al. |
| 5,605,793 A | 2/1997 | Stemmer |
| 5,670,356 A | 9/1997 | Sherf et al. |
| 5,674,713 A | 10/1997 | McElroy et al. |
| 5,700,673 A | 12/1997 | McElroy et al. |
| 5,716,851 A | 2/1998 | Pugia et al. |
| 6,074,859 A | 6/2000 | Hirokawa et al. |
| 6,132,983 A | 10/2000 | Lowe et al. |
| 6,171,808 B1 | 1/2001 | Squirrell et al. |
| 6,265,177 B1 | 7/2001 | Squirrell et al. |
| 6,387,675 B1 | 5/2002 | Wood et al. |
| 6,602,677 B1 | 8/2003 | Wood et al. |
| 7,183,092 B2 | 2/2007 | Choi et al. |
| 7,241,584 B2 | 7/2007 | Wood et al. |
| 7,452,663 B2 | 11/2008 | Wood et al. |
| 7,537,912 B2 * | 5/2009 | Wood .................... C07D 487/04 435/19 |
| 7,728,118 B2 | 6/2010 | Wood et al. |
| 7,732,128 B2 | 6/2010 | Wood et al. |
| 7,879,540 B1 | 2/2011 | Wood et al. |
| 7,906,298 B1 | 3/2011 | Squirrell et al. |
| 8,030,017 B2 | 10/2011 | Wood et al. |
| 8,288,559 B2 * | 10/2012 | Corona ................ C07D 417/14 548/178 |
| 8,557,970 B2 | 10/2013 | Encell et al. |
| 8,652,794 B2 | 2/2014 | Squirrell et al. |
| 8,669,087 B1 | 3/2014 | Squirrell et al. |
| 8,669,103 B2 | 3/2014 | Binkowski et al. |
| 8,822,170 B2 | 9/2014 | Wood et al. |
| 9,447,450 B2 | 9/2016 | Hitko |
| 2003/0068801 A1 | 4/2003 | Wood et al. |
| 2003/0232404 A1 | 12/2003 | Wood et al. |
| 2005/0048592 A1 | 3/2005 | Wood et al. |
| 2006/0183212 A1 | 8/2006 | Wood et al. |
| 2007/0015790 A1 * | 1/2007 | Cali ........................ C09B 57/02 514/314 |
| 2008/0070299 A1 | 3/2008 | Wood et al. |
| 2008/0090291 A1 | 4/2008 | Wood et al. |
| 2008/0206798 A1 | 8/2008 | Wood et al. |
| 2009/0137019 A1 | 5/2009 | Wood et al. |
| 2009/0311769 A1 | 5/2009 | Riley et al. |
| 2011/0177540 A1 | 7/2011 | Squirrell et al. |
| 2012/0009647 A1 | 1/2012 | Wood et al. |
| 2014/0170686 A1 | 6/2014 | Squirrell et al. |
| 2014/0170687 A1 | 6/2014 | Squirrell et al. |
| 2014/0186918 A1 | 7/2014 | Squirrell et al. |
| 2014/0223590 A1 | 8/2014 | Binkowski et al. |
| 2014/0227759 A1 | 8/2014 | Binkowski et al. |
| 2016/0076079 A1 | 3/2016 | Encell et al. |

FOREIGN PATENT DOCUMENTS

| | | |
|---|---|---|
| EP | 0337349 | 10/1989 |
| EP | 0449621 | 10/1991 |

(Continued)

OTHER PUBLICATIONS

EPO Office Action for Application No. 15767679.2 dated May 12, 2020 (4 pages).

(Continued)

*Primary Examiner* — Karen Cochrane Carlson
(74) *Attorney, Agent, or Firm* — Casimir Jones, S.C.; Peter J. Schlueter

(57) ABSTRACT

Provided herein are isolated polynucleotide encoding modified click beetle luciferase polypeptides that have enhanced luminescence and longer wavelength near-infrared signals. The disclosure also relates to near-infrared bioluminescence systems that include said modified click beetle luciferase polypeptides and novel luciferin derivatives, as well as methods of using said modified click beetle luciferase polypeptides and bioluminescence systems.

7 Claims, 23 Drawing Sheets

Specification includes a Sequence Listing.

(56) References Cited

FOREIGN PATENT DOCUMENTS

| | | |
|---|---|---|
| EP | 0524448 | 1/1993 |
| EP | 0680515 | 8/1998 |
| EP | 2 272 972 * | 1/2011 |
| EP | 2366778 | 8/2012 |
| GB | 2301592 | 12/1996 |
| JP | 5-244942 | 9/1993 |
| JP | 8-510387 | 11/1996 |
| JP | 9510610 | 10/1997 |
| JP | 9-294600 | 11/1997 |
| JP | 2012-161325 | 8/2012 |
| WO | WO 95/18853 | 7/1995 |
| WO | WO 95/25798 | 9/1995 |
| WO | WO 96/02665 | 2/1996 |
| WO | WO 96/22376 | 7/1996 |
| WO | WO 98/013487 | 4/1998 |
| WO | WO 98/46729 | 10/1998 |
| WO | WO 99/14336 | 3/1999 |
| WO | WO 00/24878 | 5/2000 |
| WO | WO 01/20002 | 3/2001 |
| WO | WO 01/31028 | 5/2001 |
| WO | WO 02/16944 | 2/2002 |
| WO | WO 2005/038029 | 4/2005 |
| WO | WO 2007/120522 | 10/2007 |
| WO | WO 2009/140662 | 11/2009 |
| WO | WO 2014/159044 | 10/2014 |

OTHER PUBLICATIONS

Stolz et al., "Darwinian natural selection for orange bioluminescent color in a Jamaican click beetle," with sequence alignments attached (2003) PNAS 100:25 14955-14959.
GB 2345913 9823468.5, The Secretary of State for Defence, Jul. 26, 2000.
Alberts, B. et al., Molecular Biology of The Cell, Third Edition, Garland Publishing, Inc. (1994) 56-57.
Arkin, A.P. et al., "Optimizing nucleotide mixtures to encode specific subsets of amino acids for semi-random mutagenesis," BioTechnology (1992) 10:297-300.
Arnold, F.H., "Directed evolution: creating biocatalysts for the future," Chem. Eng. Sci. (1996) 51:5091-5102.
Arslan, T. et al., "Structurally modified firefly luciferase. Effects of amino acid substitution at position 286," J. Amer. Chem. Soc. (1997) 119(45):10877-10887.
Barnes, W.M., "Variable patterns of expression of luciferase in transgenic tobacco leaves," Proc. Natl. Acad. Sci. USA (1990) 87:9183-9187.
Bowie et al., "Deciphering the message in protein sequences tolerance to amino acid substitutions," Science (1990) 247:1306-1310.
Branchini et al., "Red- and green-emitting firefly luciferase mutants for bioluminescent reporter applications," Analytical Biochemistry 345 (2005) 140-148.
Branchini et al., "Red-emitting luciferase for bioluminescent reporter and imaging applications," Analytical Biochemistry 396 (2010) 290-297.
Branden, C. et al., "Introduction to protein structure," Garland Publishing Inc., New York (1991) 247.
Cadwell, R.C. et al., "Randomization of genes by PCR mutagenesis," PCR Methods and Applications (1992) 2:28-33.
Chenna et al., "Multiple sequence alignment with the Clustal series of programs," Nucl. Acids Res. 31(13):3497-3500 (2003).
Climie, S. et al., "Saturation site-directed mutagenesis of thymidylate synthase," J. Biol. Chem. (1990) 265(31):18776-18779.
Conti, E. et al., "Crystal structure of firefly luciferase throws light on a superfamily of adenylate-forming enzymes," Structure (1996) 4(3):287-298.
De Wet, J.R. et al., "Firefly luciferase gene: structure and expression in mammalian cells," Mol. Cell. Biol. (1987) 7(2):725-737.

Dementieva, E.I. et al., "Assay of ATP in intact Escherichia coli cells expressing recombinant firefly luciferase," Biochem. (1996) 61(7):915-920.
Dementieva, E.I., "Physicochemical properties of recombinant luciolo mingrelica luciferase and its mutant forms," Biochem. (1996) 61(1):115-119.
Devereux, J. et al., "A comprehensive set of sequence analysis programs for the VAX," Nucl. Acids Res. (1984) 12(1):38-395.
Devine, J.H. et al., "Luciferase from the East European firefly Luciola mingrelica: cloning and nucleotide sequence of the cDNA, overexpression in Escherichia coli and purification of the enzyme," Biochimica et Biophysica Acta (1993) 1173:121-132.
Fromant, M. et al., "Direct random mutagenesis of gene-sized DNA fragments using polymerase chain reaction," Anal. Biochem. (1995) 224(1):347-353.
Hanahan, "Techniques for transformation of E. coli," In: DNA Cloning: A Practical Approach, Glover, D.W. editor, IRL Press, Oxford (1985) 1(6):109-135.
Huang, W. et al., "Identification of biologically active mutants by combinatorial cassette mutagenesis: exclusion of wild-type codon from degenerate codons," Anal. Biochem. (1994) 218(2):454-457.
Jagadish et al., "Site-directed mutagenesis of a potyvirus coat protein and its assembly in Escherichia coli," Journal of Genreal Virology, 1993, 74, 893-896.
Janowski, M., "Ras proteins and the Ras-related signal transduction pathway," Radiation & Env. Biophys. (1991) 30(3):185-189.
Kajiyama, N. et al., "Enhancement of thermostability of forefly luciferase from luciola lateralis by a single amino acid substitution," Biosci. Biotech. Biochem. (1994) 58(6):1170-1171.
Kajiyama, N. et al., "Isolation and characterization of mutants of firefly luciferase which produce different colors of light," Protein Eng. (1991) 4(6):691-693.
Kajiyama, N. et al., "Thermostabilization of firefly luciferase by a single amino acid substitutional position 217," Biochem. (1993) 32(50):13795-13799.
Kim-Choi, E. et al., "Creating a mutant luciferase resistant to HPV chemical inhibition by random mutagenesis and colony-level screening," Luminescence (2006) 21:135-142.
Kim-Choi, E. et al., "Kinetic characterization and in vitro toxicity evaluation of a luciferase less susceptible to HPV chemical inhibition," Toxicology in Vitro (2006) 20:1537-1547.
Klock, C.,"Cloning vector pGEM-luc," Promega Corporation, Accession No. X65316 (Apr. 7, 1992) 5 pages.
Kutuzova et al., "Bioluminescence color variation and kinetic behavior relationships among beetle luciferases," Bioluminescence & Chemiluminescence, Molecular Reporting with Photons, J.W. Hastings et al. editors, John Wiley & Sons (1996) 248-252.
Kyte et al., "A Simple Method for Displaying the Hydropathic Character of a Protein," J. Mol. Biol. 157:105-132 (1982).
Langley et al., "Molecular Basis of Beta-Glactosidase Alpha-Complementation," PNAS 72:1254-1257 (1975).
Law, G.H. et al., "Mutagenesis of solvent-exposed amino acids of photinus pyralis luciferase improves thermostability and pH tolerance," Biochem. J. (2006) 397:305-312.
Levit and Berger, "Ribonuclease S-Peptide," J. Biol. Chem. 251:1333-1339 (1976).
Lipman, D. et al., "Rapid and sensitive protein similarity searches," Science (1985) 227:1435-1441.
Liu, Y. et al., "Factors influencing the efficiency of cationic liposome-mediated intravenous gene delivery," Nature Biotech (1997) 15:167-173.
Manukhov et al., "Cloning of the vibrio harveyi luxA and luxB genes and the expression fo bioluminescence in Escherichia coli and bacillus subtillis," Russian Biotech. (1996) 1:1-6.
Murray et al., "Codon usage in plant genes," Nucl. Acids Res., 17:477 (1989).
Needleman and Wunsch, "A General Method Applicable to the Search for Similarities in the Amino Acid Sequence of Two Proteins," (J. Mol. Biol., 48:443-453 (1970).
Nishiguchi et al., "Development of red-shifted mutants derived from luciferase of Brazilian click beetle Pyrearinus termitilluminans," Journal of Biomedical Optics vol. 20(10), 101205-1-101205-7 (Oct. 2015).

(56) References Cited

OTHER PUBLICATIONS

Oba et al., "Characterization of luciferases and its paralogue in the Panamanian luminous click beetle *Pyrophorus angustus*: A click beetle luciferase lacks the fatty acyl-CoA synthetic activity," Gene 452 (2010) 1-6.

Ohmiya, Y. et al., "Cloning, expression and sequence analysis of cDNA for the luciferases from the Japanese fireflies, *Pyrocoelia miyako* and *Hotaria parvula*," Photochem. Photobiol. (1995) 62(2):309-313—Genbank Accession No. Q26076, Oct. 2006 (2 pages).

Pearson and Lipman, "Improved tools for biological sequence comparison," (Proc. Natl. Acad. Sci. USA, 85:2444-2448 (1988).

Prosecution File History of U.S. Appl. No. 10/378,168 (112 pages) this is 9447-01.

Purdy et al., "Heterologous gene expression in *Campylobacter coli*: the use of bacterial luciferase in a promoter probe vector," FEMS Microbiology Letters (1993) 111:233-237.

Qiagen Distributors, "QIAprep® Miniprep Handbook," (Mar. 2002) 1-48.

Querol et al., "Analysis of protein conformational characteristics related to thermostability," Protein Engineering, 1996, vol. 9, No. 3, pp. 265-271.

Raphael et al., "A novel method for multiple alimnment of sequences with repeated and shuffled elements." Genome Res. 14(11):2336-2346 (2004).

Reeck, G.R. et al., "'Homology' in proteins and nucleic acids: a terminology muddle and a way out of it," Cell (1987) 50:667.

Rommens, J.M. et al., "CAMP-inducible chloride conductance in mouse fibroblast lines stably expressing the human cystic fibrosis transmembrane conductance regulator," Proc. Natl. Acad. Sci. USA (1991) 88:7500-7504.

Saiki, R.K. et al., "Primer-directed enzymatic amplification of DNA with a thermostable DNA polymerase," Science (1988) 239:487-491.

Sala-Newby, G.B. et al., "Engineering a bioluminescent indicator for cyclic AMP-dependent protein kinase," Biochem. J. (1991) 279:727-732.

Sala-Newby, G.B. et al., "Engineering firefly luciferase as an indicator of cyclic AMP-dependent protein kinase in living cells," FEBS Lett. (1992) 307(2):241-244.

Sala-Newby, G.B., "Sequence and biochemical similarities between the luciferases of the glow-worm *Lampyris noctiluca* and the firefly *Photinus pyralis*," Biochem. J. (1996) 313:761-767.

Sambrook, J. et al., "Molecular Cloning—A Laboratory Manual," Second Edition (1989) 17.37-17.39.

Sanger, F. et al., "DNA sequencing with chain-terminating inhibitors," Proc. Natl. Acad. Sci. (1977) 74(12):5463-5467.

Smith et al., "Identification of Common Molecular Subsequences," (J. Mol. Biol. 147:195-197 (1981).

Steghens, J. et al., "Firefly luciferase has two nucleotide binding sites: effect of nucleoside monophosphate and CoA on the light-emission spectra," Biochem. J. (1998) 336:109-113.

Stemmer, W.P.C., "DNA shuffling by random fragmentation and reassembly: in vitro recombination for molecular evolution," Proc. Natl. Acad. Sci. USA (1994) 91:10747-10751.

Strause, L.G. et al., "Characteristics of luciferases from a variety of firefly species: evidence for the presence of luciferase isozymes," Insect Biochem. (1981) 11(4):417-422.

Sung, D. et al., "The N-terminal amino acid sequences of the firefly luciferase are important for the stability of the enzyme," Photochem. Photobiol. (1998) 68:749-753.

Szittner et al., "Nucleotide sequence, expression, and properties of luciferase coded by lux genes froma terrestrial bacterium," J. Biol. Chem. (1990) 265(27):16581-16587.

Thompson, J.F. et al., "Modulation of firefly luciferase stability and impact on studies of gene regulation," Gene (1991) 103:171-177.

Thompson, J.F. et al., "Mutation of a protease-sensitive region in firefly luciferase alters light emission properties," J. Biol. Chem. (1997) 272:18766-18771.

Tisi, L.C. et al., "The basis of the bathochromic shift in the luciferase from photinus pyralis," Biolumin. Chemilumin.: Proceedings of the Symposium on Bioluminescence and Chemiluminescence, 12th, Cambridge, United Kingdom (Apr. 5-9, 2002) 57-60.

Tisi, L.C., "Development of a thermostable firefly luciferase," Anal. Chim. Acta (2002) 457:115-123.

Viviani, V. et al., "Cloning, sequence analysis, and expression of active phrixothrix railroad-worms luciferases: relationship between bioluminescence spectra and primary structures," Biochem. (1999) 38:8271-8279.

Wada et al., "Codon usage tabulated from the GenBank genetic sequence data," Nucl. Acids Res., 18:2367-2411 (1990).

Watson, J. et al., Molecular Biology of the Gene, Fourth Edition, The Benjamin/Cummings Publishing Company, vol. 1—General Principles (1987) 43.

White, P.J. et al., "Generation and characterisation of a thermostable mutant of luciferase from photinus pyralis," Proceedings of the 8th International Symposium on Bioluminescence & Chemiluminescence, Sep. 1994, Biolum. Chemilum. (1994) 419-422.

White, P.J. et al., "Improved thermostability of the North American firefly luciferase: saturation mutagenesis at postion 354," Biochem. J. (1996) 319(Pt. 2):343-350.

Willey, T. et al., "Design and selection of firefly luciferases with novel in vivo and in vitro properties," Proceedings of the 11th International Symposium on Bioluminescence and Chemiluminescence (Sep. 6-10, 2000) 201-204.

Witkowski, A. et al., "Conversion of a B-ketoacyl synthase to a malonyl decarboxylase by replacement of the active-site cysteine with glutamine," Biochem. (1999) 38:11643-11650.

Wood, K.V. et al., "Bioluminescent click beetles revisited," J. Biolumin. Chemilumin. (1989) 4:31-39.

Wood, K.V. et al., "Complementary DNA coding click beetle luciferases can elicit bioluminescence of different colors," Science (1989) 244:700-702.

Wood, K.V. et al., "Introduction to beetle luciferases and their applications," J. Biolum. Chemilum. (1989) 4:289-301.

Wood, K.V. et al., "Photographic detection of luminescence in *Escherichia coli* containing the gene for firefly luciferase," Anal. Biochem. (1987) 161:501-507.

Wood, K.V., "Luc genes: introduction of colour into bioluminescence assays," J. Biolumin. Chemilumin. (1990) 5:107-114.

Wood, K.V., "The chemical mechanism and evolutionary development of beetle bioluminescence," Photochem. Photobiol. (1995) 62(4):662-673.

Ye, L., "Cloning and sequencing of a cDNA for firefly luciferase from photuris Pennsylvanica," Biochimica et Biophysica Acta (1997) 1339(1):39-52.

Zenno, S. et al., "Firefly mRNA for luciferase, complete cds, clone pPFL17," Database EMBL GenBank Accession No. D25416 (1997) 2 pages.

Zenno, S. et al., "Firefly mRNA for luciferase, complete cds, clone pPFL19," Database EMBL Accession No. D25415 (1996) 2 pages.

Zhang, J. et al., "Directed evolution of a fucosidase from a galactosidase by DNA shuffling and screening," Proc. Natl. Acad. Sci. (1997) 94(9):4504-4509.

Mitani et al. Sep. 2013; Cloning and characterization of luciferase from Fijian luminous click beetle. Photochemistry and Photobiology, 89(5): 1163-1169.

Cheraghi et al. Apr. 2013; Structural and functional effects of circular permutations of firefly luciferase: In vitro assay of caspase 3/7. International J. Biological Macromolecules 58:336-342.

International Preliminary Examination Report for Application No. PCT/GB96/00099 dated Apr. 10, 1997 (5 pages).

Written Opinion for Application No. PCT/GB96/00099 dated Oct. 24, 1996 (3 pages) excerpts (all that is in file).

International Search Report for Application No. PCT/GB96/00099 dated May 9, 1996 (3 pages).

International Preliminary Examination Report for Application No. PCT/GB98/01026 dated Jun. 29, 1999 (5 pages).

International Search Report for Application No. PCT/GB98/01026 dated Oct. 13, 1998 (4 pages).

Written Opinion for Application No. PCT/GB98/01026 dated Feb. 5, 1999 (6 pages).

(56) References Cited

OTHER PUBLICATIONS

International Preliminary Examination Report for Application No. PCT/GB99/003538 dated Aug. 14, 2000 (4 pages).
International Search Report for Application No. PCT/GB99/003538 dated May 23, 2000 (5 pages).
Invitation to Pay Additional Fees and Partial International Search Report for Application No. PCT/GB99/003538 dated Mar. 20, 2000 (5 pages).
International Preliminary Examination Report for Application No. PCT/GB00/004133 dated May 30, 2002 (11 pages).
Written Opinion for Application No. PCT/GB00/004133 dated Apr. 11, 2002 (10 pages).
International Search Report for Application No. PCT/GB00/004133 dated Aug. 1, 2001 (4 pages).
International Preliminary Examination Report for Application No. PCT/GB1995/000629 dated Jul. 12, 1996 (4 pages).
Written Opinion for Application No. PCT/GB1995/000629 dated Dec. 15, 1995 (3 pages).
International Search Report for Application No. PCT/GB1995/000629 dated Aug. 1, 1995 (3 pages).
International Preliminary Examination Report for Application No. PCT/US98/19494 dated Jan. 11, 2000 (8 pages).
International Search Report for Application No. PCT/US98/19494 dated Apr. 16, 1999 (5 pages).
Written Opinion for Application No. PCT/US98/19494 dated Sep. 14, 1999 (9 pages).
International Search Report for Application No. PCT/US95/00108 dated Apr. 17, 1995 (3 pages).
International Search Report for Application No. PCT/US99/30925 dated Aug. 14, 2000 (10 pages).
Invitation to Pay Additional Fees and Partial Search Report for Application No. PCT/US99/30925 dated Jun. 2, 2000 (12 pages).
Invitation to Pay Additional Fees and Partial Search Report for Application No. PCT/US2015/049661 dated Nov. 9, 2015 (7 pages).
International Search Report and Written Opinion for Application No. PCT/US2015/049661 dated Jan. 8, 2016 (20 pages).
United States Patent Office Action for U.S. Appl. No. 08/875,277 dated Dec. 17, 1999 (8 pages).
United States Patent Office Action and Notice of Allowance for U.S. Appl. No. 08/875,277 dated Jul. 3, 2000 (4 pages).
United States Patent Office Action for U.S. Appl. No. 08/875,277 dated Dec. 7, 1998 (9 pages).
United States Patent Office Action for U.S. Appl. No. 08/875,277 dated Jul. 6, 1998 (10 pages).
United States Patent Office Action/Notice of Allowance for U.S. Appl. No. 09/380,061 dated Mar. 5, 2001 (5 pages).
United States Patent Office Action for U.S. Appl. No. 09/763,824 dated Nov. 9, 2009 (9 pages).
United States Patent Office Action for U.S. Appl. No. 09/763,824 dated Jun. 24, 2008 (15 pages).
United States Patent Office Action for U.S. Appl. No. 09/763,824 dated Nov. 28, 2007 (20 pages).
United States Patent Office Action for U.S. Appl. No. 09/763,824 dated Apr. 3, 2007 (16 pages).
United States Patent Office Action for U.S. Appl. No. 09/763,824 dated May 16, 2006 (14 pages).
United States Patent Office Action for U.S. Appl. No. 09/763,824 dated Sep. 19, 2005 (18 pages).
United States Patent Office Action for U.S. Appl. No. 09/763,824 dated Dec. 15, 2004 (27 pages).
United States Patent Office Action for U.S. Appl. No. 09/763,824 dated Jul. 22, 2010 (9 pages).
United States Patent Office Action for U.S. Appl. No. 09/763,824 dated Sep. 30, 2010 (3 pages).
United States Patent Office Notice of Allowance for U.S. Appl. No. 09/763,824 dated Nov. 8, 2010 (5 pages).
United States Patent Office Action for U.S. Appl. No. 13/023,704 dated Jun. 30, 2011 (4 pages).
United States Patent Office Action for U.S. Appl. No. 13/023,704 dated Jul. 14, 2011 (27 pages).
United States Patent Office Action for U.S. Appl. No. 13/023,704 dated Nov. 9, 2011 (25 pages).
United States Patent Office Action for U.S. Appl. No. 13/023,704 dated May 7, 2013 (15 pages).
United States Patent Office Notice of Allowance for U.S. Appl. No. 13/023,704 dated Sep. 27, 2013 (15 pages).
United States Patent Office Action for U.S. Appl. No. 14/157,959 dated Oct. 9, 2014 (12 pages).
United States Patent Office Action for U.S. Appl. No. 14/157,951 dated Apr. 3, 2015 (18 pages).
United States Patent Office Final Office Action for U.S. Appl. No. 14/157,951 dated Jul. 14, 2015 (20 pages).
United States Patent Office Action for U.S. Appl. No. 14/157,959 dated Apr. 23, 2015 (18 pages).
United States Patent Office Action for U.S. Appl. No. 10/111,723 dated Feb. 22, 2010 (15 pages).
United States Patent Office Action for U.S. Appl. No. 10/111,723 dated Oct. 9, 2009 (11 pages).
United States Patent Office Action for U.S. Appl. No. 10/111,723 dated Aug. 6, 2008 (25 pages).
United States Patent Office Action for U.S. Appl. No. 10/111,723 dated Mar. 12, 2008 (16 pages).
United States Patent Office Action for U.S. Appl. No. 10/111,723 dated Jul. 20, 2007 (27 pages).
United States Patent Office Action for U.S. Appl. No. 10/111,723 dated Dec. 1, 2006 (31 pages).
United States Patent Office Action for U.S. Appl. No. 10/111,723 dated Dec. 19, 2005 (20 pages).
United States Patent Office Action for U.S. Appl. No. 10/111,723 dated May 24, 2004 (22 pages).
United States Patent Office Action for U.S. Appl. No. 10/111,723 dated Sep. 20, 2010 (6 pages).
United States Patent Office Action for U.S. Appl. No. 10/111,723 dated Feb. 16, 2011 (15 pages).
United States Patent Office Action for U.S. Appl. No. 10/111,723 dated Aug. 2, 2011 (14 pages).
United States Patent Office Action for U.S. Appl. No. 10/111,723 dated May 14, 2013 (16 pages).
United States Patent Office Notice of Allowance for U.S. Appl. No. 10/111,723 dated Nov. 5, 2013 (14 pages).
United States Patent Office Action for U.S. Appl. No. 14/180,505 dated Sep. 26, 2014 (25 pages).
United States Patent Office Action for U.S. Appl. No. 14/180,505 dated Feb. 13, 2015 (33 pages).
United States Patent Office Action for U.S. Appl. No. 08/718,425 dated Jun. 7, 1999 (8 pages).
United States Patent Office Notice of Allowance for U.S. Appl. No. 08/718,425 dated Nov. 12, 1999 (6 pages).
United States Patent Office Action for U.S. Appl. No. 08/718,425 dated Mar. 13, 1998 (8 pages).
United States Patent Office Action for U.S. Appl. No. 08/718,425 dated Jun. 18, 1997 (10 pages).
United States Patent Office Action for U.S. Appl. No. 08/718,425 dated Apr. 15, 1997 (10 pages).
United States Patent Office Advisory Action for U.S. Appl. No. 09/156,946 dated May 2, 2001 (5 pages).
United States Patent Office Action for U.S. Appl. No. 09/156,946 dated Oct. 24, 2000 (8 pages).
United States Patent Office Action for U.S. Appl. No. 09/156,946 dated Apr. 26, 2000 (10 pages).
United States Patent Office Action for U.S. Appl. No. 09/838,469 dated Sep. 10, 2002 (9 pages).
United States Patent Office Action for U.S. Appl. No. 09/396,154 dated Jan. 2, 2002 (9 pages).
United States Patent Office Action for U.S. Appl. No. 09/396,154 dated Jul. 3, 2001 (10 pages).
United States Patent Office Action for U.S. Appl. No. 09/396,154 dated Jul. 16, 2002 (4 pages).
United States Patent Office Action for U.S. Appl. No. 10/378,168 dated Oct. 12, 2006 (13 pages).
United States Patent Office Action for U.S. Appl. No. 10/378,168 dated Feb. 9, 2006 (18 pages).

(56) References Cited

OTHER PUBLICATIONS

United States Patent Office Action for U.S. Appl. No. 11/291,644 dated Jan. 26, 2009 (13 pages).
United States Patent Office Action for U.S. Appl. No. 11/291,644 dated Jul. 8, 2008 (18 pages).
United States Patent Office Action for U.S. Appl. No. 11/811,898 dated Sep. 17, 2009 (23 pages).
United States Patent Office Action for U.S. Appl. No. 12/462,320 dated Feb. 2, 2011 (22 pages).
United States Patent Office Action for U.S. Appl. No. 12/462,320 dated Jun. 9, 2011 (4 pages).
United States Patent Office Action for U.S. Appl. No. 13/213,457 dated Jun. 21, 2012 (21 pages).
United States Patent Office Action for U.S. Appl. No. 13/213,457 dated Mar. 7, 2013 (18 pages).
United States Patent Office Action for U.S. Appl. No. 13/213,457 dated Oct. 16, 2013 (19 pages).
United States Patent Office Notice of Allowance for U.S. Appl. No. 13/213,457 dated Apr. 25, 2014 (8 pages).
United States Patent Office Action for U.S. Appl. No. 14/851,608 dated Nov. 15, 2016 (17 pages).
United States Patent Office Notice of Allowance for U.S. Appl. No. 14/851,608 dated Apr. 11, 2017 (17 pages).

\* cited by examiner

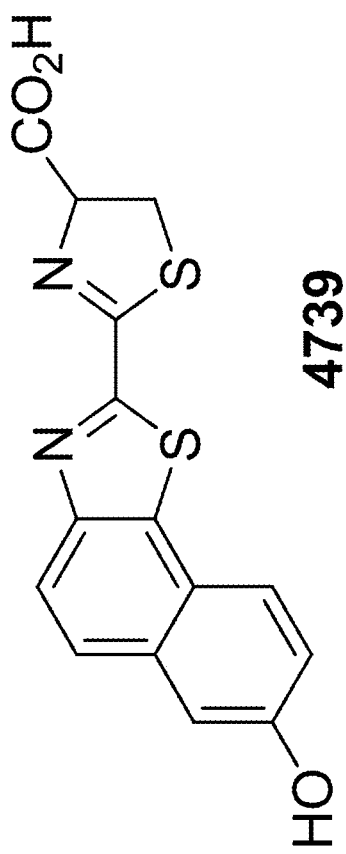
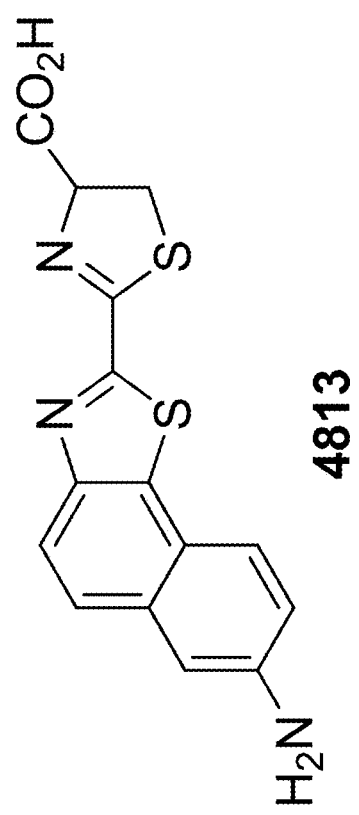
FIG. 1

CBR (pF4Ag) (SEQ ID NO: 1)

MVKREKNVIYGPEPLHPLEDLTAGEMLFRALRKHSHLPQALVDVVGDESLSYKEFF
EATVLLAQSLHNCGYKMNDVVSICAENNTRFFIPVIAAWYIGMIVAPVNESYIPDE
LCKVMGISKPQIVFTTKNILNKVLEVQSRTNFIKRIIILDTVENIHGCESLPNFISRYSD
GNIANFKPLHFDPVEQVAAILCSSGTTGLPKGVMQTHQNICVRLIHALDPRYGTQL
IPGVTVLVYLPFFHAFGFHITLGYFMVGLRVIMFRRFDQEAFLKAIQDYEVRSVINV
PSVILFLSKSPLVDKYDLSSLRELCCGAAPLAKEVAEVAAKRLNLPGIRCGFGLTESTS
AIIQTLGDEFKSGSLGRVTPLMAAKIADRETGKALGPNQVGELCIKGPMVSKGYVN
NVEATKEAIDDDGWLHSGDFGYYDEDEHFYVVDRYKELIKYKGSQVA

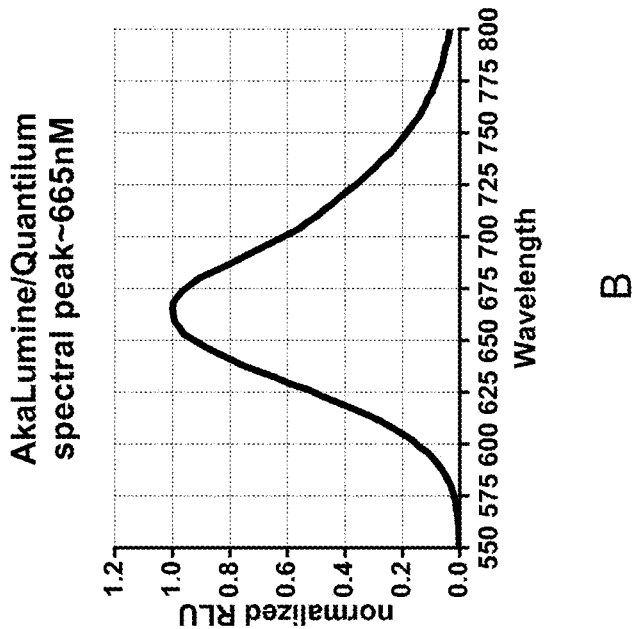
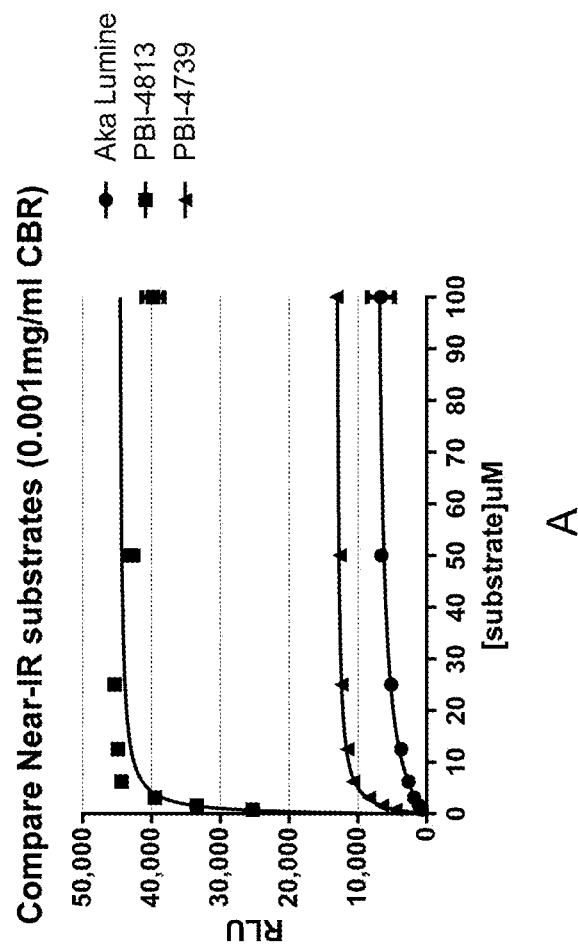
FIG. 19A
FIG. 19B

SEQUENCE LISTING

```
<160> NUMBER OF SEQ ID NOS: 10

<210> SEQ ID NO 1
<211> LENGTH: 543
<212> TYPE: PRT
<213> ORGANISM: Artificial
<220> FEATURE:
<223> OTHER INFORMATION: Synthetic Peptide

<400> SEQUENCE: 1

Met Val Lys Arg Glu Lys Asn Val Ile Tyr Gly Pro Glu Pro Leu His
1               5                   10                  15

Pro Leu Glu Asp Leu Thr Ala Gly Glu Met Leu Phe Arg Ala Leu Arg
            20                  25                  30

Lys His Ser His Leu Pro Gln Ala Leu Val Asp Val Val Gly Asp Glu
        35                  40                  45

Ser Leu Ser Tyr Lys Glu Phe Phe Glu Ala Thr Val Leu Leu Ala Gln
    50                  55                  60

Ser Leu His Asn Cys Gly Tyr Lys Met Asn Asp Val Val Ser Ile Cys
65                  70                  75                  80

Ala Glu Asn Asn Thr Arg Phe Phe Ile Pro Val Ile Ala Ala Trp Tyr
                85                  90                  95

Ile Gly Met Ile Val Ala Pro Val Asn Glu Ser Tyr Ile Pro Asp Glu
            100                 105                 110

Leu Cys Lys Val Met Gly Ile Ser Lys Pro Gln Ile Val Phe Thr Thr
        115                 120                 125

Lys Asn Ile Leu Asn Lys Val Leu Glu Val Gln Ser Arg Thr Asn Phe
    130                 135                 140

Ile Lys Arg Ile Ile Ile Leu Asp Thr Val Glu Asn Ile His Gly Cys
145                 150                 155                 160

Glu Ser Leu Pro Asn Phe Ile Ser Arg Tyr Ser Asp Gly Asn Ile Ala
                165                 170                 175

Asn Phe Lys Pro Leu His Phe Asp Pro Val Glu Gln Val Ala Ala Ile
            180                 185                 190
```

```
Leu Cys Ser Ser Gly Thr Thr Gly Leu Pro Lys Gly Val Met Gln Thr
        195                 200                 205

His Gln Asn Ile Cys Val Arg Leu Ile His Ala Leu Asp Pro Arg Tyr
210                 215                 220

Gly Thr Gln Leu Ile Pro Gly Val Thr Val Leu Val Tyr Leu Pro Phe
225                 230                 235                 240

Phe His Ala Phe Gly Phe His Ile Thr Leu Gly Tyr Phe Met Val Gly
                245                 250                 255

Leu Arg Val Ile Met Phe Arg Arg Phe Asp Gln Glu Ala Phe Leu Lys
                260                 265                 270

Ala Ile Gln Asp Tyr Glu Val Arg Ser Val Ile Asn Val Pro Ser Val
                275                 280                 285

Ile Leu Phe Leu Ser Lys Ser Pro Leu Val Asp Lys Tyr Asp Leu Ser
290                 295                 300

Ser Leu Arg Glu Leu Cys Cys Gly Ala Ala Pro Leu Ala Lys Glu Val
305                 310                 315                 320

Ala Glu Val Ala Ala Lys Arg Leu Asn Leu Pro Gly Ile Arg Cys Gly
                325                 330                 335

Phe Gly Leu Thr Glu Ser Thr Ser Ala Ile Ile Gln Thr Leu Gly Asp
                340                 345                 350

Glu Phe Lys Ser Gly Ser Leu Gly Arg Val Thr Pro Leu Met Ala Ala
                355                 360                 365

Lys Ile Ala Asp Arg Glu Thr Gly Lys Ala Leu Gly Pro Asn Gln Val
                370                 375                 380

Gly Glu Leu Cys Ile Lys Gly Pro Met Val Ser Lys Gly Tyr Val Asn
385                 390                 395                 400

Asn Val Glu Ala Thr Lys Glu Ala Ile Asp Asp Gly Trp Leu His
                405                 410                 415

Ser Gly Asp Phe Gly Tyr Tyr Asp Glu Asp Glu His Phe Tyr Val Val
                420                 425                 430

Asp Arg Tyr Lys Glu Leu Ile Lys Tyr Lys Gly Ser Gln Val Ala Pro
                435                 440                 445

Ala Glu Leu Glu Glu Ile Leu Leu Lys Asn Pro Cys Ile Arg Asp Val
450                 455                 460

Ala Val Val Gly Ile Pro Asp Leu Glu Ala Gly Glu Leu Pro Ser Ala
465                 470                 475                 480

Phe Val Val Lys Gln Pro Gly Thr Glu Ile Thr Ala Lys Glu Val Tyr
                485                 490                 495

Asp Tyr Leu Ala Glu Arg Val Ser His Thr Lys Tyr Leu Arg Gly Gly
                500                 505                 510

Val Arg Phe Val Asp Ser Ile Pro Arg Asn Val Thr Gly Lys Ile Thr
                515                 520                 525

Arg Lys Glu Leu Leu Lys Gln Leu Leu Val Lys Ala Gly Gly Val
                530                 535                 540

<210> SEQ ID NO 2
<211> LENGTH: 543
<212> TYPE: PRT
<213> ORGANISM: Artificial
<220> FEATURE:
<223> OTHER INFORMATION: Synthetic Peptide
```

<400> SEQUENCE: 2

```
Met Val Lys Arg Glu Lys Asn Val Ile Tyr Gly Pro Glu Pro Leu His
1               5                   10                  15
Pro Leu Glu Asp Leu Thr Ala Gly Glu Met Leu Phe Arg Ala Leu Arg
            20                  25                  30
Lys His Ser His Leu Pro Gln Ala Leu Val Asp Val Gly Asp Glu
        35                  40                  45
Ser Leu Ser Tyr Lys Glu Phe Phe Glu Ala Thr Val Leu Leu Ala Gln
50                  55                  60
Ser Leu His Asn Cys Gly Tyr Lys Met Asn Asp Val Val Ser Ile Cys
65                  70                  75                  80
Ala Glu Asn Asn Thr Arg Phe Phe Ile Pro Val Ile Ala Ala Trp Tyr
                85                  90                  95
Ile Gly Met Ile Val Ala Pro Val Asn Glu Ser Tyr Ile Pro Asp Glu
            100                 105                 110
Leu Cys Lys Val Met Gly Ile Ser Lys Pro Gln Ile Val Phe Thr Thr
        115                 120                 125
Lys Asn Ile Leu Asn Lys Val Leu Glu Val Gln Ser Arg Thr Asn Phe
    130                 135                 140
Ile Lys Arg Ile Ile Ile Leu Asp Thr Val Glu Asn Ile His Gly Cys
145                 150                 155                 160
Glu Ser Leu Pro Asn Phe Ile Ser Arg Tyr Ser Asp Gly Asn Ile Ala
                165                 170                 175
Asn Phe Lys Pro Leu His Phe Asp Pro Val Glu Gln Val Ala Ala Ile
            180                 185                 190
Leu Cys Ser Ser Gly Thr Thr Gly Leu Pro Lys Gly Val Met Gln Thr
        195                 200                 205
His Gln Asn Ile Cys Val Arg Leu Ile His Ala Leu Asp Pro Arg Tyr
    210                 215                 220
Gly Thr Gln Leu Ile Pro Gly Val Thr Val Leu Val Tyr Leu Pro Phe
225                 230                 235                 240
Phe His Ala Phe Gly Phe His Ile Thr Leu Gly Tyr Phe Met Val Gly
                245                 250                 255
Leu Arg Val Ile Met Phe Arg Arg Phe Asp Gln Glu Ala Phe Leu Lys
            260                 265                 270
Ala Ile Gln Asp Tyr Glu Val Arg Ser Val Ile Asn Val Pro Ser Val
        275                 280                 285
Ile Leu Phe Leu Ser Lys Ser Pro Leu Val Asp Lys Tyr Asp Leu Ser
    290                 295                 300
Ser Leu Arg Glu Leu Cys Cys Gly Ala Ala Pro Leu Ala Lys Glu Val
305                 310                 315                 320
Ala Glu Val Ala Ala Lys Arg Leu Asn Leu Pro Gly Ile Ser Cys Gly
                325                 330                 335
Phe Gly Leu Thr Glu Ser Thr Ser Ala Ile Ile Gln Thr Leu Arg Asp
            340                 345                 350
Glu Phe Lys Ser Gly Ser Leu Gly Arg Val Thr Pro Leu Met Ala Ala
        355                 360                 365
Lys Ile Ala Asp Arg Glu Thr Gly Lys Ala Leu Gly Pro Asn Gln Val
    370                 375                 380
Gly Glu Leu Cys Ile Lys Gly Pro Met Val Ser Lys Gly Tyr Val Asn
385                 390                 395                 400
Asn Val Glu Ala Thr Lys Glu Ala Ile Asp Asp Gly Trp Leu His
                405                 410                 415
```

```
Ser Gly Asp Phe Gly Tyr Tyr Asp Glu Asp Glu His Phe Tyr Val Val
            420                 425                 430

Asp Arg Tyr Lys Glu Leu Ile Lys Tyr Lys Gly Ser Gln Val Ala Pro
        435                 440                 445

Ala Glu Leu Glu Glu Ile Leu Leu Lys Asn Pro Cys Ile Arg Asp Val
    450                 455                 460

Ala Val Val Gly Ile Pro Asp Leu Glu Ala Gly Glu Leu Pro Ser Ala
465                 470                 475                 480

Phe Val Val Lys Gln Pro Gly Thr Glu Ile Thr Ala Lys Glu Val Tyr
            485                 490                 495

Asp Tyr Leu Ala Glu Arg Val Ser His Thr Lys Tyr Leu Arg Gly Gly
        500                 505                 510

Val Arg Phe Val Asp Ser Ile Pro Arg Asn Val Thr Gly Lys Ile Thr
    515                 520                 525

Arg Lys Glu Leu Leu Lys Gln Leu Leu Val Lys Ala Gly Gly Val
            530                 535                 540

<210> SEQ ID NO 3
<211> LENGTH: 543
<212> TYPE: PRT
<213> ORGANISM: Artificial
<220> FEATURE:
<223> OTHER INFORMATION: Synthetic Peptide

<400> SEQUENCE: 3

Met Val Lys Arg Glu Lys Asn Val Ile Tyr Gly Pro Glu Pro Leu His
1               5                   10                  15

Pro Leu Glu Asp Leu Thr Ala Gly Glu Met Leu Phe Arg Ala Leu Arg
            20                  25                  30

Lys His Ser His Leu Pro Gln Ala Leu Val Asp Val Val Gly Asp Glu
        35                  40                  45

Ser Leu Ser Tyr Lys Glu Phe Phe Glu Ala Thr Val Leu Leu Ala Gln
    50                  55                  60

Ser Leu His Asn Cys Gly Tyr Lys Met Asn Asp Val Val Ser Ile Cys
65                  70                  75                  80

Ala Glu Asn Asn Thr Arg Phe Phe Ile Pro Val Ile Ala Ala Trp Tyr
                85                  90                  95

Ile Gly Met Ile Val Ala Pro Val Asn Glu Ser Tyr Ile Pro Asp Glu
            100                 105                 110

Leu Cys Lys Val Met Gly Ile Ser Lys Pro Gln Ile Val Phe Thr Thr
        115                 120                 125

Lys Asn Ile Leu Asn Lys Val Leu Glu Val Gln Ser Arg Thr Asn Phe
    130                 135                 140

Ile Lys Arg Ile Ile Ile Leu Asp Thr Val Glu Asn Ile His Gly Cys
145                 150                 155                 160

Glu Ser Leu Pro Asn Phe Ile Ser Arg Tyr Ser Asp Gly Asn Ile Ala
                165                 170                 175

Asn Phe Lys Pro Leu His Phe Asp Pro Val Glu Gln Val Ala Ala Ile
            180                 185                 190

Leu Cys Ser Ser Gly Thr Thr Gly Leu Pro Lys Gly Val Met Gln Thr
        195                 200                 205

His Gln Asn Ile Cys Val Arg Leu Ile His Ala Leu Asp Pro Arg Tyr
    210                 215                 220

Gly Thr Gln Leu Ile Pro Gly Val Thr Val Leu Val Tyr Leu Pro Phe
225                 230                 235                 240
```

```
Phe His Ala Phe Gly Phe His Ile Thr Leu Ser Tyr Phe Met Val Gly
                245                 250                 255

Leu Arg Val Ile Met Phe Arg Arg Phe Asp Gln Glu Ala Phe Leu Lys
            260                 265                 270

Ala Ile Gln Asp Tyr Glu Val Arg Ser Val Ile Asn Val Pro Ser Val
        275                 280                 285

Ile Leu Phe Leu Ser Lys Ser Pro Leu Val Asp Lys Tyr Asp Leu Ser
    290                 295                 300

Ser Leu Arg Glu Leu Cys Cys Gly Ala Ala Pro Leu Ala Lys Glu Val
305                 310                 315                 320

Ala Glu Val Ala Ala Lys Arg Leu Asn Leu Pro Gly Ile Arg Cys Gly
                325                 330                 335

Phe Gly Leu Thr Glu Ser Thr Ser Ala Ile Ile Gln Thr Leu Gly Asp
            340                 345                 350

Glu Phe Lys Ser Gly Ser Leu Gly Arg Val Thr Pro Leu Met Ala Ala
        355                 360                 365

Lys Ile Ala Asp Arg Glu Thr Gly Lys Ala Leu Gly Pro Asn Gln Val
    370                 375                 380

Gly Glu Leu Cys Phe Lys Gly Pro Met Val Ser Lys Gly Tyr Val Asn
385                 390                 395                 400

Asn Val Glu Ala Thr Lys Glu Ala Ile Asp Asp Gly Trp Leu His
                405                 410                 415

Ser Gly Asp Phe Gly Tyr Tyr Asp Glu Asp His Phe Tyr Val Val
            420                 425                 430

Asp Arg Tyr Lys Glu Leu Ile Lys Tyr Lys Gly Arg Gln Val Ala Pro
        435                 440                 445

Ala Glu Leu Glu Glu Ile Leu Leu Lys Asn Pro Cys Ile Arg Asp Val
    450                 455                 460

Ala Val Val Gly Ile Pro Asp Leu Glu Ala Gly Glu Leu Pro Ser Ala
465                 470                 475                 480

Phe Val Val Lys Gln Pro Gly Thr Glu Ile Thr Ala Lys Glu Val Tyr
                485                 490                 495

Asp Tyr Leu Ala Glu Arg Val Ser His Thr Lys Tyr Leu Arg Gly Gly
            500                 505                 510

Val Arg Phe Val Asp Ser Ile Pro Arg Asn Val Thr Gly Lys Ile Thr
        515                 520                 525

Arg Lys Glu Leu Leu Lys Gln Leu Leu Val Lys Ala Gly Gly Val
    530                 535                 540

<210> SEQ ID NO 4
<211> LENGTH: 543
<212> TYPE: PRT
<213> ORGANISM: Artificial
<220> FEATURE:
<223> OTHER INFORMATION: Synthetic Peptide

<400> SEQUENCE: 4

Met Val Lys Arg Glu Lys Asn Val Ile Tyr Gly Pro Glu Pro Leu His
1               5                   10                  15

Pro Leu Glu Asp Leu Thr Ala Gly Glu Met Leu Phe Arg Ala Leu Arg
            20                  25                  30

Lys His Ser His Leu Pro Gln Ala Leu Val Asp Val Val Gly Asp Glu
        35                  40                  45

Ser Leu Asn Tyr Lys Glu Phe Phe Glu Ala Thr Val Leu Leu Ala Gln
    50                  55                  60
```

```
Ser Leu His Asn Cys Gly Tyr Lys Met Asn Asp Val Val Ser Ile Cys
 65                  70                  75                  80

Ala Glu Asn Asn Thr Arg Phe Phe Ile Pro Val Ile Ala Ala Trp Tyr
             85                  90                  95

Ile Gly Met Ile Val Ala Pro Val Asn Glu Ser Tyr Ile Pro Asp Glu
            100                 105                 110

Leu Cys Lys Val Met Gly Ile Ser Lys Pro Gln Ile Val Phe Thr Thr
            115                 120                 125

Lys Asn Ile Leu Asn Lys Val Leu Glu Val Gln Ser Arg Thr Asn Phe
130                 135                 140

Ile Lys Arg Ile Ile Ile Leu Asp Thr Val Glu Asn Ile His Gly Cys
145                 150                 155                 160

Glu Ser Leu Pro Asn Phe Ile Ser Arg Tyr Ser Asp Gly Asn Ile Ala
                165                 170                 175

Asn Phe Lys Pro Leu His Phe Asp Pro Val Glu Gln Val Ala Ala Ile
            180                 185                 190

Leu Cys Ser Ser Gly Thr Thr Gly Leu Pro Lys Gly Val Met Gln Thr
            195                 200                 205

His Gln Asn Ile Cys Val Arg Leu Ile His Ala Leu Asp Pro Arg Tyr
210                 215                 220

Gly Thr Gln Leu Ile Pro Gly Val Thr Val Leu Val Tyr Leu Pro Phe
225                 230                 235                 240

Phe His Ala Phe Gly Phe His Ile Thr Leu Gly Tyr Phe Met Val Gly
                245                 250                 255

Leu Arg Val Ile Met Phe Arg Arg Phe Asp Gln Glu Ala Phe Leu Lys
            260                 265                 270

Ala Ile Gln Asp Tyr Glu Val Arg Ser Val Ile Asn Val Pro Ser Val
            275                 280                 285

Ile Leu Phe Leu Ser Lys Ser Pro Leu Val Asp Lys Tyr Asp Leu Ser
            290                 295                 300

Ser Leu Arg Glu Leu Cys Cys Gly Ala Ala Pro Leu Ala Lys Glu Val
305                 310                 315                 320

Ala Glu Val Ala Ala Lys Arg Leu Asn Leu Pro Gly Ile Ser Cys Gly
                325                 330                 335

Phe Gly Leu Thr Glu Ser Thr Ser Ala Ile Ile Gln Thr Leu Arg Asp
            340                 345                 350

Glu Phe Lys Ser Gly Ser Leu Gly Arg Val Thr Pro Leu Met Ala Ala
            355                 360                 365

Lys Ile Ala Asp Arg Glu Thr Gly Lys Ala Leu Gly Pro Asn Gln Val
370                 375                 380

Gly Glu Leu Cys Ile Lys Gly Pro Met Val Ser Lys Gly Tyr Val Asn
385                 390                 395                 400

Asn Val Glu Ala Thr Lys Glu Ala Ile Asp Asp Gly Trp Leu His
                405                 410                 415

Ser Gly Asp Phe Gly Tyr Tyr Asp Glu Asp Glu His Phe Tyr Val Val
            420                 425                 430

Asp Arg Tyr Lys Glu Leu Ile Lys Tyr Lys Gly Arg Gln Val Ala Pro
            435                 440                 445

Ala Glu Leu Glu Glu Ile Leu Leu Lys Asn Pro Cys Ile Arg Asp Val
450                 455                 460

Ala Val Val Gly Ile Pro Asp Leu Glu Ala Gly Glu Leu Pro Ser Ala
465                 470                 475                 480
```

```
Phe Val Val Lys Gln Pro Gly Thr Glu Ile Thr Ala Lys Glu Val Tyr
                485                 490                 495

Asp Tyr Leu Ala Glu Arg Val Ser His Thr Lys Tyr Leu Arg Gly Gly
            500                 505                 510

Val Arg Phe Val Asp Ser Ile Pro Arg Asn Val Thr Gly Lys Ile Thr
        515                 520                 525

Arg Lys Glu Leu Leu Lys Gln Leu Leu Val Lys Ala Gly Gly Val
    530                 535                 540

<210> SEQ ID NO 5
<211> LENGTH: 1632
<212> TYPE: DNA
<213> ORGANISM: Artificial
<220> FEATURE:
<223> OTHER INFORMATION: Synthetic Oligonucleotide; Variant ATG 343 =
      CBR sequence (amino acid sequence SEQ ID NO:1)

<400> SEQUENCE: 5
```

| | | | | | |
|---|---|---|---|---|---|
| atggtaaagc | gtgagaaaaa | tgtcatctat | ggccctgagc | tctccatcc  | tttggaggat | 60 |
| ttgactgccg | gcgaaatgct | gtttcgtgct | ctccgcaagc | actctcattt | gcctcaagcc | 120 |
| ttggtcgatg | tggtcggcga | tgaatctttg | agctacaagg | agttttttga | ggcaaccgtc | 180 |
| ttgctggctc | agtccctcca | caattgtggc | tacaagatga | cgacgtcgt  | tagtatctgt | 240 |
| gctgaaaaca | ataccgtttt | cttcattcca | gtcatcgccg | catggtatat | cggtatgatc | 300 |
| gtggctccag | tcaacgagag | ctacattccc | gacgaactgt | gtaaagtcat | gggtatctct | 360 |
| aagccacaga | ttgtcttcac | cactaagaat | attctgaaca | agtcctgga  | agtccaaagc | 420 |
| cgcaccaact | ttattaagcg | tatcatcatc | ttggacactg | tggagaatat | tcacggttgc | 480 |
| gaatctttgc | ctaatttcat | ctctcgctat | tcagacggca | acatcgcaaa | ctttaaacca | 540 |
| ctccacttcg | accctgtgga | acaagttgca | gccattctgt | gtagcagcgg | tactactgga | 600 |
| ctcccaaagg | gagtcatgca | gacccatcaa | acatttgcg  | tgcgtctgat | ccatgctctc | 660 |
| gatccacgct | acggcactca | gctgattcct | ggtgtcaccg | tcttggtcta | cttgcctttc | 720 |
| ttccatgctt | tcggctttca | tattactttg | ggttacttta | tggtcggtct | ccgcgtgatt | 780 |
| atgttccgcc | gttttgatca | ggaggctttc | ttgaaagcca | tccaagatta | tgaagtccgc | 840 |
| agtgtcatca | acgtgcctag | cgtgatcctg | ttttttgtcta | agagcccact | cgtggacaag | 900 |
| tacgacttgt | cttcactgcg | tgaattgtgt | tgcggtgccg | ctccactggc | taaggaggtc | 960 |
| gctgaagtgg | ccgccaaacg | cttgaatctt | ccagggattc | gttgtggctt | cggcctcacc | 1020 |
| gaatctacca | gtgcgattat | ccagactctc | ggggatgagt | ttaagagcgg | ctctttgggc | 1080 |
| cgtgtcactc | cactcatggc | tgctaagatc | gctgatcgcg | aaactggtaa | ggctttgggc | 1140 |
| ccgaaccaag | tgggcgagct | gtgtatcaaa | ggccctatgg | tgagcaaggg | ttatgtcaat | 1200 |
| aacgttgaag | ctaccaagga | ggccatcgac | gacgacggct | ggttgcattc | tggtgatttt | 1260 |
| ggatattacg | acgaagatga | gcatttttac | gtcgtggatc | gttacaagga | gctgatcaaa | 1320 |
| tacaagggta | gccaggttgc | tccagctgag | ttggaggaga | ttctgttgaa | aaatccatgc | 1380 |
| attcgcgatg | tcgctgtggt | cggcattcct | gatctggagg | ccggcgaact | gccttctgct | 1440 |
| ttcgttgtca | gcagcctgg  | tacagaaatt | accgccaaag | aagtgtatga | ttacctggct | 1500 |
| gaacgtgtga | gccatactaa | gtacttgcgt | ggcggcgtgc | gttttgttga | ctccatccct | 1560 |
| cgtaacgtaa | caggcaaaat | tacccgcaag | gagctgttga | acaattgtt  | ggtgaaggcc | 1620 |
| ggcggtgttt | aa         |            |            |            |            | 1632 |

<210> SEQ ID NO 6
<211> LENGTH: 1632
<212> TYPE: DNA
<213> ORGANISM: Artificial
<220> FEATURE:
<223> OTHER INFORMATION: Synthetic Oligonucleotide; Variant ATG 1240 =
      CBR sequence + R334S/G351R (amino acid sequence SEQ ID NO:2)

<400> SEQUENCE: 6

```
atggtaaagc gtgagaaaaa tgtcatctat ggccctgagc ctctccatcc tttggaggat    60
ttgactgccg gcgaaatgct gtttcgtgct ctccgcaagc actctcattt gcctcaagcc   120
ttggtcgatg tggtcggcga tgaatctttg agctacaagg agttttttga ggcaaccgtc   180
ttgctggctc agtccctcca caattgtggc tacaagatga cgacgtcgt tagtatctgt    240
gctgaaaaca tacccgtttc ttcattcca gtcatcgccg catggtatat cggtatgatc    300
gtggctccag tcaacgagag ctacattccc gacgaactgt gtaaagtcat gggtatctct   360
aagccacaga ttgtcttcac cactaagaat attctgaaca agtcctggga agtccaaagc   420
cgcaccaact ttattaagcg tatcatcatc ttggacactg tggagaatat tcacggttgc   480
gaatctttgc ctaatttcat ctctcgctat tcagacggca acatcgcaaa ctttaaacca   540
ctccacttcg accctgtgga acaagttgca gccattctgt gtagcagcgg tactactgga   600
ctcccaaagg gagtcatgca gacccatcaa acatttgcg tgcgtctgat ccatgctctc   660
gatccacgct acggcactca gctgattcct ggtgtcaccg tcttggtcta cttgcctttc   720
ttccatgctt tcggctttca tattactttg ggttacttta tggtcggtct ccgcgtgatt   780
atgttccgcc gttttgatca ggaggctttc ttgaaagcca tccaagatta tgaagtccgc   840
agtgtcatca acgtgcctag cgtgatcctg ttttttgtcta agagcccact cgtggacaag   900
tacgacttgt cttcactgcg tgaattgtgt tgcggtgccg ctccactggc taaggaggtc   960
gctgaagtgg ccgccaaacg cttgaatctt ccagggatta ttgtggctt cggcctcacc  1020
gaatctacca gtgcgattat ccagactctc cgggatgagt ttaagagcgg ctcttggc   1080
cgtgtcactc cactcatggc tgctaagatc gctgatcgcg aaactggtaa ggctttgggc  1140
ccgaaccaag tgggcgagct gtgtatcaaa ggccctatgg tgagcaaggg ttatgtcaat  1200
aacgttgaag ctaccaagga ggccatcgac gacgacggct ggttgcattc tggtgatttt  1260
ggatattacg acgaagatga gcatttttac gtcgtggatc gttacaagga gctgatcaaa  1320
tacaagggta gccaggttgc tccagctgag ttggaggaga ttctgttgaa aaatccatgc  1380
attcgcgatg tcgctgtggt cggcattcct gatctggagg ccggcgaact gccttctgct  1440
ttcgttgtca gcagcctgg tacagaaatt accgccaaag aagtgtatga ttacctggct  1500
gaacgtgtga gccatactaa gtacttgcgt ggcggcgtgc gttttgttga ctccatccct  1560
cgtaacgtaa caggcaaaat tacccgcaag gagctgttga acaattgtt ggtgaaggcc  1620
ggcggtgttt aa                                                      1632
```

<210> SEQ ID NO 7
<211> LENGTH: 1632
<212> TYPE: DNA
<213> ORGANISM: Artificial
<220> FEATURE:
<223> OTHER INFORMATION: Synthetic Oligonucleotide; Variant ATG 1929 =
      CBR sequence + R334S/G351R (codon optimized for RNA structure and
      codon usage in rodents) (amino acid sequence SEQ ID NO:2)

<400> SEQUENCE: 7

```
atggttaaga gagaaaaaaa tgttatttat ggtcctgaac ctctgcatcc tctggaagat      60
ctcactgcag gagagatgct gtttcgcgcc ctgcgcaagc actctcactt gccgcaggct     120
ctggtcgacg tggtgggtga cgagtccctg agctacaagg agttcttcga ggcgactgtc     180
ctgctggcac agagtctcca taactgcggc tacaagatga cgatgtggt ttccatctgc      240 gcagagaaca cactagatt ctttatccca gtgatcgctg cttggtacat cggcatgatt     300
gtcgcaccag tcaatgaatc ttacattcca gatgaactgt gtaaggttat gggaatttcc     360
aaaccgcaga tcgtgttcac aactaagaac atcctgaaca aggttctgga agtgcagagt     420
cggaccaatt tcatcaagcg tattatcatc ctggacacag tggagaacat ccacggttgc     480
gaatccctcc ccaacttcat ctctcgttat agcgatggca acatcgctaa tttcaaaccc     540
ctgcatttcg atcctgttga acaggttgcc gccatcctgt gctcctctgg gaccaccgga     600
ctgccgaaag gcgtgatgca gacccatcag aacatctgcg tgaggctgat ccacgccctg     660
gacccacgct atggaactca gctgatccca ggagtcactg tgctggttta cctcccttt      720 tttcacgcct tcggtttcca cattaccctc gggtacttta tggtcggcct ccgcgttatc     780
atgttccgtc gctttgacca ggaggctttc ctgaaggcca tccaggatta tgaggtgagg     840
agtgtgatta acgtcccaag cgtgatcctg ttcctgtcta agtcccctct ggttgacaag     900
tacgatctga gctccctgcg tgagctgtgc tgcggggctg caccactggc caaagaagtc     960
gcggaagtgg ctgccaaacg cctgaacctg ccgggtatct cctgtggctt cggcctgaca    1020
gagagcacat ccgctatcat ccagacactg cgggatgagt ttaagtccgg ttccctgggc    1080
cgggttacac ccctgatggc agccaagatc gccgaccgcg agactgggaa ggccctcgga    1140
cctaaccagg tcggagagct gtgtattaag ggccccatgt gtccaagggg atatgtgaac    1200
aacgtggaag ctacaaagga ggcgattgat gatgacggat ggctccatag cggagacttt    1260
gggtactatg acgaggacga gcacttctat gtggtcgaca ggtacaagga gctgatcaag    1320
tacaagggct cccaggtggc cccagctgaa ctggaggaga ttctgttgaa gaacccttgt    1380
atcagagatg tggctgttgt ggggattcct gacctcgaag caggtgagct gccctccgct    1440
ttcgtggtga agcagcctgg tactgagatc accgccaaag aggtgtacga ttacctggct    1500
gagcgcgtgt cccacaccaa atacctccgc ggcggggtcc gtttcgtgga ctccattccc    1560
aggaacgtga ccggcaagat cacccgcaag gagctgctga agcagctgct ggttaaggct    1620
ggcggcgttt aa                                                        1632
```

<210> SEQ ID NO 8
<211> LENGTH: 1632
<212> TYPE: DNA
<213> ORGANISM: Artificial
<220> FEATURE:
<223> OTHER INFORMATION: Synthetic Oligonucleotide; Variant ATG 1944 =
    CBR sequence + R334S/G351R (codon optimized for RNA structure and
    codon usage in CHO cells) (amino acid sequence SEQ ID NO:2)

<400> SEQUENCE: 8

```
atggtcaaga gagaaaagaa cgtcatctac ggtcccgagc cctgcacccc cctggaagat      60
ctgactgccg gagagatgct tttccgggct ctgcgcaagc atagccacct cccgcaagca     120
ctggtggacg tggtcgggga cgagtcactg tcgtataagg agttcttcga agcgaccgtg     180
ctgctggccc agtccctgca caactgcgga tacaagatga tgacgtggt gtcgatttgc      240 gccgaaaaca cacccggtt cttcattccc gtgatcgccg cttggtacat cgggatgatc     300
```

```
gtggccccg   tcaacgagtc   atacatccct   gacgagctgt   gcaaggtcat   gggtatatca        360
aagccccaga   tcgtgttcac   cactaagaac   atcttgaaca   aagtgctgga   agtgcagtcc        420
cggaccaact   ttatcaagcg   gatcatcatc   ctggataccg   tggagaacat   ccacggttgt        480
gaatcgctgc   ctaacttcat   tagccggtac   tcggacggca   atatcgcaaa   cttcaagccc        540
ctccatttcg   accctgtgga   acaagtggcc   gcgatcttgt   gttcatcggg   caccaccgga        600
ctcccaaagg   gggtcatgca   gactcatcag   aacatttgcg   tgagactgat   tcacgccctg        660
gaccctcgct   acgggactca   actcattccg   ggagtgaccg   tgctcgtgta   tttgccgttc        720
ttccacgcct   ttggcttcca   catcaccctg   gggtacttta   tggtcggact   gcgcgtgatc        780
atgttccgga   gatttgacca   ggaggcattc   ctgaaagcca   tccaagacta   cgaagtccgg        840
agcgtgatta   acgtgccgag   cgtgatcttg   ttcctgtcca   agtccccttt   ggtggataag        900
tacgacctgt   cgagcctgag   agagctctgt   tgcggcgcgg   ccccgctcgc   taaggaagtg        960
gccgaagtgg   cggctaagag   gctgaaccct   cctggaattt   cctgcggctt   cggcctgacc       1020
gagtccacta   gcgcgatcat   tcagaccctg   cgcgatgagt   tcaaatccgg   ctctctgggc       1080
cgcgtgactc   ctctgatggc   cgcaaagatc   gcggacaggg   aaactgggaa   agccctcggt       1140
ccgaatcagg   tcggagagct   ctgcattaag   ggaccaatgg   tgtccaaggg   atacgtgaac       1200
aacgtggagg   ccaccaagga   agccatcgac   gacgacggat   ggctgcattc   cggagacttc       1260
gggtactacg   acgaggatga   gcacttctac   gtggtggatc   ggtacaagga   gcttatcaag       1320
tacaagggct   cccaggtcgc   tccggccgag   ctggaagaaa   ttctgctcaa   gaacccatgc       1380
atccgagatg   tggccgtggt   cggtatcccc   gacctggagg   ccggagaact   gccgtccgcc       1440
ttcgtggtca   gcagcccgg   cacagagatt   accgcgaagg   aagtgtacga   ttacctggcc       1500
gaacgggtgt   cccacacgaa   gtatcttcgc   ggcggagtgc   gcttcgtcga   ctccatcccg       1560
agaaacgtga   ccggaaagat   taccaggaag   gaactcctga   agcagctgct   cgtgaaagcc       1620
ggcggagtgt   ag                                                                 1632
```

<210> SEQ ID NO 9
<211> LENGTH: 1632
<212> TYPE: DNA
<213> ORGANISM: Artificial
<220> FEATURE:
<223> OTHER INFORMATION: Synthetic Oligonucleotide; Variant ATG 1945 =
    CBR sequence + R334S/G351R (codon optimized for RNA structure and
    codon usage in mouse lung and liver cells) (amino acid sequence
    SEQ ID NO:2)

<400> SEQUENCE: 9

```
atggttaaga   gagaaaagaa   cgtgatatac   ggtccagaac   ccctccaccc   acttgaagat         60
cttacagccg   gggaaatgtt   attccgtgca   cttaggaaac   atagccattt   gccgcaagcc        120
ctggtcgatg   tcgtcgggga   cgagtctctg   agttacaagg   agttttttcga   agccaccgtg        180 ttgctagctc   agtcactcca   taactgtggt   tacaagatga   atgacgtggt   gtcaatctgc        240
gctgaaaaca   atacccgctt   ctttatcccc   gtgattgctg   cttggtatat   cggcatgatt        300
gtggccccgg   ttaatgagag   ttacatcccc   gacgagctgt   gtaaagtcat   gggaattagc        360
aagccgcaga   tagtgtttac   cacgaagaac   atcctcaaca   aggtcctcga   ggtccagtct        420
cggaccaatt   tcattaagag   gattatcatc   ctggacaccg   tagaaaatat   ccatggctgc        480
gagtctcttc   ccaactttat   ctctcgctat   tccgacggaa   atatcgcaaa   tttcaaacca        540
ctgcattttg   acccggtcga   acaagtggct   gctatcctgt   gttcgtccgg   tacaacgggc        600
```

```
ctacctaagg gcgttatgca gactcatcag aatatctgcg tgcgcttaat tcacgctctt      660
gacccacgtt acggcacaca gttaatcccc ggtgttactg tcctcgtata ccttccattt      720
ttccatgcat tcggctttca tattacactt ggctacttta tggttggcct tcgcgtaatt      780
atgtttcggc gatttgacca ggaagcattt ctgaaagcta ttcaggatta tgaagttcgc      840
tctgtcatca atgtgccaag tgtcatattg tttctgtcta aaagtcccct cgtggacaaa      900
tatgatcttt cttctctccg cgaactgtgc tgcggcgcgg ctccacttgc taaggaagtg      960
gctgaggtcg cagctaagcg cctaaatctt ccgggaatct cctgcggttt tgggcttacc     1020
gaatcaacat ctgccataat tcagacactt agggacgaat tcaagagtgg tagtctgggc     1080
cgcgtgacgc cgcttatggc tgctaagatc gctgacaggg aaactgggaa ggctctgggt     1140
cctaatcaag ttggggaact ttgcattaag ggccctatgg tgtccaaggg atacgtaaac     1200
aatgtcgaag ctacgaagga ggctatcgat gacgatggat ggcttcatag cggcgacttt     1260
gggtactatg acgaggacga acacttttat gtggtggacc gctacaagga actcataaag     1320
tacaagggta gccaggtcgc cccggctgag ctcgaagaaa tccttctcaa aaatccctgt     1380
atccgcgatg tggccgtcgt tggcataccg gatcttgaag ccggagaact tccctctgca     1440
tttgtggtca gcagccagg aaccgaaatc actgcgaagg aggtgtacga ttatctcgcc     1500
gaacgcgtgt ctcacaccaa gtacctaaga ggaggggttc ggtttgtgga tagtatacct     1560
cgcaatgtca caggaaaaat cacccggaaa gagctgttga acagctgct cgtaaaggcc     1620 ggtggtgtct ga                                                         1632
```

<210> SEQ ID NO 10
<211> LENGTH: 1632
<212> TYPE: DNA
<213> ORGANISM: Artificial
<220> FEATURE:
<223> OTHER INFORMATION: Synthetic Oligonucleotide; ATG 1240 + S51N + S444R (amino acid sequence SEQ ID NO: 4)

<400> SEQUENCE: 10

```
atggtaaagc gtgagaaaaa tgtcatctat ggccctgagc ctctccatcc tttggaggat       60
ttgactgccg gcgaaatgct gtttcgtgct ctccgcaagc actctcattt gcctcaagcc      120
ttggtcgatg tggtcggcga tgaatctttg aactacaagg agttttttga ggcaaccgtc      180
ttgctggctc agtccctcca caattgtggc tacaagatga cgacgtcgt tagtatctgt       240 gctgaaaaca taccccgttt cttcattcca gtcatcgccg catggtatat cggtatgatc      300
gtggctccag tcaacgagag ctacattccc gacgaactgt gtaaagtcat gggtatctct      360
aagccacaga ttgtcttcac cactaagaat attctgaaca agtcctggaa gtccaaagc      420 cgcaccaact ttattaagcg tatcatcatc ttggacactg tggagaatat tcacggttgc      480
gaatctttgc ctaatttcat ctctcgctat tcagacggca acatcgcaaa ctttaaacca      540
ctccacttcg accctgtgga acaagttgca gccattctgt gtagcagcgg tactactgga      600
ctcccaaagg gagtcatgca gacccatcaa acatttgcg tgcgtctgat ccatgctctc      660
gatccacgct acggcactca gctgattcct ggtgtcaccg tcttggtcta cttgcctttc      720
ttccatgctt tcggctttca tattactttg ggttacttta tggtcggtct ccgcgtgatt      780
atgttccgcc gttttgatca ggaggctttc ttgaaagcca tccaagatta tgaagtccgc      840
agtgtcatca acgtgcctag cgtgatcctg ttttgtgtcta agagcccact cgtggacaag      900
tacgacttgt cttcactgcg tgaattgtgt tgcggtgccg ctccactggc taaggaggtc      960
```

```
gctgaagtgg ccgccaaacg cttgaatctt ccagggatta gttgtggctt cggcctcacc    1020
gaatctacca gtgcgattat ccagactctc cgggatgagt ttaagagcgg ctctttgggc    1080
cgtgtcactc cactcatggc tgctaagatc gctgatcgcg aaactggtaa ggctttgggc    1140
ccgaaccaag tgggcgagct gtgtatcaaa ggccctatgg tgagcaaggg ttatgtcaat    1200
aacgttgaag ctaccaagga ggccatcgac gacgacggct ggttgcattc tggtgatttt    1260
ggatattacg acgaagatga gcatttttac gtcgtggatc gttacaagga gctgatcaaa    1320
tacaagggtc gccaggttgc tccagctgag ttggaggaga ttctgttgaa aaatccatgc    1380
attcgcgatg tcgctgtggt cggcattcct gatctggagg ccggcgaact gccttctgct    1440
ttcgttgtca agcagcctgg tacagaaatt accgccaaag aagtgtatga ttacctggct    1500
gaacgtgtga gccatactaa gtacttgcgt ggcggcgtgc gttttgttga ctccatccct    1560
cgtaacgtaa caggcaaaat tacccgcaag gagctgttga aacaattgtt ggtgaaggcc    1620
ggcggtgttt aa                                                        1632
```

LUCIFERASE SEQUENCES UTILIZING INFRARED-EMITTING SUBSTRATES TO PRODUCE ENHANCED LUMINESCENCE

CROSS-REFERENCE TO RELATED APPLICATIONS

This application is a continuation of U.S. application Ser. No. 15/644,876 filed Jul. 10, 2017, which is a continuation of U.S. application Ser. No. 14/851,608 filed Sep. 11, 2015, now U.S. Pat. No. 9,732,373 issued Aug. 15, 2017, which claims priority to U.S. Provisional Application No. 62/049,150 filed Sep. 11, 2014, which are incorporated herein by reference in their entireties.

FIELD OF THE INVENTION

The present invention relates to an isolated polynucleotide encoding click beetle luciferase variant polypeptides that have enhanced luminescence and produce longer, near-infrared wavelength signals. The present invention also relates to near-infrared bioluminescence systems that include said click beetle luciferase variant polypeptides and infrared-emitting substrates and methods of using said click beetle luciferase variant polypeptides and near-infrared bioluminescence systems.

BACKGROUND

Bioluminescence with a longer-wavelength and lower-energy emission is of significant interest both for multiplexing applications with multiple emission colors and for in-depth tissue imaging where shorter wavelengths tend to be strongly absorbed. Many standard systems for optical imaging have limited utility in a whole-animal context due to the diminished transmission of light through biological samples. Light penetration is limited by the absorption coefficients of particular components in blood. Strong absorption by Hemoglobin (Hb) and oxygenated hemoglobin ($HbO_2$) diminish transmission and penetration depth of light through blood and animal tissues. Luminescent systems that emit light in the far-red and near-infrared region (680-900 nm) allow for optimal imaging due to the minimum absorbance spectrums of Hb and $HbO_2$. This region of maximum light penetration is known as the whole animal "optical window." Bioluminescent reporter systems have been used extensively in research animals, yet still suffer from the limitations of diminished tissue penetration. Typical bioluminescent light emission wavelengths (460-620 nm) occur in a region with limited penetration depth. The ideal bioluminescent reporter systems in whole animals would benefit greatly from the bright light emission in the region of 680-900 nm. While numerous bioluminescent systems have been modified to shift visible light emission toward the red, none have achieved a strong red emission to overlap significantly with the critical "optical window" of blood transmittance.

Previous approaches for molecular imaging in vivo include quantum dot conjugates that luminesce by bioluminescence resonance energy transfer (BRET) in the absence of external excitation. These conjugates, prepared by coupling carboxylate-presenting quantum dots to a mutant of the bioluminescent protein of *Renilla reniformis* luciferase, emit a long-wavelength (from red to near-infrared) bioluminescent light in cells and in animals, even in deep tissues. However, this approach is limited by the signal intensity for *Renilla* luciferase and by the relatively low aqueous solubility of the coelenterazine substrate. Another approach, e.g., Aka Lumine (Wako), utilizes a luciferin derivative which is dimmer and less red (675 nm) (see FIG. 19A and FIG. 19B).

Therefore, there is a need in small animal optical imaging applications for longer wavelength and lower energy-emitting near-infrared bioluminescence systems that will make it possible to detect signals from deep tissue, where standard near-infrared bioluminescence systems (450-620 nm) tend to be strongly absorbed.

SUMMARY OF THE INVENTION

The present invention is directed to an isolated polynucleotide encoding a click beetle red luciferase (CBR) variant polypeptide having at least 80% amino acid sequence identity to SEQ ID NO: 1 and comprising at least one amino acid substitution at a position corresponding to position 4, 16, 34, 47, 51, 52, 55, 72, 73, 74, 79, 82, 83, 87, 89, 104, 109, 113, 117, 119, 124, 130, 131, 133, 136, 144, 146, 156, 159, 170, 179, 186, 200, 211, 218, 224, 225, 226, 228, 229, 234, 247, 251, 252, 253, 255, 280, 281, 285, 308, 309, 310, 319, 329, 334, 335, 337, 346, 348, 349, 350, 352, 354, 355, 358, 363, 370, 377, 390, 393, 394, 400, 401, 409, 412, 420, 422, 431, 437, 439, 444, 445, 453, 455, 467, 471, 473, 479, 484, 489, 496, 501, 503, 508, 516, 528, 531, 535, 537, 539, or combination thereof, of SEQ ID NO: 1, wherein the variant CBR polypeptide has at least one of enhanced luminescence, altered light emission wavelength, altered substrate specificity, or a combination thereof, as compared to a CBR polypeptide of SEQ ID NO: 1. The CBR variant polypeptide may further comprise at least one amino acid substitution at a position corresponding to position 351, 389, 457, or combination thereof, of SEQ ID NO: 1. The CBR variant polypeptide may comprise a substitution corresponding to at least one of R4H, H16Q, H34Y, D47E, S51N, Y52C, F55L/V, K72E, I79V, M73K/T, N74S, E82G, N83H, F87S, I89V, V104D, I109N/V, L113Q, M117T, I119F/T, I124V, N130K, I131N/T, N133D, K136N, F144L, K146E, N156D, N156K, G159D, Y170C, K179S, V186A, G200G, N211N, H218L/Y, G225S, T226C/G/H/N/Q/Y, L228P, I229V, V234A, G251S, G251I, Y252C, V255D/F, E253K, R280S, S281N/Q, V285A, I309T, E319G, N329D, R334E/Q/H/S/N/K, C335S, K337E, I346N, Q348H/E, L350P, G351K/R, D352N, R355G, S358P, T363A/S, I1370T, I389F/G/S/V, I3901, M393K/L, V394M, N400D, N401S, I409T, D412G, F420F, Y422C, V431A, E437G, I439V, S444C/R/T, Q445H, E453K, V455D, K457N, D471V, E473A, S479T, K484E/M/R, E489V, Y496H, E501G, V503M, Y508C, V516A, T528A, E531G, Q535H, L537W, K539R, or combinations thereof, or SEQ ID NO: 1. The CBR variant polypeptide may comprise an amino acid substitution at a position corresponding to position 389, 444, and 251 of SEQ ID NO: 1. The amino acid substitutions may comprise 1389F, S444R, and G251S. The CBR variant polypeptide may comprise an amino acid substitution at positions corresponding to positions 334 and 351 of SEQ ID NO: 1. The amino acid substitutions may comprise R334S and G351R. The CBR variant polypeptide may further comprise an amino acid substitution at a position corresponding to positions 51 and 444 of SEQ ID NO: 1. The amino acid substitutions may comprise S51N and S444R. The CBR variant polypeptide may comprise an amino acid polypeptide of SEQ ID NO: 2, SEQ ID NO: 3, or SEQ ID NO: 4. The CBR variant polypeptide may have enhanced luminescence compared to a CBR polypeptide of SEQ ID NO: 1. The CBR variant polypeptide may have enhanced luminescence when a luciferin is utilized by the CBR variant polypeptide to generate luminescence. The CBR variant polypeptide may have enhanced luminescence when a luciferin derivative is utilized by the CBR variant polypeptide to generate luminescence. The luciferin derivative may comprise:

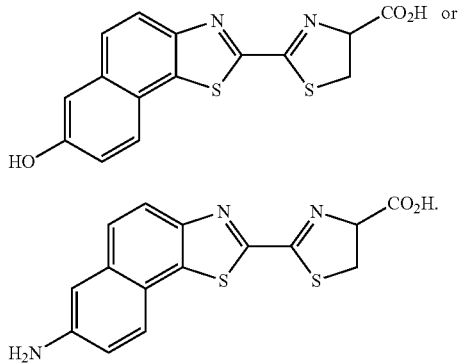

The CBR variant polypeptide may have at least 2 fold increase in luminescence compared to a CBR polypeptide of SEQ ID NO: 1. The CBR variant polypeptide may have at least 4 fold increase in luminescence compared to a CBR polypeptide of SEQ ID NO: 1. The CBR variant polypeptide may have altered light emission spectra compared to a CBR polypeptide of SEQ ID NO: 1. The CBR variant polypeptide may be able to emit light at a longer wavelength when a luciferin is utilized by the CBR variant polypeptide to generate luminescence. The CBR variant polypeptide may be able to emit light at a longer wavelength when a luciferin derivative is utilized by the CBR variant polypeptide to generate luminescence. The luciferin derivative may comprise:

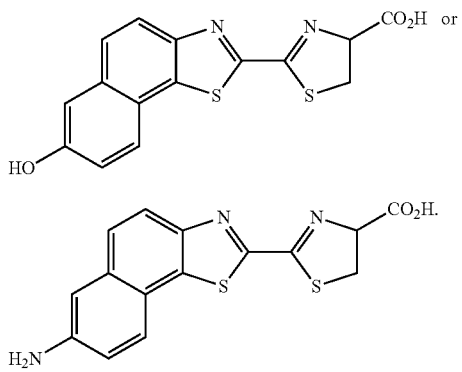

If the luciferin derivative comprises

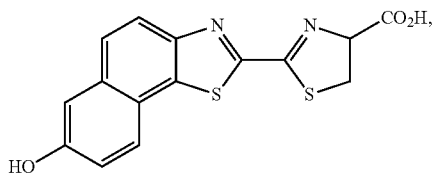

the CBR variant polypeptide may emit light having a shift in spectral maximum of at least about 1 nm to at least about 100 nm relative to the light produced by the CBR polypeptide of SEQ ID NO: 1. The CBR variant polypeptide may emit light having a spectral maximum between about 650 nm to about 800 nm. The CBR variant polypeptide may emit light having a spectral maximum between about 725 nm to about 775 nm. The CBR variant polypeptide may emit light having a spectral maximum of about 750 nm. If the luciferin derivative comprises

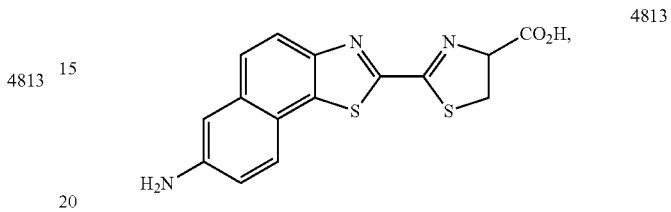

the CBR variant polypeptide may emit light having a shift in spectral maximum of at least about 1 nm to at least about 100 nm relative to the light produced by the CBR polypeptide of SEQ ID NO: 1. The CBR variant polypeptide may emit light having a shift in spectral maximum of at least about 75 nm relative to the light produced by the CBR polypeptide of SEQ ID NO: 1. The CBR variant polypeptide may emit light having a spectral maximum between about 650 nm to about 800 nm. The CBR variant polypeptide may emit light having a spectral maximum between about 700 nm to about 775 nm. The CBR variant polypeptide may emit light having a spectral maximum of about 725 nm. The CBR variant polypeptide may have altered substrate specificity compared to a CBR polypeptide of SEQ ID NO: 1. The CBR variant polypeptide may have a change in relative specificity relative to the CBR variant polypeptide in the presence of a luciferin compared to a luciferin derivative. The CBR variant polypeptide may have a change in relative specificity relative to the CBR variant polypeptide in the presence of a luciferin derivative compared to a different luciferin derivative. The luciferin derivative may comprise:

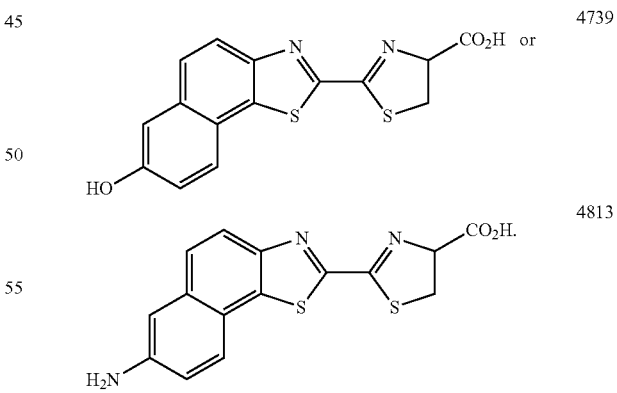

The variant CBR polypeptide may have luciferase activity. The variant CBR polypeptide may have a Km for PBI-4813 of at least about 0.01 μM to at least about 5.00 μM. The variant CBR polypeptide may have a Km for PBI-4813 of at least about 0.50 μM to at least about 3.00 μM. The variant CBR polypeptide may have a Km for PBI-4813 of at least about 0.82 μM or 2.41 μM. The variant CBR polypeptide may have a Km for PBI-4739 of at least about 0.01 µM to at least about 5.00 µM. The variant CBR polypeptide may have a Km for PBI-4739 of at least about 1.50 µM to at least about 4.50 µM. The variant CBR polypeptide may have a Km for PBI-4739 of at least about 2.33 µM or 3.95 µM. The variant CBR polypeptide may have a relative Vmax that is at least 2 fold higher than the relative Vmax of a CBR polypeptide of SEQ ID NO: 1 using PBI-4813 as a substrate. The variant CBR polypeptide may have a relative Vmax that is at least 2 fold higher than the relative Vmax of a CBR polypeptide of SEQ ID NO: 1 using PBI-4739 as a substrate. The sequence may have been codon-optimized. The sequence may comprise a polynucleotide of SEQ ID NOs: 6-9. The polynucleotide may further encode a polypeptide of interest linked to the CBR variant polypeptide, the polypeptide of interest and the CBR variant polypeptide capable of being expressed as a fusion protein. The polypeptide of interest may comprise HALOTAG®.

The present invention is directed to a vector comprising the polynucleotide, or a fragment thereof, as described above. The polynucleotide may be operably linked to a promoter.

The present invention is directed to a cell comprising the polynucleotide as described above or the vector as described above.

The present invention is directed to a non-human transgenic animal comprising the cell as described above.

The present invention is directed to a non-human transgenic animal comprising the polynucleotide as described above or the vector as described above.

The present invention is directed to a CBR variant polypeptide encoded by the polynucleotide as described above.

The present invention is directed to a circularly permuted luciferase comprising the polypeptide encoded by the polynucleotide as described above or a fragment thereof.

The present invention is directed to a fusion protein comprising a CBR variant polypeptide encoded by the polynucleotide as described above.

The present invention is directed to a near-infrared bioluminescence system comprising the polynucleotide as described above and a luciferin derivative. The luciferin derivative may comprise:

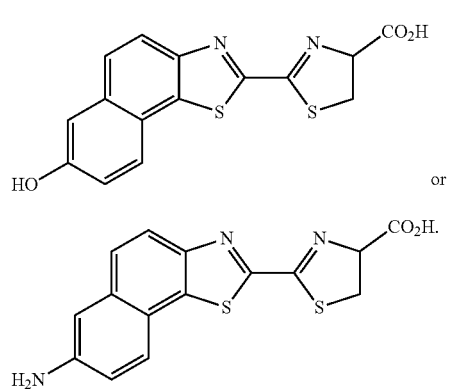

The present invention is directed to a method of producing a CBR variant polypeptide comprising growing the cell as described above under conditions that permit expression of the CBR variant polypeptide.

The present invention is directed to a method of producing a CBR variant polypeptide comprising introducing the vector as described above into a cell under conditions which permit expression of the CBR variant polypeptide.

The present invention is directed to a kit comprising the polynucleotide as described above or the vector as described above.

The present invention is directed to a kit comprising the CBR variant polypeptide as described above. The kit may further comprise at least one of:

(a)

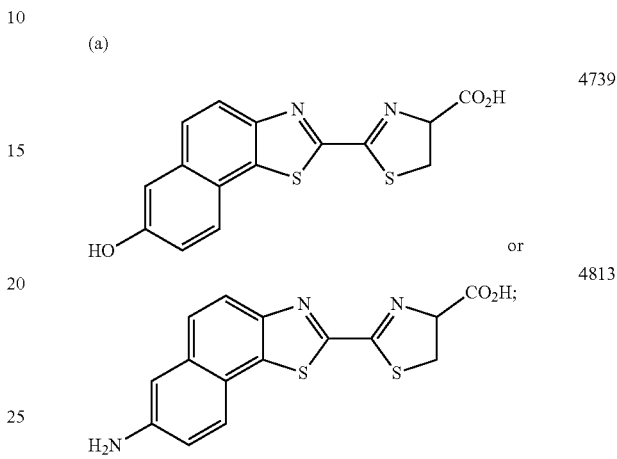

and
(b) a buffer reagent.

The present invention is directed to a bioluminescence resonance energy transfer (BRET) system comprising: a first fusion protein including a first target protein and a bioluminescence donor molecule, wherein the bioluminescence donor molecule is a CBR variant encoded by the polynucleotide as described above; a second fusion protein including a second target protein and a fluorescent acceptor molecule; and a CBR substrate. The CBR substrate may be a luciferin or luciferin derivative. The luciferin derivative may comprise:

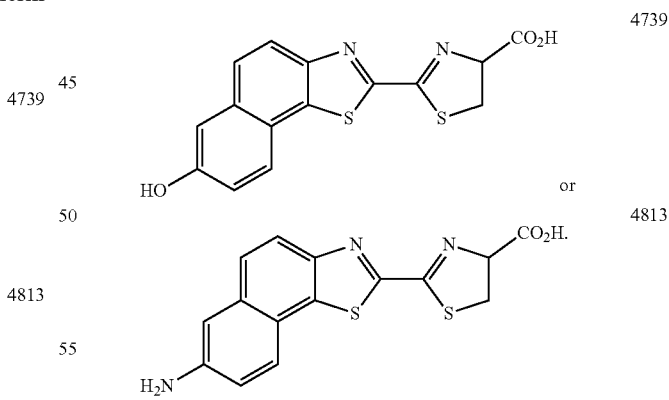

The present invention is directed to a method for measuring bioluminescence using at least one of the polynucleotide as described above; the vector as described above; the cell as described above; the animal as described above; the CBR variant polypeptide as described above; the circularly permuted luciferase as described above; the fusion protein as described above, or the near-infrared bioluminescence system as described above. The bioluminescence may be measured in a live, intact non-human animal.

The present invention is directed to a method of measuring the enzymatic activity of a luminogenic protein. The method comprises contacting a luminogenic protein, a deprotecting enzyme, and a protected luminophore; and detecting light produced from the composition, wherein the luminogenic protein is a CBR variant encoded by the polynucleotide as described above and the luminophore is a luciferin derivative comprising

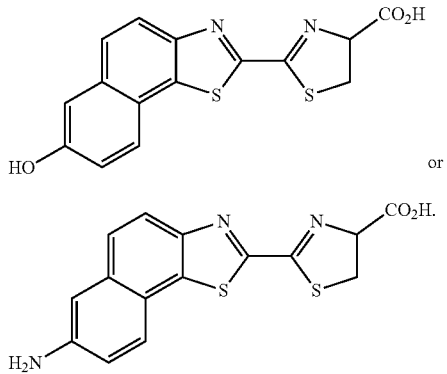

The enzymatic activity may be measured in a live, intact non-human animal.

The present invention is directed to a method for measuring the activity of a non-luminescent enzyme of interest. The method comprises (a) providing a luminogenic molecule wherein the molecule is a substrate for the non-luminescent enzyme of interest and a pro-substrate of a CBR variant encoded by the polynucleotide as described above; (b) contacting the luminogenic molecule with at least one non-luminescent enzyme of interest and at least one CBR variant to produce a reaction mixture; and (c) determining activity of the non-luminescent enzyme of interest by measuring luminescence of the reaction mixture. The luminogenic molecule may be a modification of

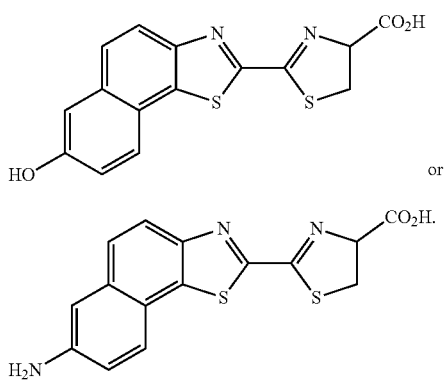

The non-luminescent enzyme of interest may be a protease enzyme, a cytochrome P450 enzyme, a monoamine oxidase enzyme, or a glutathione S-transferase enzyme. The activity of the non-luminescent enzyme may be measured in a live, intact animal.

The present invention is directed to a method to detect the presence of at least two molecules in a sample or a cell. The method comprises contacting the sample or cell with a first reporter molecule comprising a CBR variant encoded by the polynucleotide as described above, wherein the first reporter molecule is operatively linked to a first component of the sample or cell; contacting the sample with a second reporter molecule, wherein the second reporter molecule is operatively linked to a second component of the sample or cell; and detecting the presence of the first and second reporter molecules to determine the presence and/or amounts of the first and second components in the sample or cell.

The present invention is directed to a method to detect an interaction between a first protein and a second protein in a sample. The method comprises contacting a sample with:

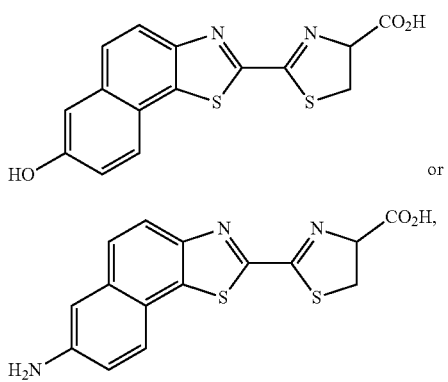

wherein the sample comprises: a first polynucleotide encoding a first fusion protein, wherein the first fusion protein comprises a first fragment of a luminescent enzyme and a first protein; and a second polynucleotide encoding a second fusion protein, wherein the second fusion protein comprises a second fragment of the luminescent enzyme and a second protein; and detecting luminescence in the sample. The detection of luminescence indicates an interaction between the first protein and the second protein, wherein the luminescent enzyme is encoded by the isolated polynucleotide as described above. When the first protein and second protein interact, the first fragment of the luminescent enzyme and the second fragment of the luminescent enzyme may reconstitute a full-length enzyme capable of stably binding the cell-permeable substrate.

The present invention is directed to a method to detect an interaction between a first protein and a second protein in a sample. The method comprises contacting a sample with:

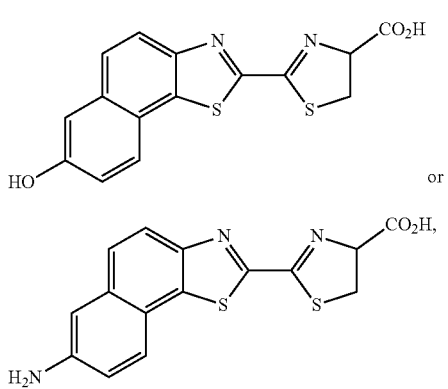

wherein the sample comprises: a first polynucleotide encoding a first fusion protein, wherein the first fusion protein comprises a luminescent enzyme and a first protein, wherein the luminescent enzyme is encoded by the isolated polynucleotide of any one of claims 1-46; and a second polynucleotide encoding a second fusion protein, wherein the second fusion protein comprises a fluorescent acceptor molecule and a second protein; and (b) detecting bioluminescence resonance energy transfer (BRET) in the sample, indicating an interaction or close proximity of the bioluminescent donor and the fluorescence acceptor.

BRIEF DESCRIPTION OF THE DRAWINGS

FIG. 1 illustrates the chemical structure of PBI-4739 and PBI-4813.

FIG. 18 illustrates the amino acid sequence of CBR with target amino acid sites for insertion mutagenesis bolded and underlined.

FIG. 19A and FIG. 19B illustrate the luminescence of CBR using Aka Lumine, PBI-4739 and PBI-4813 (FIG. 19A) and the spectral scan of QuantiLum® Recombinant Luciferase using Aka Lumine as substrate (FIG. 19B).

DETAILED DESCRIPTION

Figure 2B:
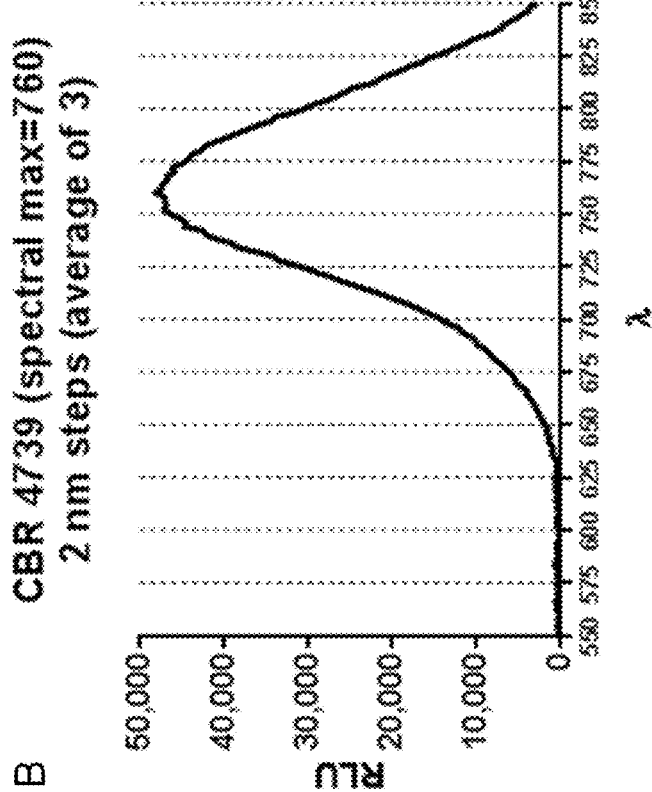
FIG. 2A and FIG. 2B illustrate spectral scans of click beetle red luciferase (CBR) using PBI-4813 (FIG. 2A) and PBI-4739 (FIG. 2B) as substrates.

Disclosed herein are click beetle red luciferase (CBR) variants that have enhanced performance in the near-infrared (near-IR) range using luciferin and/or novel luciferin derivatives. The disclosed CBR variants have enhanced performance in vitro and in living cells, e.g., increased brightness and longer wavelengths. Also disclosed herein are near-IR bioluminescence systems that comprise the CBR variants and novel luciferin derivatives. The disclosed near-IR bioluminescence systems have enhanced performance in the near-IR range and address sensitivity limitations that are related to tissue absorption and associated with other bioluminescent detections systems. Unlike other bioluminescence systems, such as VivoGlo™ (Promega Corp.), the disclosed near-IR bioluminescence systems provide near-IR luminescence signals that penetrate tissue well and provide enhanced detection of signals coming from deep animal tissues. The present disclosure also encompasses methods of using and kits including the CBR variants and/or bioluminescence systems.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The terminology used herein is for the purpose of describing particular embodiments only and is not intended to be limiting. As used in the specification and the appended claims, the singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

As used herein, "bioluminescence" or "luminescence" is light produced as a result of a reaction between an enzyme and a substrate that generates light.

In general, "enhanced" means that the particular property (e.g. bioluminescence or luminescence) is increased relative to that of a reference luciferase plus luciferin combination or luciferase under consideration, where the increase is at least 1%, at least 2%, at least 3%, at least 4%, at least 5%, at least 10%, at least 20%, at least 25%, at least 50%, at least 75%, at least 90%, at least 100%, at least 200%, at least 500%, or at least 1000% greater than the reference luciferase plus luciferin combination or luciferase under consideration.

The term "luciferin substrate" as used herein refers to a molecule capable of creating light via a chemical or biochemical reaction (e.g., luciferin, luciferin derivative, or a functional analog thereof). Suitable luciferin substrates for luciferase enzymes include luciferin, luciferin derivatives, and functional analogs of luciferins. In some embodiments, functional analogs of luciferins include modified luciferins including derivatives of these compounds. Exemplary compounds include those disclosed in U.S. patent application Ser. No. 14/200,563.

The naturally-occurring substrate for beetle luciferases is firefly luciferin, a polytherocyclic organic acid, D-(−)-2-(6'-hydroxy-2'-benzoth-iazolyl)-$\Delta^2$-thiazolin-4-carboxylic acid ("D-luciferin" also referred to as "luciferin"). Luciferin may be isolated from nature (e.g., from fireflies) or synthesized. Synthetic luciferin can have the same structure as the naturally occurring luciferin or can be derivatized, so long as it functions analogously. Examples of derivatives of luciferin include D-luciferin methyl ester and other esters of luciferase that are hydrolyzed or acted upon by esterases in a sample to yield luciferin, and naphthyl- and quinolyl-luciferin (Branchini et al., 1989). There are multiple commercial sources for luciferin (e.g., Promega Corp. Madison, Wis.).

The term "luciferin derivative" as used herein refers to a type of luminogenic molecule or compound having a substantial structure of D-luciferin and is a luciferase substrate, e.g., aminoluciferin, or luciferase substrates disclosed in U.S. Patent Publication No. 2007/0015790.

A "luciferase reaction mixture" contains a luciferase enzyme and materials that will allow the luciferase enzyme to generate a light signal. The materials needed, and the particular concentrations and/or amounts, of the materials needed to generate a luminescent signal will vary depending on the luciferase enzyme used as well as the type of luciferase-based assay being performed. In general, for click beetle luciferase, including the CBR variants, these materials can include: ATP, magnesium (Mg2+) salt, such as magnesium sulfate, a click beetle luciferase enzyme, and a luciferin or novel luciferin derivative capable of generating light when the luciferin or novel luciferin derivative is used as a substrate for the click beetle luciferase. Often other materials will be added to the solution including: a buffer to maintain the reaction at the proper pH, an additive such as PRIONEX or Bovine serum albumin (BSA) to help maintain luciferase activity, reducing agents, detergents, esterases, salts, amino acids, e.g. D-cysteine, etc. An example luciferase reaction mixture would contain a click beetle luciferase, $MgSO_4$, ATP, Tergitol NP-9, and Tricine.

A "luciferase detection mixture" contains materials that will allow for the detection of a luciferase enzyme. The materials needed, and the particular concentrations and/or amounts, of the materials needed to generate a luminescent signal will vary depending on the luciferase enzyme used as well as the type of luciferase-based assay being performed. In general, for click beetle luciferase, including the CBR variants disclosed herein, these materials can include: ATP, magnesium (Mg2+) salt, such as magnesium sulfate, and a luciferase substrate, e.g., luciferin, luciferin derivative, functional analog, or novel luciferin derivative capable of generating light when the luciferase substrate, e.g., luciferin, luciferin derivative, functional analog, or novel luciferin derivative is used as a substrate for the click beetle luciferase. Often other materials will be added to the solution including: a buffer to maintain the reaction at the proper pH, an additive such as PRIONEX or Bovine serum albumin (BSA) to help maintain luciferase activity, reducing agents, detergents, esterases, salts, amino acids, e.g. D-cysteine, etc. An example luciferase detection mixture would contain a luciferase substrate, $MgSO_4$, ATP, Tergitol NP-9, and Tricine.

The term "luminescence" refers to the light output of the luciferase, e.g., the CBR variant, under appropriate conditions, e.g. in the presence of a suitable substrate such as a luciferin or novel luciferin derivative. The light output may be measured as an instantaneous or near-instantaneous measure of light output (which is sometimes referred to as "T=0" luminescence or "flash") at the start of the luminescence reaction, which may be initiated upon addition of the luciferin or novel luciferin derivative substrate. The luminescence reaction in various embodiments is carried out in a solution. In other embodiments, the luminescence reaction is carried out on a solid support. The solution may contain a lysate, for example from the cells in a prokaryotic or eukaryotic expression system. In other embodiments, expression occurs in a cell-free system, or the luciferase protein is secreted into an extracellular medium, such that, in the latter case, it is not necessary to produce a lysate. In some embodiments, the reaction is started by injecting appropriate materials, e.g. luciferin substrate, buffer, etc., into a reaction chamber (e.g. a well of a multiwell plate such as a 96-well plate) containing the luminescent protein. In still other embodiments, the luciferase substrate is introduced into a host, which may be expressing a luciferase, e.g., a CBR variant, and measurements of luminescence are made on the host or a portion thereof, which can include a whole organism or cells, tissues, explants, or extracts thereof. The reaction chamber may be situated in a reading device which can measure the light output, e.g. using a luminometer or photomultiplier. The light output or luminescence may also be measured over time, for example in the same reaction chamber for a period of seconds, minutes, hours, etc. The light output or luminescence may be reported as the average over time, the half-life of decay of signal, the sum of the signal over a period of time, or the peak output. Luminescence may be measured in Relative Light Units (RLUs).

"Relative substrate specificity" is determined by dividing the luminescence of a luciferase in the presence of a test luciferin substrate by the luminescence of the luciferase in the presence of a reference luciferin substrate. For example, relative specificity may be determined by dividing the luminescence of a luciferase with a novel luciferin derivative by the luminescence of the luciferase with a different luciferin (e.g. D-luciferin or novel luciferin derivative). The test luciferin substrate and the reference luciferin substrate that are compared are considered a comparison substrate pair for determining relative substrate specificity.

A "change in relative substrate specificity" is determined by dividing the relative substrate specificity of a test luciferase using a comparison substrate pair by the relative substrate specificity of a reference luciferase using the same comparison substrate pair. For example, a change in relative specificity may be determined by dividing the relative substrate specificity of a test luciferase with a novel luciferin derivative compared to a different luciferin (e.g. D-luciferin or novel luciferin derivative), by the relative substrate specificity of a reference luciferase with the same novel luciferin derivative compared to the same different luciferin used for the test luciferase.

The term "fusion polypeptide" or "fusion protein" refers to a chimeric protein containing a reference protein (e.g., CBR variant) joined at the N- and/or C-terminus to one or more heterologous sequences (e.g., a non-CBR polypeptide).

The term "identity," in the context of two or more nucleic acids or polypeptide sequences, refers to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection. Methods of alignment of sequence for comparison are well-known in the art. Optimal alignment of sequences for comparison can be conducted by the algorithm of Smith et al., (*J. Mol. Biol.* 147:195-197 (1981)), by the homology alignment algorithm of Needleman and Wunsch, (*J. Mol. Biol.*, 48:443-453 (1970)), by the search for similarity method of Pearson and Lipman, (*Proc. Natl. Acad. Sci. USA,* 85:2444-2448 (1988)), by computerized implementations of algorithms e.g., FASTA, S SEARCH, GGSEARCH (available at the University of Virginia FASTA server by William R. Pearson fasta.bioch.virginia.edu/fasta_www2/fasta_intro.shtml), the Clustal series of programs (Chenna et al., *Nucl. Acids Res.* 31(13):3497-3500 (2003); available examples at www.ebi.ac.uk or www.ch.embnet.org), or other sequence analysis software. It is known in the art that generating alignments with maximum correspondence between polypeptide sequences with significant sequence alterations (e.g. altered domain order, missing/added domains, repeated domains, shuffled domains, circular permutation) may involve the use of specialized methods, such as the ABA method (Raphael et al., *Genome Res.* 14(11): 2336-2346 (2004)), other suitable methods, or performing the alignment with two concatenated identical copies of the polypeptide sequences.

Nucleic acids are known to contain different types of "mutations", which refers to an alteration in the sequence of a nucleotide at a particular base position relative to the wild-type sequence. Mutations may also refer to insertion or deletion of one or more bases so that the nucleic acid sequence differs from a reference, e.g., a wild-type sequence, or replacement with a stop codon. A "substitution" refers to a change in an amino acid at a particular position in a sequence.

The term "nucleic acid molecule," "polynucleotide" or "nucleic acid sequence" as used herein, refers to nucleic acid, including DNA or RNA, that comprises coding sequences necessary for the production of a polypeptide or protein precursor. The encoded polypeptide may be a full-length polypeptide, a fragment thereof (less than full-length), or a fusion of either the full-length polypeptide or fragment thereof with another polypeptide, yielding a fusion polypeptide.

A polynucleotide encoding a protein or polypeptide means a nucleic acid sequence comprising the coding region of a gene, or in other words, the nucleic acid sequence encoding a gene product. The coding region may be present in a cDNA, genomic DNA or RNA form. When present in a DNA form, the oligonucleotide may be single stranded (e.g., the sense strand) or double stranded. Suitable control elements such as enhancers/promoters, splice junctions, polyadenylation signals, etc. may be placed in close proximity to the coding region of the gene, if needed, to permit proper initiation of transcription and/or correct processing of the primary RNA transcript. Other control or regulatory elements include, but are not limited to, transcription factor binding sites, splicing signals, polyadenylation signals, termination signals and enhancer elements.

By "peptide," "protein" and "polypeptide" is meant amino acid chains of varying lengths, regardless of post-translational modification (e.g., glycosylation or phosphorylation). The nucleic acid molecules of the invention encode a variant of a man-made (i.e. synthetic) variant protein or polypeptide fragment thereof, which has an amino acid sequence that is at least 60%, e.g., at least 65%, 70%, 75%, 80%, 85%, 90%, 95%, 96%, 97%, 98%, 99%, or 100%, amino acid sequence identity to the amino acid sequence of the parental protein from which it is derived, where the parental protein can be a naturally-occurring (native or wild-type) sequence or a variant sequence which is subsequently modified further.

As used herein, "pure" or "purified" means an object species is the predominant species present (i.e., on a molar and/or mass basis, it is more abundant than any other individual species, apart from water, solvents, buffers, or other common components of an aqueous system in the composition), and, in some embodiments, a purified fraction is a composition wherein the object species comprises at least about 50% (on a molar basis) of all macromolecular species present. Generally, a "substantially pure" composition will comprise more than about 80% of all macromolecular species present in the composition, in some embodiments more than about 85%, more than about 90%, more than about 95%, or more than about 99%. In some embodiments, the object species is purified to essential homogeneity (contaminant species cannot be detected in the composition by conventional detection methods) wherein the composition consists essentially of a single macromolecular species.

The term "variant" refers to a modified version of a starting polypeptide or polynucleotide sequence. The term "parental" is a relative term that refers to a starting sequence which is then modified. The parental sequence is generally used as a reference for the protein encoded by the resulting modified sequence, e.g. to compare the activity levels or other properties of the proteins encoded by the parental and the modified sequences. The starting sequence can be a naturally-occurring (i.e. native or wild-type) sequence. The starting sequence can also be a variant sequence which is then further modified. A polypeptide sequence is "modified" when one or more amino acids (which may be naturally-occurring or synthetic) are substituted, deleted, and/or added at the beginning, middle, i.e., at an internal position, and/or end of the sequence. A polynucleotide sequence is "modified" when one or more nucleotides are substituted, deleted, and/or added at the beginning, middle, i.e., at an internal position, and/or end of the sequence, but which may or may not alter the amino acid encoded by the sequence. In some embodiments, the modifications produce a variant that is a functional fragment of CBR or a particular CBR variant. A functional fragment is a fragment which is less than a full-length parental sequence which has the same functional activity as the full-length parental sequence. Functional activity is the ability to exhibit luminescence. In some embodiments, the modifications produce a variant that is a permuted sequence of the parental sequence, such as a circularly permuted sequence and permuted sequences comprising deletions and/or insertions.

Variant is also used herein to describe a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree, and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function.

Substitution of amino acids having similar hydrophilicity values can result in peptides retaining biological activity as is understood in the art. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties. "Variant" also can be used to describe a polypeptide or a fragment thereof that has been differentially processed, such as by proteolysis, phosphorylation, or other post-translational modification, yet retains its biological activity.

The term "vector" refers to nucleic acid molecules into which fragments of DNA may be inserted or cloned and can be used to transfer DNA segment(s) into a cell and capable of replication in a cell. Vectors may be derived from plasmids, bacteriophages, viruses, cosmids, and the like.

The term "wild-type" or "native" as used herein refers to a gene or gene product that has the characteristics of that gene or gene product isolated from a naturally occurring source. A wild-type gene is that which is most frequently observed in a population and is thus arbitrarily designated the "wild-type" form of the gene. In contrast, the term "mutant" refers to a gene or gene product that displays modifications in sequence and/or functional properties (i.e., altered characteristics) when compared to the wild-type gene or gene product. It is noted that naturally occurring mutants can be isolated; these are identified by the fact that they have altered characteristics when compared to the wild-type gene or gene product.

2. CBR Variants

The present disclosure provides variants of click beetle red luciferase (CBR) that utilize luciferin and luciferin derivatives and produce longer near-IR (NIR) wavelength signals. Various techniques described herein were used to evolve CBR to produce brighter light output with extended conjugation luciferins and to identify sites for amino acid substitution to produce an improved synthetic CBR polypeptide. It was found that making one or more amino acid substitutions, either alone or in various combinations, produced synthetic CBR-type polypeptides having enhanced luminescence (e.g., enhanced brightness) and longer wavelength emissions. Also provided is a polynucleotide encoding a CBR variant of the invention or a fusion thereof, an isolated host cell having the polynucleotide or the CBR variant or a fusion thereof, and methods of using the polynucleotide, CBR variant or a fusion thereof or host cell of the invention.

The CBR variants have at least one amino acid substitution at a position corresponding to position 4, 16, 34, 47, 51, 52, 55, 72, 73, 74, 79, 82, 83, 87, 89, 104, 109, 113, 117, 119, 124, 130, 131, 133, 136, 144, 146, 156, 159, 170, 179, 186, 200, 211, 218, 224, 225, 226, 228, 229, 234, 247, 251, 252, 253, 255, 280, 281, 285, 308, 309, 310, 319, 329, 334, 335, 337, 346, 348, 349, 350, 352, 354, 355, 358, 363, 370, 377, 390, 393, 394, 400, 401, 409, 412, 420, 422, 431, 437, 439, 444, 445, 453, 455, 467, 471, 473, 479, 484, 489, 496, 501, 503, 508, 516, 528, 531, 535, 537, 539, or a combination thereof, of SEQ ID NO: 1. The CBR variants may further include at least one amino acid substitution at a position corresponding to position 351, 389, 457, or a combination thereof, of SEQ ID NO: 1. The CBR variants may have at least one amino acid substitution of corresponding to at least one of R4H, H16Q, H34Y, D47E, S51N, Y52C, F55L/V, K72E, I79V, M73K/T, N74S, E82G, N83H, F87S, I89V, V104D, I109N/V, L113Q, M117T, I119F/T, I124V, N130K, I131N/T, N133D, K136N, F144L, K146E, N156D, N156K, G159D, Y170C, K179S, V186A, G200G, N211N, H218L/Y, G225S, T226C/G/H/N/Q/Y, L228P, I229V, V234A, G251 S, G251I, Y252C, V255D/F, E253K, R280S, S281N/Q, V285A, I309T, E319G, N329D, R334E/Q/H/S/N/K, C335S, K337E, I346N, Q348H/E, L350P, G351K/R, D352N, R355G, S358P, T363A/S, I370T, I1389F/G/S/V, I1390I, M393K/L, V394M, N400D, N401S, I409T, D412G, F420F, Y422C, V431A, E437G, I439V, S444C/R/T, Q445H, E453K, V455D, K457N, D471V, E473A, S479T, K484E/M/R, E489V, Y496H, E501G, V503M, Y508C, V516A, T528A, E531G, Q535H, L537W, K539R, or combinations thereof, of SEQ ID NO: 1. The CBR variant polypeptide may have an amino acid substitution at a position corresponding to positions 389, 444, and 251 of SEQ ID NO: 1. The amino acid substitutions may include I389F, S444R, and G251S. The CBR variant polypeptide may have an amino acid substitution at a position corresponding to positions 334 and 351 of SEQ ID NO: 1. The amino acid substitutions may include R334S and G351R. The CBR variant may comprise an amino acid polypeptide of SEQ ID NO: 2 or SEQ ID NO: 3.

Several of the CBR variants and parental CBR disclosed herein have been assigned shorthand names to facilitate discussion. The term "ATG 343" (also referred to as "343" and "pF4Ag-CBR") refers to a CBR polypeptide sequence of SEQ ID NO: 1. The CBR polypeptide sequence of SEQ ID NO: 1 is encoded by the polynucleotide sequence of SEQ ID NO: 5. The term "ATG 685" (also referred to as "685" and "pF4Ag-HT7-CBR") refers to a CBR polypeptide sequence of SEQ ID NO: 1 fused to HALOTAG®. The term "ATG 1230" (SEQ ID NO: 3) refers to a CBR variant having the amino acid substitutions I389F, S444R, and G251S relative to SEQ ID NO: 1 (where the format "x #y" indicates a parent amino acid 'x' at a position '#' that is changed to variant amino acid 'y'). The term "ATG 1240" (SEQ ID NO: 2) refers to a CBR variant having the amino acid substitutions R334S and G351R relative to SEQ ID NO: 1. The term "ATG 1240+S51N+S444R" (SEQ ID NO: 4) refers to a CBR variant having the amino acid substitutions of ATG 1240, i.e., R334S and G351R of SEQ ID NO: 1, as well as amino acid substitutions S51N and S444R relative to SEQ ID NO: 1.

The sequences of a CBR variant are substantially the same as the amino acid sequence of a corresponding parental CBR, e.g., SEQ ID NO: 1. A polypeptide or peptide having substantially the same sequence means that an amino acid sequence is largely, but is not entirely, the same and retains the functional activity of the sequence to which it is related. In general, two amino acid sequences are substantially the same if they are at least 60%, e.g., at least 65%, 70%, 75%, 80%, 85%, 90%, 95%, 96%, 97%, 98%, or 99%, but less than 100%, amino acid sequence identity. In some embodiments, the CBR variant is encoded by a recombinant polynucleotide.

In some embodiments, the CBR variant has at least 60%, e.g., at least 65%, 70%, 75%, 80%, 85%, 90%, 95%, 96%, 97%, 98%, or 99%, or 100%, amino acid sequence identity to SEQ ID NOs: 1, 2, 3, or 4. Ordinarily, variant fragments are at least about 50 amino acids in length, often at least about 60 amino acids in length, more often at least about 70, 80, 90, 100, 150, 200, 300, 400, 500 or 550 amino acids in length, or more and retain the ability to generate luminescence. A full length luciferase, fragment thereof, or variant thereof may be fused to heterologous amino acid sequences and still be functional in the invention.

These CBR variants display at least one of: enhanced luminescence (including increased brightness, enhanced signal stability, signal duration, and/or decreased sensitivity to substrate inhibition); altered light emission spectra; and altered substrate specificity (i.e., change in relative substrate specificity). In various embodiments, the present invention encompasses novel luciferases that are present in solution as soluble proteins, chemically linked to other molecules (e.g., fusion proteins), or attached onto a solid surface (e.g., particles, capillaries, or assay tubes or plates).

a. Enhanced Luminescence

The enhanced luminescence of a CBR variant may be due to one or more of the following characteristics: enhanced light output (i.e. brightness), enhanced substrate specificity, enhanced signal stability, enhanced signal duration, and/or decreased sensitivity to substrate inhibition. Enhanced signal stability includes an increase in how long the signal from a luciferase continues to luminesce, for example, as measured by the half-life of decay of the signal in a time-course. The term "substrate inhibition" as used herein refers to the inhibition of luciferase enzyme activity (e.g., inhibition of generating luminescence and lower RLU values) at high concentration levels of substrate. A CBR variant having decreased sensitivity to substrate inhibition does not have lower RLU values with increasing amounts of substrate. For example, PBI-4813 at concentrations greater than ten times the Km inhibits the activity of CBR and ATG1230, thus the luminescence generated, i.e., RLU values, is decreased, whereas ATG1240 does not show this inhibition with PBI-4813 and has decreased sensitivity to substrate inhibition.

Enhanced luminescence may be determined relative to the comparable property of a luciferase such as wild-type CBR, a CBR variant protein, *Renilla* luciferase (e.g., hRluc), or firefly luciferase (e.g., Luc2; luciferase from *Photinus pyralis*) combined with a native, known, or novel substrate, as shown in the Examples below. For example, the luminescence of a given CBR variant in combination with a particular luciferin (including native, known, or novel luciferin, or derivatives thereof) may be compared to the properties of CBR combined with any of a native, known, or novel luciferins or derivatives thereof disclosed herein, using one or more of the assays disclosed in the Examples below. In particular, enhanced luminescence may be determined by measuring the luminescence signal (RLU) resulting from the incubation of bacterial or mammalian lysates containing CBR variants in question with the luciferase substrate, e.g., a novel luciferin derivative such as PBI-4813 or PBI-4739. The luminescence signal may be compared to that of a reference point such as CBR with D-luciferin or a luciferin derivative such as PBI-4813 or PBI-4739, or Luc2 (firefly) luciferase with D-luciferin.

In certain embodiments, the CBR variant has increased luminescence emission, e.g., at least about 1-fold, at least about 2-fold, at least about 3-fold, at least about 4-fold, at least about 5-fold, at least about 6-fold, at least about 7-fold, at least about 8-fold, at least about 9-fold, or at least about 10-fold in a prokaryotic cell and/or a eukaryotic cell relative to the corresponding reference luciferase, such as a CBR of SEQ ID NO: 1, using the same or different substrate, such as D-luciferin, PBI-4813 or PBI-4739. In some embodiments, one or more properties of the CBR variant are compared to comparable properties of a luciferase from another species, e.g. a firefly luciferase or a *Renilla* luciferase.

b. Altered Light Emission Spectra

The CBR variant polypeptide may have altered light emission spectra compared to a parental CBR, e.g., SEQ ID NO: 1. The CBR variant polypeptide may be able to emit light at a longer wavelength when a luciferin is utilized by the CBR variant polypeptide to generate luminescence. The CBR variant polypeptide is able to emit light at a longer wavelength when a luciferin derivative, such as PBI-4813 or PBI-4739, is utilized by the CBR variant polypeptide to generate luminescence.

The CBR variant polypeptide may emit light having a shift in spectral maximum relative to the light produced by the CBR polypeptide of SEQ ID NO: 1 using a luciferin or novel luciferin derivative such as PBI-4813 or PBI-4739. In some embodiments, the CBR variant polypeptide may emit light having an increased or decreased shift in spectral maximum of at least about 1 nm to at least about 200 nm, at least about 2 nm to at least about 200 nm, at least about 3 nm to at least about 200 nm, at least about 4 nm to at least about 200 nm, at least about 5 nm to at least about 200 nm, at least about 6 nm to at least about 200 nm, at least about 7 nm to at least about 200 nm, at least about 8 nm to at least about 200 nm, at least about 9 nm to at least about 200 nm, at least about 10 nm to at least about 200 nm, at least about 15 nm to at least about 200 nm, at least about 20 nm to at least about 200 nm, at least about 30 nm to at least about 200 nm, at least about 40 nm to at least about 200 nm, at least about 50 nm to at least about 200 nm, at least about 60 nm to at least about 200 nm, at least about 70 nm to at least about 200 nm, at least about 80 nm to at least about 200 nm, at least about 90 nm to at least about 200 nm, at least about 100 nm to at least about 200 nm, at least about 150 nm to at least about 200 nm, at least about 1 nm to at least about 150 nm, at least about 2 nm to at least about 150 nm, at least about 3 nm to at least about 150 nm, at least about 4 nm to at least about 150 nm, at least about 5 nm to at least about 150 nm, at least about 6 nm to at least about 150 nm, at least about 7 nm to at least about 150 nm, at least about 8 nm to at least about 150 nm, at least about 9 nm to at least about 150 nm, at least about 10 nm to at least about 150 nm, at least about 15 nm to at least about 150 nm, at least about 20 nm to at least about 150 nm, at least about 30 nm to at least about 150 nm, at least about 40 nm to at least about 150 nm, at least about 50 nm to at least about 150 nm, at least about 60 nm to at least about 150 nm, at least about 70 nm to at least about 150 nm, at least about 80 nm to at least about 150 nm, at least about 90 nm to at least about 150 nm, at least about 100 nm to at least about 150 nm, at least about 1 nm to at least about 100 nm, at least about 2 nm to at least about 100 nm, at least about 3 nm to at least about 100 nm, at least about 4 nm to at least about 100 nm, at least about 5 nm to at least about 100 nm, at least about 6 nm to at least about 100 nm, at least about 7 nm to at least about 100 nm, at least about 8 nm to at least about 100 nm, at least about 9 nm to at least about 100 nm, at least about 10 nm to at least about 100 nm, at least about 15 nm to at least about 100 nm, at least about 20 nm to at least about 100 nm, at least about 30 nm to at least about 100 nm, at least about 40 nm to at least about 100 nm, at least about 50 nm to at least about 100 nm, at least about 60 nm to at least about 100 nm, at least about 70 nm to at least about 100 nm, at least about 80 nm to at least about 100 nm, at least about 90 nm to at least about 100 nm, at least about 1 nm to at least about 70 nm, at least about 2 nm to at least about 70 nm, at least about 3 nm to at least about 70 nm, at least about 4 nm to at least about 70 nm, at least about 5 nm to at least about 70 nm, at least about 6 nm to at least about 70 nm, at least about 7 nm to at least about 70 nm, at least about 8 nm to at least about 70 nm, at least about 9 nm to at least about 70 nm, at least about 10 nm to at least about 70 nm, at least about 15 nm to at least about 70 nm, at least about 20 nm to at least about 70 nm, at least about 30 nm to at least about 70 nm, at least about 40 nm to at least about 70 nm, at least about 50 nm to at least about 70 nm, at least about 60 nm to at least about 70 nm, at least about 1 nm to at least about 50 nm, at least about 2 nm to at least about 50 nm, at least about 3 nm to at least about 50 nm, at least about 4 nm to at least about 50 nm, at least about 5 nm to at least about 50 nm, at least about 6 nm to at least about 50 nm, at least about 7 nm to at least about 50 nm, at least about 8 nm to at least about 50 nm, at least about 9 nm to at least about 50 nm, at least about 10 nm to at least about 50 nm, at least about 15 nm to at least about 50 nm, at least about 20 nm to at least about 50 nm, at least about 30 nm to at least about 50 nm, at least about 40 nm to at least about 50 nm, at least about 1 nm to at least about 20 nm, at least about 2 nm to at least about 20 nm, at least about 3 nm to at least about 20 nm, at least about 4 nm to at least about 20 nm, at least about 5 nm to at least about 20 nm, at least about 6 nm to at least about 20 nm, at least about 7 nm to at least about 20 nm, at least about 8 nm to at least about 20 nm, at least about 9 nm to at least about 20 nm, at least about 10 nm to at least about 20 nm, or at least about 15 nm to at least about 20 nm, relative to the light produced by the CBR polypeptide of SEQ ID NO: 1. The CBR variant polypeptide may emit light having an increased or decreased shift in spectral maximum of at least about 1 nm, at least about 2 nm, at least about 3 nm, at least about 4 nm, at least about 5 nm, at least about 6 nm, at least about 7 nm, at least about 8 nm, at least about 9 nm, at least about 10 nm, at least about 15 nm, at least about 20 nm, at least about 30 nm, at least about 40 nm, at least about 50 nm, at least about 60 nm, at least about 70 nm, at least about 80 nm, at least about 90 nm, at least about 100 nm, at least about 150 nm, or at least about 200 nm relative to the light produced by the CBR polypeptide of SEQ ID NO: 1.

The CBR variant polypeptide may emit light having a spectral maximum between about 650 nm to about 1000 nm, between about 700 nm to about 1000 nm, between about 725 nm to about 1000 nm, between about 750 nm to about 1000 nm, between about 775 nm to about 1000 nm, between about 800 nm to about 1000 nm, between about 850 nm to about 1000 nm, between about 900 nm to about 1000 nm, between about 950 nm to about 1000 nm, about 650 nm to about 900 nm, between about 700 nm to about 900 nm, between about 725 nm to about 900 nm, between about 750 nm to about 900 nm, between about 775 nm to about 900 nm, between about 800 nm to about 900 nm, between about 850 nm to about 900 nm, about 650 nm to about 800 nm, between about 700 nm to about 800 nm, between about 725 nm to about 800 nm, between about 750 nm to about 800 nm, between about 775 nm to about 800 nm, about 650 nm to about 775 nm, between about 700 nm to about 775 nm, between about 725 nm to about 775 nm, between about 750 nm to about 775 nm, between about 650 nm to about 750 nm, between about 700 nm to about 750 nm, between about 725 nm to about 750 nm, between about 650 nm to about 725 nm, between about 700 nm to about 725 nm, or between about 725 nm to about 750 nm when a luciferin or novel luciferin derivative, such as PBI-4813 or PBI-4739, is used as a substrate. The CBR variant polypeptide may emit light having a spectral maximum of at least about 600 nm, at least about 650 nm, at least about 700 nm, at least about 725 nm, at least about 750 nm, at least about 775 nm, at least about 800 nm, at least about 900 nm, or at least about 1000 nm when a luciferin or novel luciferin derivative, such as PBI-4813 or PBI-4739, is used as a substrate.

c. Altered Substrate Specificity

The CBR variant polypeptide may have altered substrate specificity compared to a CBR polypeptide of SEQ ID NO: 1. The CBR variant polypeptide may have increased or decreased substrate specificity for a luciferin or novel luciferin derivative such as PBI-4739 or PBI-4813, compared to a CBR polypeptide of SEQ ID NO: 1. The CBR variant polypeptide may have a change, such as an increase or decrease, in relative specificity relative to the CBR variant polypeptide in the presence of a luciferin compared to a luciferin derivative, such as PBI-4739 or PBI-4813. The CBR variant polypeptide may have a change, such as an increase or decrease, in relative specificity relative to the CBR variant polypeptide in the presence of a luciferin derivative compared to a different luciferin derivative, such as PBI-4739 or PBI-4813.

The CBR variant polypeptide may have an altered Km or Vmax compared to a CBR polypeptide of SEQ ID NO: 1 using D-luciferin and/or a novel luciferin derivative. A CBR variant polypeptide having a lower Km for a particular substrate may be an advantage in in vivo imaging where it is difficult to "saturate" the substrate.

The CBR variant may have a Km for PBI-4813 of at least about 0.10 μM, at least about 0.20 μM, at least about 0.30

μM, at least about 0.40 μM, at least about 0.50 μM, at least about 0.60 μM, at least about 0.70 μM, at least about 0.80 μM, at least about 0.81 μM, at least about 0.82 μM, at least about 0.83 μM, at least about 0.84 μM, at least about 0.85 μM, at least about 0.86 μM, at least about 0.87 μM, at least about 0.88 μM, at least about 0.89 μM, at least about 0.90 μM, at least about 1.00 μM, at least about 1.50 μM, at least about 2.00 μM, at least about 2.10 μM, at least about 2.20 μM, at least about 2.30 μM, at least about 2.40 μM, at least about 2.50 μM, at least about 2.60 μM, at least about 2.70 μM, at least about 2.80 μM, at least about 2.90 μM, at least about 3.00 μM, at least about 4.00 μM, or at least about 5.00 μM, or has a Km ranging from at least about 0.01 μM to at least about 5.00 μM, at least about 0.01 μM to at least about 4.00 μM, at least about 0.01 μM to at least about 3.00 μM, at least about 0.01 μM to at least about 2.50 μM, at least about 0.01 μM to at least about 2.00 μM, at least about 0.01 μM to at least about 1.00 μM, at least about 0.01 μM to at least about 0.80 μM, at least about 0.01 μM to at least about 0.50 μM, at least about 0.05 μM to at least about 5.00 μM, at least about 0.05 μM to at least about 4.00 μM, at least about 0.05 μM to at least about 3.00 μM, at least about 0.05 μM to at least about 2.50 μM, at least about 0.05 μM to at least about 2.00 μM, at least about 0.05 μM to at least about 1.00 μM, at least about 0.05 μM to at least about 0.80 μM, at least about 0.08 μM to at least about 5.00 μM, at least about 0.08 μM to at least about 4.00 μM, at least about 0.08 μM to at least about 3.00 μM, at least about 0.08 μM to at least about 2.50 μM, at least about 0.08 μM to at least about 2.00 μM, or at least about 0.08 μM to at least about 1.00 μM.

The CBR variant may have a Km for PBI-4739 of at least about or has a Km ranging from at least about 0.10 μM, at least about 0.50 μM, at least about 1.00 μM, at least about 1.50 μM, at least about 2.00 μM, at least about 2.10 μM, at least about 2.20 μM, at least about 2.30 μM, at least about 2.40 μM, at least about 2.50 μM, at least about 2.60 μM, at least about 2.70 μM, at least about 2.80 μM, at least about 2.90 μM, at least about 3.00 μM, at least about 3.10 μM, at least about 3.20 μM, at least about 3.30 μM, at least about 3.40 μM, at least about 3.50 μM, at least about 3.60 μM, at least about 3.70 μM, at least about 3.80 μM, at least about 3.90 μM, at least about 4.00 μM, or at least about 5.00 μM, or has a Km ranging from at least about 0.01 μM to at least about 5.00 μM, at least about 0.01 μM to at least about 4.00 μM, at least about 0.01 μM to at least about 3.00 μM, at least about 0.01 μM to at least about 2.50 μM, at least about 0.01 μM to at least about 2.00 μM, at least about 0.01 μM to at least about 1.00 μM, at least about 0.01 μM to at least about 0.80 μM, at least about 0.01 μM to at least about 0.50 μM, 1.00 μM to at least about 5.00 μM, at least about 1.00 μM to at least about 4.00 μM, at least about 1.00 μM to at least about 3.00 μM, at least about 1.00 μM to at least about 2.50 μM, at least about 1.00 μM to at least about 2.00 μM, 2.00 μM to at least about 5.00 μM, at least about 2.00 μM to at least about 4.00 μM, at least about 2.00 μM to at least about 3.00 μM, at least about 2.00 μM to at least about 2.50 μM, 3.00 μM to at least about 5.00 μM, or at least about 3.00 μM to at least about 4.00 μM.

The CBR variant may have a Km for PBI-4813 that is at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 30-fold, at least about 4-fold, at least about 50-fold, at least about 60-fold, at least about 70-fold, at least about 80-fold, at least about 90-fold, at least about 100-fold lower, at least about 150-fold, at least about 200-fold, at least about 300-fold, at least about 400-fold, at least about 500-fold, or at least about 1000-fold lower than the Km of a CBR polypeptide of SEQ ID NO: 1 for PBI-4813.

The CBR variant may have a Km for PBI-4813 that is at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 30-fold, at least about 4-fold, at least about 50-fold, at least about 60-fold, at least about 70-fold, at least about 80-fold, at least about 90-fold, at least about 100-fold lower, at least about 150-fold, at least about 200-fold, at least about 300-fold, at least about 400-fold, at least about 500-fold, or at least about 1000-fold lower than the Km of a CBR polypeptide of SEQ ID NO: 1 for D-luciferin.

The CBR variant may have a Km for PBI-4739 that is at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 30-fold, at least about 4-fold, at least about 50-fold, at least about 60-fold, at least about 70-fold, at least about 80-fold, at least about 90-fold, at least about 100-fold lower, at least about 150-fold, at least about 200-fold, at least about 300-fold, at least about 400-fold, at least about 500-fold, or at least about 1000-fold lower than the Km of a CBR polypeptide of SEQ ID NO: 1 for PBI-4739.

The CBR variant may have a Km for PBI-4739 that is at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 30-fold, at least about 4-fold, at least about 50-fold, at least about 60-fold, at least about 70-fold, at least about 80-fold, at least about 90-fold, at least about 100-fold lower, at least about 150-fold, at least about 200-fold, at least about 300-fold, at least about 400-fold, at least about 500-fold, or at least about 1000-fold lower than the Km of a CBR polypeptide of SEQ ID NO: 1 for D-luciferin.

The CBR variant may have a relative Vmax for PBI-4813 that is at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 30-fold, at least about 4-fold, at least about 50-fold, at least about 60-fold, at least about 70-fold, at least about 80-fold, at least about 90-fold, at least about 100-fold lower, at least about 150-fold, at least about 200-fold, at least about 300-fold, at least about 400-fold, at least about 500-fold, or at least about 1000-fold higher than the relative Vmax of a CBR polypeptide of SEQ ID NO: 1 for PBI-4813.

The CBR variant may have a relative Vmax for PBI-4739 that is at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 30-fold, at least about 4-fold, at least about 50-fold, at least about 60-fold, at least about 70-fold, at least about 80-fold, at least about 90-fold, at least about 100-fold lower, at least about 150-fold, at least about 200-fold, at least about 300-fold, at least about 400-fold, at least about 500-fold, or at least about 1000-fold higher than the relative Vmax of a CBR polypeptide of SEQ ID NO: 1 for PBI-4739.

d. Fusion Proteins

In some embodiments, the CBR variant of the invention has one or more heterologous amino acid sequences at the N-terminus, C-terminus, or both (a fusion polypeptide such as one with an epitope or fusion tag), which optionally directly or indirectly interact with a molecule of interest. In some embodiments, the presence of the heterologous sequence(s) does not substantially alter the luminescence of the CBR variant either before or after the interaction with the molecule of interest. The heterologous amino acid sequence may be any protein of interest such as RNasin or RNase, and/or a channel protein, a receptor, a membrane protein, a cytosolic protein, a nuclear protein, a structural protein, a phosphoprotein, a kinase, a signaling protein, a metabolic protein, a mitochondrial protein, a receptor associated protein, a fluorescent protein, an enzyme substrate, a transcription factor, a transporter protein and/or a targeting sequence, e.g., a myristilation sequence, a mitochondrial localization sequence, or a nuclear localization sequence, that directs the hydrolase fragment, for example, a fusion protein, to a particular location.

In some embodiments, the heterologous amino acid sequence is an epitope tag. In some embodiments, the heterologous amino acid sequence is one which, during or after interaction with a molecule of interest, undergoes a conformational change, which in turn alters the activity of the CBR variant e.g., a CBR variant with such an amino acid sequence is useful to detect allosteric interactions. The CBR variant or a fusion with the CBR variant or a fragment thereof may be employed as a reporter.

The CBR variants of the present invention may be coupled to any protein of interest or molecule of interest. In some embodiments, the variants are fusion proteins, for example some variants are coupled to a HALOTAG® polypeptide (also referred to as "HT7") attached at either the N-terminus or the C-terminus. In some embodiments, a fusion or chimeric protein contains a CBR variant joined at the N-terminus to a HALOTAG® fusion protein (Promega). In other embodiments, a fusion or chimeric protein contains a CBR variant joined at the C-terminus to a HALOTAG® fusion protein. Signal sequences, in combination with membrane anchoring sequences, may be used to position or display CBR variants on the outer surface of the cellular membrane. Other methods, known in the art may also be used to position CBR variants to the membrane or other locations within the cell.

e. Vectors and Host Cells Encoding the Modified Luciferase or Fusions Thereof

Once a desirable nucleic acid molecule encoding a CBR variant or a fragment thereof, such as one with luminescence activity or which may be complemented by another molecule to result in luminescence activity, or a fusion thereof with luminescence activity, is prepared, an expression cassette encoding the CBR variant or a fragment thereof, e.g., one for complementation, or a fusion thereof with luminescence activity, may be prepared. For example, a nucleic acid molecule comprising a nucleic acid sequence encoding a CBR variant is optionally operably linked to transcription regulatory sequences, e.g., one or more enhancers, a promoter, a transcription termination sequence or a combination thereof, to form an expression cassette. The nucleic acid molecule or expression cassette may be introduced to a vector, e.g., a plasmid or viral vector, which optionally includes a selectable marker gene, and the vector introduced to a cell of interest, for example, a prokaryotic cell such as *E. coli, Streptomyces* spp., *Bacillus* spp., *Staphylococcus* spp. and the like, as well as eukaryotic cells including a plant (dicot or monocot), fungus (including yeast, e.g., *Pichia, Saccharomyces* or *Schizosaccharomyces*), or a mammalian cell, lysates thereof, or to an in vitro transcription/translation mixture. Mammalian cells include but are not limited to bovine, caprine, ovine, canine, feline, non-human primate, e.g., simian, and human cells. Mammalian cell lines include, but are not limited to, CHO, COS, HEK293, HeLa, CV-1, SH-SY5Y, and NIH 3T3 cells, although numerous other cell lines can also be used as well.

The expression of an encoded CBR variant may be controlled by any promoter capable of expression in prokaryotic cells or eukaryotic cells including synthetic promoters. Prokaryotic promoters include, but are not limited to, SP6, T7, T5, tac, bla, trp, gal, lac or maltose promoters, including any fragment that has promoter activity. Eukaryotic promoters include, but are not limited to, constitutive promoters, e.g., viral promoters such as CMV, SV40 and RSV promoters, as well as regulatable promoters, e.g., an inducible or repressible promoter such as the Tet promoter, the hsp70 promoter and a synthetic promoter regulated by CRE, including any fragment that has promoter activity. The expression of an encoded CBR variant may also be controlled by post-transcriptional processes, such as by regulation of RNA processing or regulation of translation, for example by RNAi, miRNA, shRNA, siRNA, or by RNA or protein degradation. The nucleic acid molecule, expression cassette and/or vector of the invention may be introduced to a cell by any method including, but not limited to, calcium-mediated transformation, electroporation, microinjection, lipofection, and the like.

f. Optimized Sequences Encoding the CBR Variants

Also provided is an isolated nucleic acid molecule (polynucleotide) comprising a nucleic acid sequence encoding a CBR variant of the invention, a functional fragment thereof or a fusion protein thereof. In some embodiments, the isolated nucleic acid molecule comprises a nucleic acid sequence which is optimized for expression in at least one selected host. Optimized sequences include sequences which are codon optimized, i.e., codons which are employed more frequently in one organism relative to another organism, e.g., a distantly related organism, as well as modifications to add or modify Kozak sequences and/or introns, and/or to remove undesirable sequences, for instance, potential transcription factor binding sites. Such optimized sequences can provide enhanced expression, e.g. increased levels of protein expression, when introduced into a host cell. Examples of optimized sequences are disclosed in U.S. Pat. No. 7,728,118 and U.S. Pat. Appl. Publ. Nos. 2008/0070299 and 2008/0090291, each of which is incorporated by reference herein.

In some embodiments, the polynucleotide includes a nucleic acid sequence encoding a CBR variant of the invention, which nucleic acid sequence is optimized for expression in a mammalian host cell in culture (e.g., CHO cells), in a living animal (e.g., mouse), or in a tissue-specific cell in a living animal. In some embodiments, the polynucleotide may include a codon optimized sequence of any one of SEQ ID NOs: 2-4. In some embodiments, the polynucleotide may include a polynucleotide sequence of any one of SEQ ID NOs: 7-9. In some embodiments, the polynucleotide may include a polynucleotide sequence of SEQ ID NO: 10. In some embodiments, the nucleic acid sequence is optimized for expression in a bacterial cell or plant. In some embodiments, an optimized polynucleotide no longer hybridizes to the corresponding non-optimized sequence, e.g., does not hybridize to the non-optimized sequence under medium or high stringency conditions. The term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "medium" or "low" stringency are often used when it is desired that nucleic acids that are not completely complementary to one another be hybridized or annealed together. The art knows well that numerous equivalent conditions can be employed to comprise medium or low stringency conditions.

In some embodiments, the polynucleotide has less than 90%, e.g., less than 80%, nucleic acid sequence identity to the corresponding non-optimized sequence and optionally encodes a polypeptide having at least 60%, e.g., at least 65%, 70%, 75%, 80%, 85%, 90%, 95%, 96%, 97%, 98%, 99%, or 100%, amino acid sequence identity with the polypeptide encoded by the non-optimized sequence. Constructs, e.g., expression cassettes, and vectors comprising the isolated nucleic acid molecule, e.g., with optimized nucleic acid sequence, as well as kits comprising the isolated nucleic acid molecule, construct or vector are also provided.

A nucleic acid molecule comprising a nucleic acid sequence encoding a CBR variant of the invention, a fragment thereof or a fusion thereof is optionally optimized for expression in a particular host cell and also optionally operably linked to transcription regulatory sequences, e.g., one or more enhancers, a promoter, a transcription termination sequence or a combination thereof, to form an expression cassette.

In some embodiments, a nucleic acid sequence encoding a CBR variant of the invention, a fragment thereof or a fusion thereof is optimized by replacing codons, e.g., at least 25% of the codons in a parental CBR sequence with codons which are preferentially employed in a particular (selected) cell. Preferred codons have a relatively high codon usage frequency in a selected cell, and preferably their introduction results in the introduction of relatively few transcription factor binding sites for transcription factors present in the selected host cell, and relatively few other undesirable structural attributes. Examples of undesirable structural attributes include, but not limited to, restriction enzyme sites, eukaryotic sequence elements, vertebrate promoter modules and transcription factor binding sites, response elements, *E. coli* sequence elements, mRNA secondary structure. Thus, the optimized nucleic acid product may have an improved level of expression due to improved codon usage frequency, and a reduced risk of inappropriate transcriptional behavior due to a reduced number of undesirable transcription regulatory sequences.

An isolated and optimized nucleic acid molecule may have a codon composition that differs from that of the corresponding wild-type nucleic acid sequence at more than 30%, 35%, 40% or more than 45%, e.g., 50%, 55%, 60% or more of the codons. Exemplary codons for use in the invention are those which are employed more frequently than at least one other codon for the same amino acid in a particular organism and, in some embodiments, are also not low-usage codons in that organism and are not low-usage codons in the organism used to clone or screen for the expression of the nucleic acid molecule. Moreover, codons for certain amino acids (i.e., those amino acids that have three or more codons), may include two or more codons that are employed more frequently than the other (non-preferred) codon(s). The presence of codons in the nucleic acid molecule that are employed more frequently in one organism than in another organism results in a nucleic acid molecule which, when introduced into the cells of the organism that employs those codons more frequently, is expressed in those cells at a level that is greater than the expression of the wild-type or parent nucleic acid sequence in those cells.

In some embodiments of the invention, the codons that are different are those employed more frequently in a mammal, while in still other embodiments, the codons that are different are those employed more frequently in a plant or bacteria. Preferred codons for different organisms are known to the art, e.g., see www.kazusa.or.jp/codon/. A particular type of mammal, e.g., a human, may have a different set of preferred codons than another type of mammal. Likewise, a particular type of plant or bacteria may have a different set of preferred codons than another type of plant or bacteria. In some embodiments of the invention, the majority of the codons that differ are ones that are preferred codons in a desired host cell. Preferred codons for organisms including mammals (e.g., humans) and plants are known to the art (e.g., Wada et al., Nucl. Acids Res., 18:2367 (1990); Murray et al., Nucl. Acids Res., 17:477 (1989)).

3. Near-Infrared Bioluminescence Systems

The present disclosure also provides near-IR bioluminescence systems that include the CBR variants, described above, and a novel luciferin derivative. Certain combinations of the CBR variants and novel luciferin derivatives provide significant technical advantages for bioluminescent assays especially for in depth tissue imaging because near-IR luminescence is generated. The disclosed invention provides enhanced detection of signals from deep animal tissues, in part, because of the longer wavelength are not absorbed by the tissues, but also because there is an improvement in light emission over the parental CBR and known luciferin substrates. In addition, other reagents may be included to bioluminescence systems, including but not limited to those that inhibit or prevent inactivation of the CBR variant or otherwise extend or enhance luminescent signal.

a. Novel Luciferin Derivatives

The near-IR bioluminescence systems may include novel red-shifted luciferin derivatives, such as those disclosed in PCT application No. PCT/US2014/021678, which is incorporated herein by reference in its entirety. For example, the luciferin derivative may include a compound of one of Formulas (Ia), (Ib), (Ic), (II), (III), (IV), (V), (VI), or (VII), or pro-substrates thereof, such as Reductase Substrates, Glycosidase Substrates, Protease and Protease-Dependent Protein Modifying Substrates, Oxidase Substrates, Carboxyl-Based Pro-Substrates, Glutathione Transferase Substrate, Beta-Lactamase Substrates, and Other Pro-Substrates. In some embodiments, the novel luciferin derivative may be PBI-4739 or PBI-4813 (see FIG. 1; disclosed in PCT Application No. PCT/US2014/021678).

(1) Compound of Formula(s) (Ia), (Ib), (Ic), (II), (III), (IV), (V), (VI), or (VII)

The luciferin derivative may include a compound according to Formulas (Ia), (Ib) and (Ic):

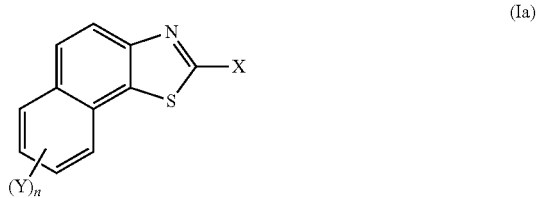

(Ia)

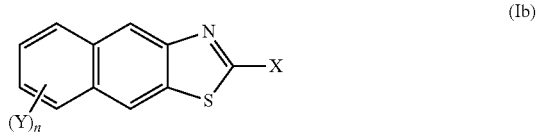

(Ib)

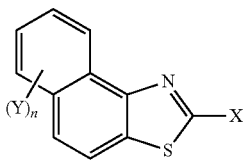

wherein
X is CN or

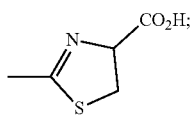

each Y is independently halo, $SO_3H$, $C_{1-4}$ alkyl, substituted $C_{1-4}$ alkyl, $OR^1$ or $NR^1R^2$;
each $R^1$ is H, $C_{1-10}$ alkyl or substituted $C_{1-10}$ alkyl;
each $R^2$ is H, $C_{1-10}$ alkyl or substituted $C_{1-10}$ alkyl; or
$R^1$ and $R^2$ together form a 4 to 8 membered ring;
n is 1 to 6;
two Y substituents may join together to form a ring containing from 5 to 7 ring atoms; and wherein at least one Y is either OH or $NR^1R^2$.

The luciferin derivative may include a compound, but are not limited to:

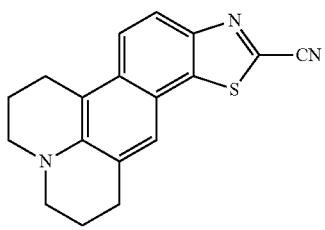

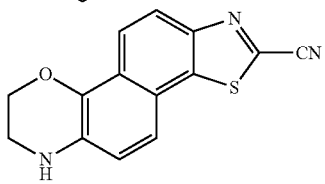

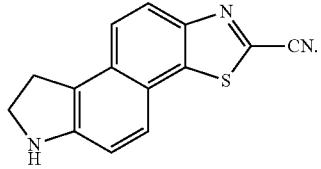

In other embodiments, the luciferin derivative may include a compound according to Formula (II):

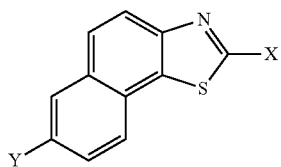

(II)

wherein
X is CN or

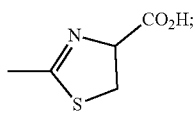

Y is $OR^1$ or $NR^1R^2$;
$R^1$ is H, $C_{1-10}$ alkyl or substituted $C_{1-10}$ alkyl; and
$R^2$ is H, $C_{1-10}$ alkyl or substituted $C_{1-10}$ alkyl; or
$R^1$ and $R^2$ together form a ring.

In a further embodiments, the luciferin derivative may include a compound according to Formula (III):

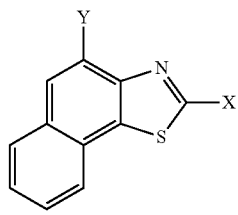

(III)

wherein
X is CN or

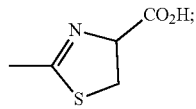

Y is $OR^1$ or $NR^1R^2$;
$R^1$ is H, $C_{1-10}$ alkyl or substituted $C_{1-10}$ alkyl; and
$R^2$ is H, $C_{1-10}$ alkyl or substituted $C_{1-10}$ alkyl; or
$R^1$ and $R^2$ together form a ring.

In yet other embodiments, the luciferin derivative may include a compound according to Formula (IV):

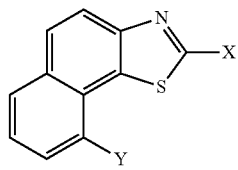

(IV)

wherein
X is CN or

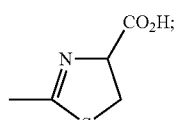

Y is $OR^1$ or $NR^1R^2$;
$R^1$ is H, $C_{1-10}$ alkyl or substituted $C_{1-10}$ alkyl; and
$R^2$ is H, $C_{1-10}$ alkyl or substituted $C_{1-10}$ alkyl; or
$R^1$ and $R^2$ together form a ring.

In other embodiments, the luciferin derivative may include a compound according to Formula (V):

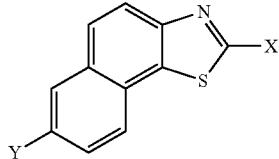
(V)

wherein
X is CN or

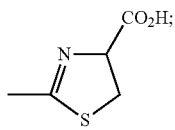

Y is OR$^1$ or NR$^1$R$^2$;
R$^1$ is H, C$_{1-10}$ alkyl or substituted C$_{1-10}$ alkyl; and
R$^2$ is H, C$_{1-10}$ alkyl or substituted C$_{1-10}$ alkyl; or
R$^1$ and R$^2$ together form a ring.

In other embodiments, the luciferin derivative may include a compound according to Formula (VI):

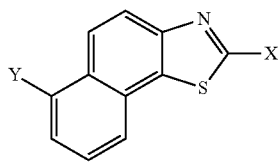
(VI)

wherein
X is CN or

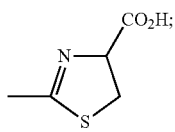

Y is OR$^1$ or NR$^1$R$^2$;
R$^1$ is H, C$_{1-10}$ alkyl or substituted C$_{1-10}$ alkyl; and
R$^2$ is H, C$_{1-10}$ alkyl or substituted C$_{1-10}$ alkyl; or
R$^1$ and R$^2$ together form a ring.

In an additional embodiments, the luciferin derivative may include a compound according to Formula (VII):

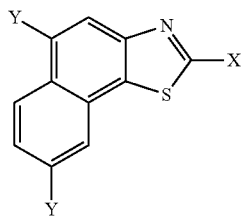
(VII)

wherein
X is CN or

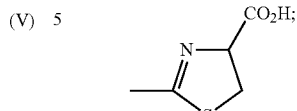

each Y is independently OR$^1$ or NR$^1$R2;
each R$^1$ is independently H, C$_{1-10}$ alkyl or substituted C$_{1-10}$ alkyl; and
each R$^2$ is independently H, C$_{1-10}$ alkyl or substituted C$_{1-10}$ alkyl; or
R$^1$ and R$^2$ together form a ring.

In certain embodiments, the emission maximum of the compounds is at least about 650 nm, about 655 nm, about 680, or about 760 nm.

(2) Pro-Substrates

The present invention also provides compounds which are substrates for various non-luciferase enzymes and are pro-substrates for luciferase enzymes. The non-luciferase enzymes include, but are not limited to, reductases, glycosidases, proteases, peptidases, oxidases, esterases, cytochrome P450s, beta-lactamases, glycosylases and glutathione transferases.

In some embodiments, these pro-substrates have a substituent that is a substrate for a non-luciferase position at the one or more Y positions which is cleaved to form

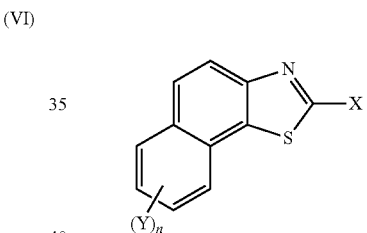
(VIII)

wherein
X is CN or

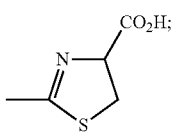

each Y is OH or NH$_2$, and
n is 1 to 3.

(a) Reductase Substrates

In some embodiments, the compound is a reductase substrate. In some embodiments, a reductase substrate has the formula:

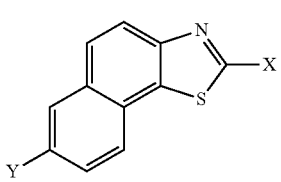
(IX)

wherein
X is CN or

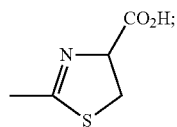

Y is OR;
R is

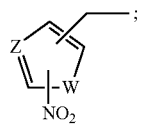

W is S, $NR_N$, or O;
Z is S, $NR_N$, O or CH; and
$R_N$ is H, $C_{1-4}$ alkyl, or substituted $C_{1-4}$ alkyl.

In some embodiments, a reductase substrate has the formula:

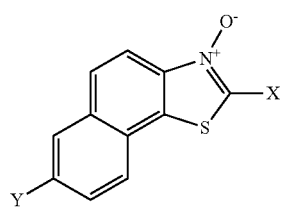

(X)

wherein
X is CN or

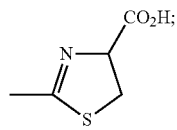

Y is $OR^1$ or $NR^1R^2$; and
$R^1$ is H, $C_{1-10}$ alkyl or substituted $C_{1-10}$ alkyl;
$R^2$ is H, $C_{1-10}$ alkyl or substituted $C_{1-10}$ alkyl; or
$R^1$ and $R^2$ together form a 4 to 8 membered ring.

In some embodiments, a reductase substrate has the formula:

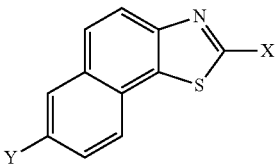

(XI)

wherein
X is CN or

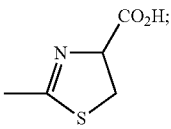

Y is OR; and
R is

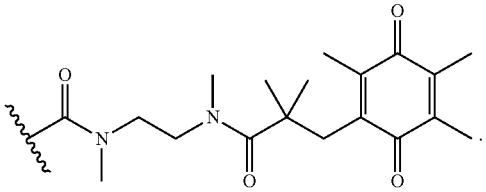 [SMILES: *C(=O)N(C)CCN(C)C(=O)C(C)(C)CC1=C(C)C(=O)C(C)=C(C)C1=O]

Reductase substrates include, but are not limited to, the following compounds:

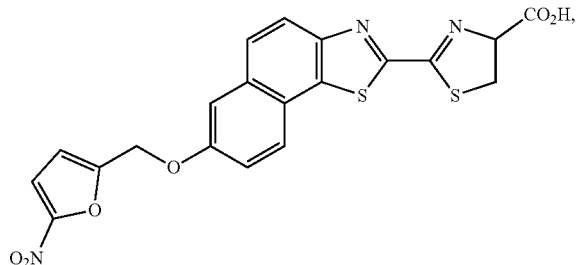

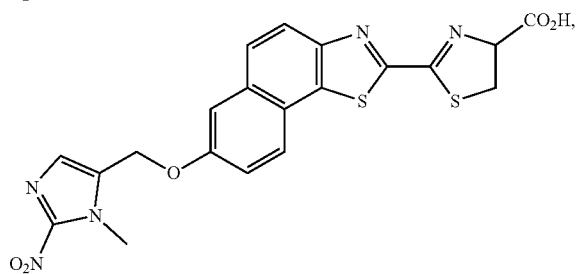

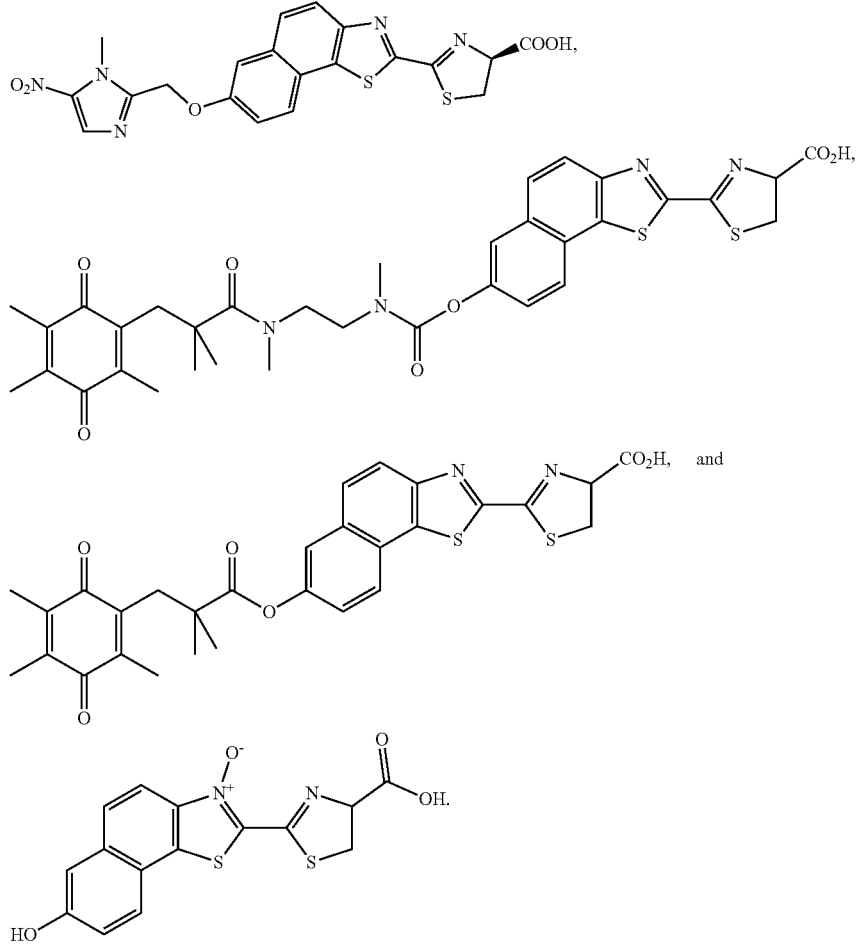

(b) Glycosidase Substrates

In some embodiments, the compound is a glycosidase substrate. In some embodiments, the glycosidase substrate is a compound of formula:

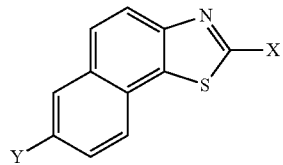

(XII)

wherein

X is CN or

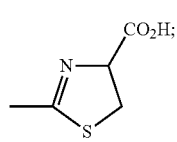

Y is OR;

R is

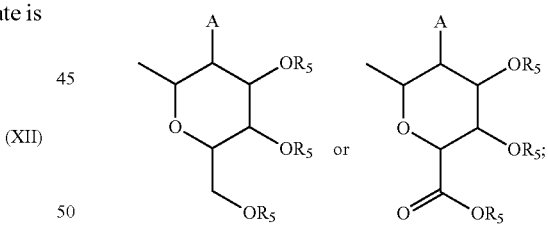

A is OR or NHAc;
each $R_5$ is independently H, a monosaccharide or a polyethylene glycol moiety of up to 40 units.

Glycosidase substrates include, but are not limited to, the following compounds:

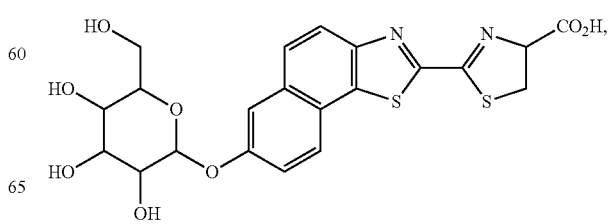

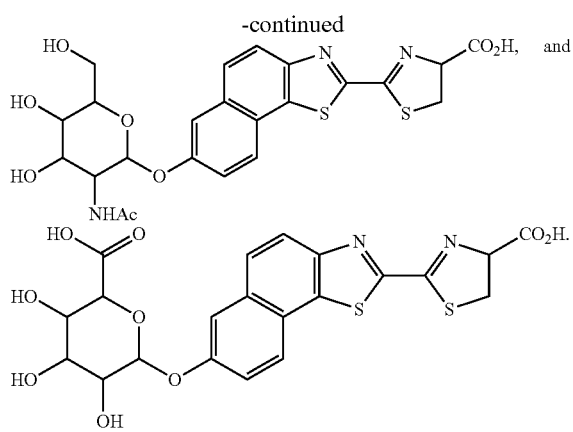

(c) Protease and Protease-Dependent Protein Modifying Substrates

In some embodiments, the compound is a protease or protease-dependent protein modifying substrate. In some embodiments, the substrate is a compound of formula:

(XIII)

wherein

X is CN or

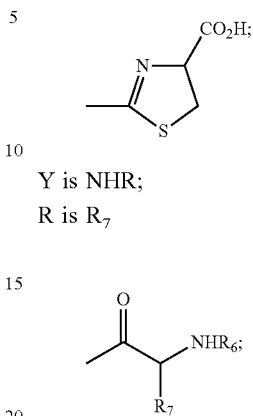

Y is NHR;

R is $R_7$ $R_7$ is an amino acid side chain;

$R_6$ is H, a nitrogen protecting group, or a chain of up to 20 amino acids.

Suitable nitrogen protecting groups include, but are not limited to, those traditionally known to those skilled in the art, such as Boc, Cbz, Ac and Fmoc.

These substrates include, but are not limited to, the following compounds:

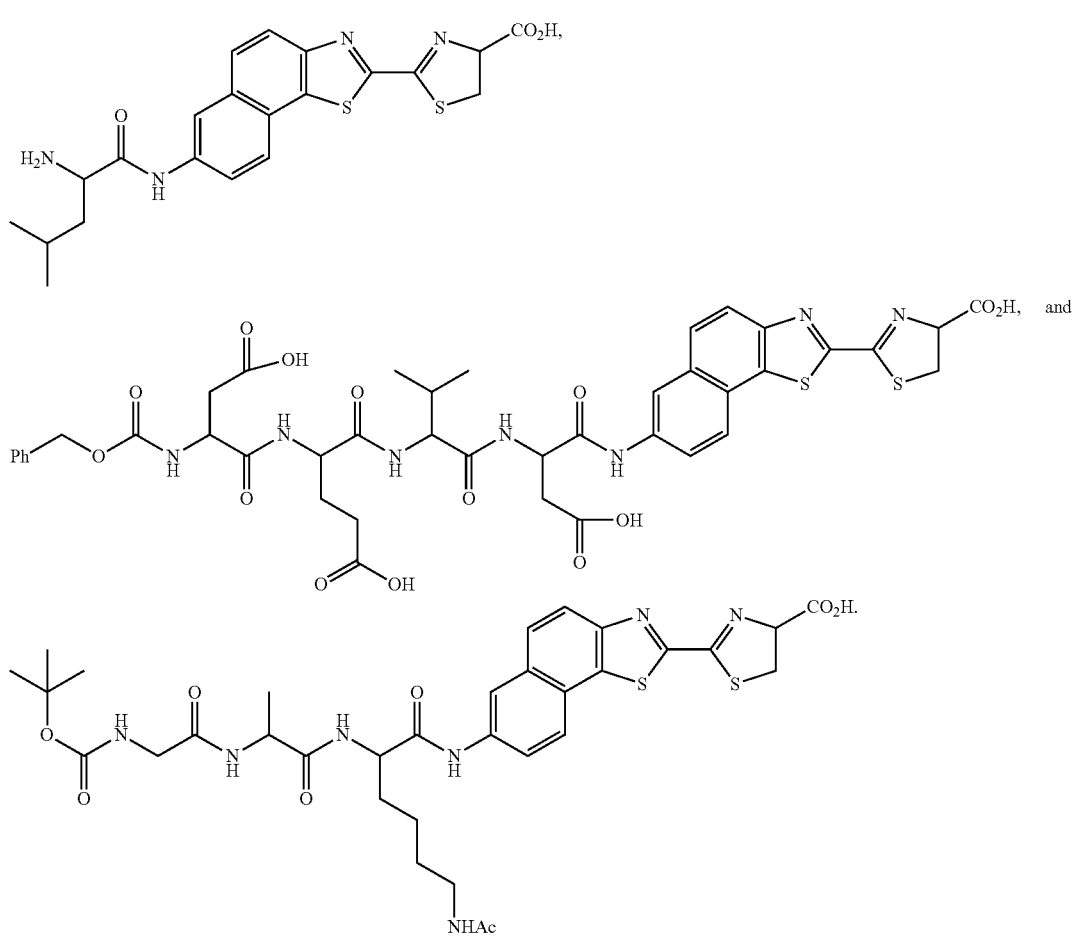

(d) Oxidase Substrates

In some embodiments, the compound is an oxidase substrate. In some embodiments, an oxidase substrate is a compound of formula:

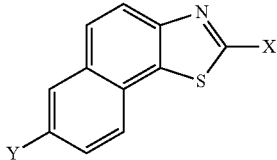
(XIV)

wherein
X is —CH(OR$_{10}$)$_2$;
R$_{10}$ is C$_{1-4}$ alkyl, substituted C$_{1-4}$ alkyl, benzyl, or substituted benzyl;
Y is OR$^1$ or NR$^1$R$^2$; and
R$^1$ is H, C$_{1-10}$ alkyl or substituted C$_{1-10}$ alkyl;
R$^2$ is H, C$_{1-10}$ alkyl or substituted C$_{1-10}$ alkyl; or
R$^1$ and R$^2$ together form a 4 to 8 membered ring.

In some embodiments, an oxidase substrate is a compound of formula:

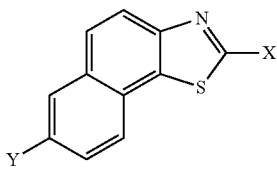
(XV)

wherein
X is CN or

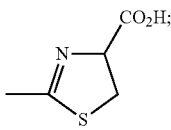

Y is H or OR; and
R is C$_{1-10}$ alkyl, substituted C$_{1-10}$ alkyl, aryl, substituted aryl, aralkyl or substituted aralkyl.

In some embodiments, an oxidase substrate is a compound of formula:

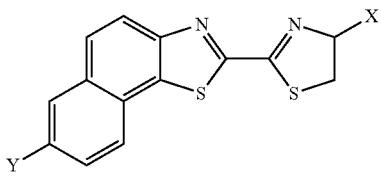
(XVI)

wherein
X is —CH(OR$_{10}$)$_2$;
R$_{10}$ is C$_{1-4}$ alkyl, substituted C$_{1-4}$ alkyl, benzyl or substituted benzyl;
Y is OR$^1$ or NR$^1$R$^2$; and
R$^1$ is H, C$_{1-10}$ alkyl or substituted C$_{1-10}$ alkyl;
R$^2$ is H, C$_{1-10}$ alkyl or substituted C$_{1-10}$ alkyl; or
R$^1$ and R$^2$ together form a 4 to 8 membered ring.

Oxidase substrates include, but are not limited to, the following compounds:

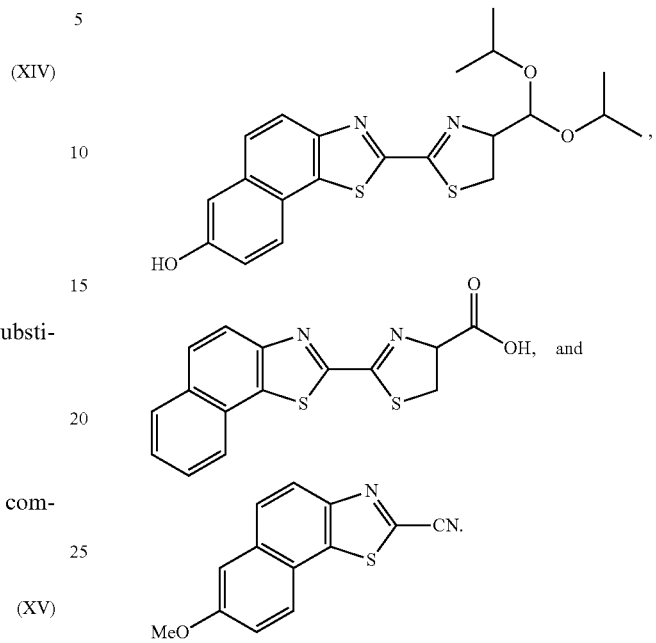

(e) Carboxyl-Based Pro-Substrates

In some embodiments, the compound is a carboxyl-based pro-substrate. In some embodiments, the carboxyl-based pro-substrate is a compound of formula:

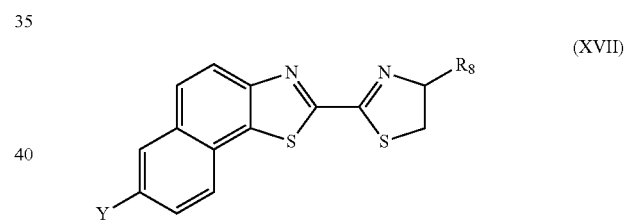
(XVII)

wherein
R$_8$ is CH$_2$OH, C(O)R$_{10}$ or —C(O)ZR$_9$;
Z is O or NH;
R$_9$ is C$_{1-7}$ alkyl or substituted C$_{1-7}$ alkyl;
R$_{10}$ is a peptide;
Y is OR$^1$ or NR$^1$R$^2$; and
R$^1$ is H, C$_{1-10}$ alkyl or substituted C$_{1-10}$ alkyl;
R$^2$ is H, C$_{1-10}$ alkyl or substituted C$_{1-10}$ alkyl; or
R$^1$ and R$^2$ together form a 4 to 8 membered ring.

Carboxyl-based pro-substrates include, but are not limited to, the following compounds:

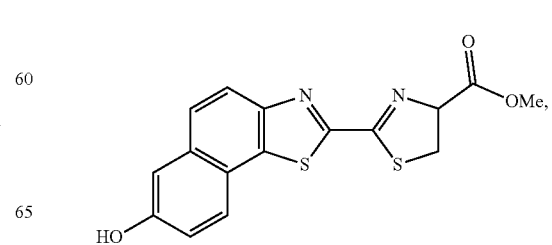

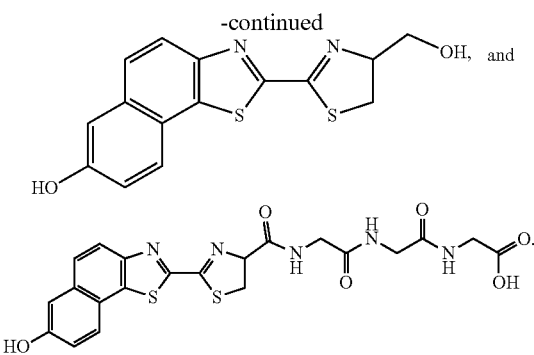

(f) Glutathione Transferase Substrate

In some embodiments, the compound may be a glutathione transferase substrate. In some embodiments, the glutathione transferase substrate is a compound of formula:

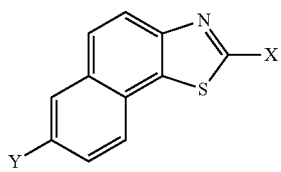
(XVIII)

wherein
X is CN or

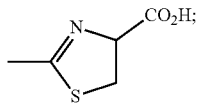

Y is OR;
R is

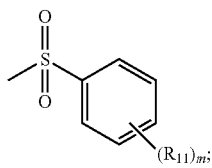

each $R_{11}$ is independently H, $C_{1-6}$ alkyl, substituted $C_{1-6}$ alkyl, $CF_3$, halogen, $NO_2$, $CO_2R_{12}$ or any two adjacent $R_{11}$ can form a fused ring provided that at least one of $R_{11}$ is $NO_2$; and
$R_{12}$ is H, $C_{1-6}$ alkyl or substituted $C_{1-6}$ alkyl.

Glutathione transferase substrates include, but are not limited to, the following compounds:

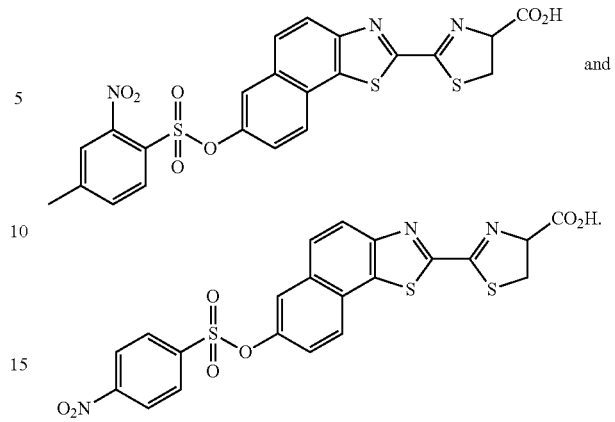

(g) Beta-Lactamase Substrates

In some embodiments, the compound is a beta-lactamase substrate. In some embodiments, the beta-lactamase substrate is a compound of formula:

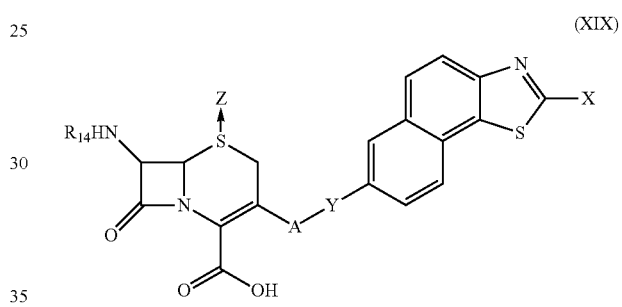
(XIX)

wherein
X is CN or

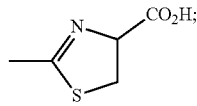

Y is O, NH, $N(C_{1-7}$ alkyl), or N(substituted $C_{1-7}$ alkyl);
Z is absent or O;
A is $C_{1-4}$ alkylene or substituted $C_{1-4}$ alkylene; and
$R_{14}$ is H, phenacetyl, or a cephalosporin side chain.

Suitable cephalosporin side chains include those known to one of ordinary skill in the art.

Beta-lactamase substrates include, but are not limited to, the following compounds:

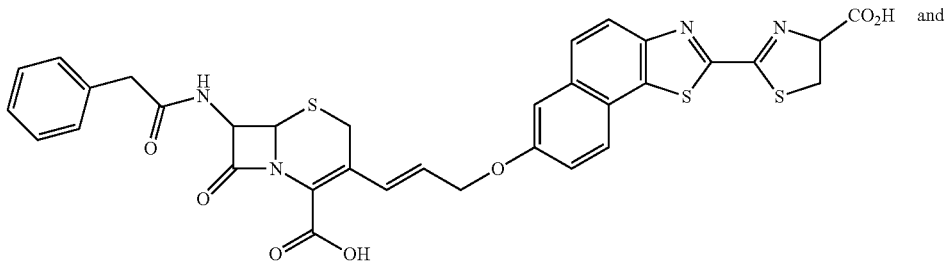

-continued

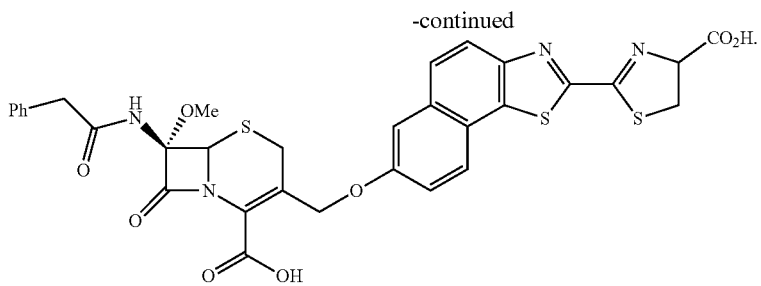

(h) Other Pro-Substrates

The present invention also provides compounds which react with various biologically important small molecules, such as hydrogen peroxide, and are pro-substrates for luciferase enzymes. In some embodiments, these compounds are reactive to hydrogen peroxide. In some embodiments, these compounds have the formula:

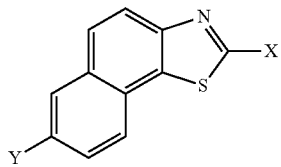
(XX)

wherein
X is CN or

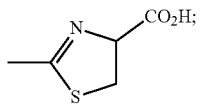

Y is L-R;
L is a linker; and
R is a boronic acid or borate ester.

In some embodiments, R is $-B(OR_{15})_2$; wherein each $R_{15}$ is independently selected from H and $C_{1-4}$ alkyl. In some embodiments, R is

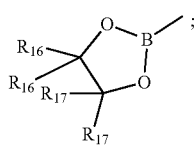

wherein each $R_{16}$ and $R_{17}$ is independently selected from H, $C_{1-4}$ alkyl, substituted $C_{1-4}$ alkyl, $CF_3$, phenyl or substituted phenyl; or $R_{16}$ and $R_{17}$ together can be an alkyl ring having from 3-7 carbons or can be replaced by a fused 6-membered aromatic ring.

In some embodiments, the linker is a direct bond. In other embodiments, the linker is

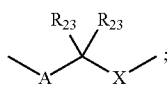

wherein
A is $-C_6(R_{20})_4-$, $-O-C_6(R_{20})_4-$ or $-(CR_{21}=CR_{21})_n-$ or $-S-C_6(R_{20})_4-$ or $-NR'-C_6(R_{20})_4$ or a direct bond;

R' is H, $C_{1-4}$ alkyl, or substituted $C_{1-4}$ alkyl;
each $R_{23}$ is independently halo, H, $C_{1-4}$ alkyl, substituted $C_{1-4}$ alkyl, $C_{1-4}$ hydroxyalkyl, substituted $C_{1-4}$ hydroxyalkyl, $C_{1-4}$ alkylcarboxylic acid or substituted $C_{1-4}$ alkylcarboxylic acid;
each $R_{20}$ is independently H, halo, $CH_3$, $OCH_3$, or $NO_2$;
each $R_{21}$ is independently H or $CH_3$;
n is 1 or 2; and
X is a selected from —O—,

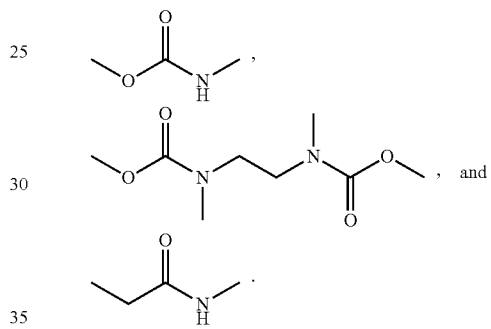

These compounds include, but are not limited to, the following compounds:

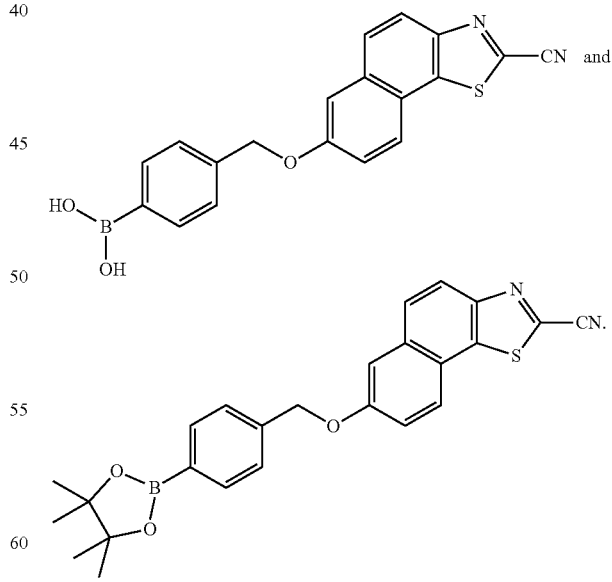

4. Methods of Using the CBR Variants and/or Bioluminescent Systems

The CBR variants and near-IR bioluminescence systems may be used in any way that luciferases and luciferase substrates, e.g., luciferin and luciferin derivatives, have been used. The CBR variants and/or near-IR bioluminescent systems may be used with a sample (including cells, tissues, animals, etc.) or with in vivo imaging and detected using various microscopy and imaging techniques. The CBR variants and/or near-IR bioluminescent systems may be used as a transcriptional reporter or as a biosensor. The CBR variants and/or near-IR bioluminescent systems may be used in dual-color assays or multiplexing. The CBR variants and/or near-IR bioluminescent systems may be used in assays to detect the presence or activity of enzymes such as non-luminescent enzymes. For example, they may be used in a bioluminogenic method which employs an analog of luciferins to detect one or more molecules in a sample, e.g., an enzyme, a cofactor for an enzymatic reaction, an enzyme substrate, an enzyme inhibitor, an enzyme activator, or OH radicals, or one or more conditions, e.g., redox conditions. In some embodiments, the CBR variants and/or near-IR bioluminescent systems may be used as an energy donor to another molecule (e.g., to a fluorophore, a chromophore, or a nanoparticle). The CBR variants and near-IR bioluminescence systems may be used in protein proximity assays or protein complementation assays. The disclosed CBR variants and/or near-IR bioluminescent systems of the invention are also useful in in situ methods of analyzing cells. Methods of performing in situ analysis of cells using a luciferase are known in the art. The disclosed CBR variants and/or near-IR bioluminescent systems of the invention may be used to distinguish between substrates and inhibitors of an enzyme. The screening may be performed either in vitro or in vivo.

The sample may include an animal (e.g., a vertebrate), a plant, a fungus, physiological fluid (e.g., blood, plasma, urine, mucous secretions and the like), a cell, a cell lysate, a cell supernatant, or a purified fraction of a cell (e.g., a subcellular fraction). The presence, amount, spectral distribution, emission kinetics, or specific activity of such a molecule may be detected or quantified. The molecule may be detected or quantified in solution, including multiphasic solutions (e.g., emulsions or suspensions), or on solid supports (e.g., particles, capillaries, or assay vessels).

The luciferase reaction may be restricted or limited by time, enzyme concentration, and/or substrate concentration. Reaction conditions may be adjusted so that the luciferase reaction is carried out under conditions that result in about, at least about, or at most about 20, 30, 40, 50, 60, 70, 80, 90, 95, 96, 97, 98, 99 or 100% completion, or any range derivable therein. For example, the reaction may be carried out at a temperature between about 20° C. and about 45° C., about 20° C. and about 40° C., about 20° C. and about 35° C., about 20° C. and about 30° C., about 20° C. and about 25° C., between about 25° C. and about 45° C., about 25° C. and about 40° C., about 25° C. and about 35° C., about 25° C. and about 30° C., between about 30° C. and about 45° C., about 30° C. and about 40° C., about 30° C. and about 35° C. C, between about 35° C. and about 45° C., or between about 35° C. and about 40° C. The reaction may be carried out at 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., or 45° C. These temperature condition and/or reaction may be maintained or measured for 1 min, 5 min, 10 min, 15 min, 20 min, 25 min, 30 min, 35 min, 40 min, 45 min, 50 min, 55 min, 60 min, 65 min, 70 min, 75 min, 80 min, 85 min, 90 min, 100 min, 110 min, 120 min, 130 min, 140 min, 150 min, 160 min, 170 min, 180 min, 190 min, 200 min, 210 min, 220 min, 230 min, 240 min, 250 min, or more.

a. In Vivo Imaging

The CBR variants and near-IR (NIR) bioluminescence systems may be used for in vivo imaging and may improve the speed, detection limit, and depth penetration of bioluminescence imaging. The CBR variants and near-IR bioluminescence systems provide a means for non-invasive animal imaging for a variety of applications, e.g. understanding tumor biology, evaluation of potential therapeutic compounds. For example, the methods described herein can be used for the rapid and inexpensive evaluation of tumor progression and response to anti-cancer therapeutics in small animals, e.g., using transgenic non-human animals, e.g., mice, that express a luciferase reporter gene linked to a promoter or gene that is expressed, e.g., selectively expressed, in the cells that are desired to be imaged. Expression of a selected protein of interest may be imaged in real time in a living cell or animal, using a cell or transgenic animal that expresses a reporter construct including a nucleic acid encoding a CBR variant linked in frame to a nucleic acid encoding the selected protein of interest, or to the promoter for the selected protein.

The methods may be performed on cells or animals (e.g., non-human mammals, e.g., experimental animals, such as rodents, e.g., rats or mice) that express a CBR variant reporter construct. Generating such cells or animals may be performed using standard molecular biological techniques. Sufficient amounts of the novel luciferin derivative described herein may be added or administered to the cells or animals, and images of the NIR bioluminescence may be obtained using standard imaging methods. The promoter activity, protein expression, protein subcellular localization, protein translocation, and protein half-life may be evaluated in real time in living cells and animals.

When an experimental animal is used, the cells containing the NIR bioluminescence can be identified and excised, and evaluated further, e.g., using assays for gene expression, protein expression, or other genetic or biochemical parameters. The bioluminescence system may be designed with another luciferin/luciferase pair (e.g., with different emission maxima) to allow for simultaneous imaging of bioluminescence from two or more luciferases.

(1) Imaging Methods

The methods described herein can be practiced with any imaging system that can detect near infrared bioluminescence. Common imaging systems are available from Xenogen (e.g., IVIS), Hamamatsu, Roper, and Kodak.

(2) Live Cell

In various embodiments, the CBR variants can be used for detecting luminescence in live cells. In some embodiments, a CBR variant can be expressed in cells (as a reporter or otherwise), and the cells treated with a luciferase substrate, e.g., luciferin, luciferin derivative, e.g., a novel luciferin derivative such as PBI-4739 or PBI-4813, or functional analog, which may permeate cells in culture, react with the CBR variant and generate luminescence. PBI-4739 or PBI-4813 show comparable non-toxicity to D-luciferin in terms of cell toxicity studies. In some embodiments, versions of PBI-4739 or PBI-4813 containing chemical modifications known to increase the stability of native luciferin derivative in media may be synthesized and used for more robust, live cell CBR variant-based reporter assays. In still other embodiments, a sample (including cells, tissues, animals, etc.) containing a CBR variant and/or a novel luciferin derivative of the present invention may be assayed using various microscopy and imaging techniques. In still other embodiments, a secretable CBR variant may be expressed in cells as part of a live-cell reporter system.

b. Use as Transcriptional Reporters

The CBR variants and near-IR bioluminescence systems may be used as genetic transcriptional reporter systems. The CBR variant or fragment thereof may be used to study transcriptional expression patterns of any promoter and/or gene, such as genes involved in development. In some embodiments, the CBR variant or fragment thereof could be operably linked to transcription regulatory sequences, e.g., one or more enhancer, a promoter, a transcription termination sequence or a combination thereof, to form an expression cassette. For example, the CBR variant could be operably linked to a minimal promoter and a cAMP-response element (CRE).

In certain embodiments, provided is a method for measuring the activity of a promoter in a sample, wherein the promoter is operably linked to a gene encoding a CBR variant enzyme. The method includes (a) contacting the sample with a luciferin or novel luciferin derivative; and (b) determining the activity of the promoter by measuring luminescence of the sample, wherein the sample comprises the promoter. The promoter may be operably linked to the gene via a translational or transcriptional fusion. A biological pathway of interest, for example, may be examined by treating a cell that comprises the promoter, which is operably linked to a gene encoding the luminescent enzyme, with an inducer agent of the pathway. This promoter activity may then be measured and monitored to study any correlation between the activity of the promoter and the pathway of interest, as well as obtain kinetic measurements relating to gene expression (e.g. inducibility, repression and activation).

c. Multiplexing

The CBR variant and bioluminescence system may be used in a multiplexed reaction with another enzyme (e.g. a luciferase) that emits light at a different wavelength. In some embodiments, the CBR variant may be used as a transcriptional reporter and paired with a luciferase that emits light at a different wavelength contained in an assay reagent. In some embodiments, the CBR variant may be used with one or more additional luciferases, where the luminescence of each luciferase may be separately measured through the use of selective enzyme inhibitors. For example, the luminescence of the CBR variant may be measured upon addition of appropriate substrates and buffers, followed by measurement of a second luciferase upon a subsequent addition of appropriate substrates and buffers and one or more inhibitors selective for the first luciferase.

In some embodiments, the CBR variant of the present invention may be used as a functional reporter for a particular gene and the second enzyme in the multiplex reaction may be used as a functional reporter for a second gene. In some embodiments, the CBR variant may be used with one or more additional luciferases, where the luminescence of each luciferase may be easily resolved using a luminometer with wavelength-discriminating filters enabling the measurement of both signals from the same sample. For example, luminescence generated from the CBR variant enzyme (between approximately 725-750 nm) and green CHROMA-LUC™ (approximately 537 nm) can be easily resolved using a luminometer with wavelength-discriminating filters, enabling the measurement of both signals from the same sample.

In some embodiments, a CBR variant may be used as transcriptional reporter and paired with either aequorin or a cAMP circularly-permuted firefly luciferase biosensor, or both simultaneously, to detect multiple pathways in a single sample. In such a system, for example, aequorin could be used for the detection and/or measurement of calcium, the biosensor for the detection and/or measurement of cAMP, and the CBR variant for monitoring of downstream gene expression.

The CBR variant may be multiplexed with a luciferase derived from: beetle luciferases, such as firefly (e.g., *Photinus pyralis* (e.g., Luc2; Promega Corp) or *Photuris pennsylvanica* luciferases) or a different click beetle luciferase (*Pyrophorus plagiophthalamus* or *Pyrearinus termitilluminans*), such as green click beetle luciferase (CHROMA-LUC™; Promega Corp.), a bioluminescent decapod, e.g. *Oplophorus* luciferase, such as *Oplophorus gracilirostris* luciferases or variants thereof, e.g., NanoLuc® luciferase (Promega Corporation), as described in U.S. Pat. Nos. 8,557,970 and 8,669,103, and U.S. Patent Publication Nos. 2014/0223590 and U.S. Patent Publication No. 2014/0227759, marine organisms such as enidarians (e.g., *Renilla reniformis* luciferase), copepod luciferases, such as *Gaussia* luciferase, e.g., *Gaussia princeps* luciferase, *Metridia* luciferases, e.g., *Metridia longa* and *Metridia pacifica* luciferases, *Vargula* luciferases, e.g., *Vargula hilgendorfii* luciferase, *Pleuromamma xiphias* luciferase, a glowworm luciferase (e.g. *Phrixothrix hirtus*), and variants, recombinants, and mutants thereof. The CBR variants may be multiplexed with green fluorescent protein (GFP), photoproteins such as Aequorin, obelin, iPhotina, and variants, recombinants, and mutants thereof. For example, if a CBR variant of the present invention is used as a functional reporter, then the green firefly luciferase or green CHROMA-LUC™ luciferase could be used to control for non-specific effects on genetic regulation or to normalize for transfection efficiency.

d. Detection of Non-luminescent enzymes

The CBR variant and bioluminescence system containing the pro-substrate described herein may be used in luminescence-based assays to detect the activity of a non-luminescent enzyme. The CBR variant and pro-substrate may be contained in an assay reagent for measuring a specific aspect of cellular physiology, for example ATP to estimate cell viability, or caspase activity to estimate cellular apoptosis. The CBR variant and the pro-substrate may be added to a sample suspected of containing the non-luminescent enzyme of interest. The non-luminescent enzyme present in the sample reacts with the pro-substrate releasing the luciferin substrate for the CBR variant to use as a substrate and thus luminescence is generated and measured. In some embodiments, the non-luminescent enzyme of interest is a reductase, glycosidase, protease, serine proteases, threonine proteases, cysteine proteases, such as caspase-3 and caspase-8, aspartate proteases, glutamic acid proteases, and metalloproteases, peptidase, oxidase, such as a monoamine oxidase enzyme, esterase, cytochrome P450, beta-lactamase, glycosylase and glutathione transferase protease enzyme, such as a glutathione S-transferase enzyme. In some embodiments, the pro-substrates, as described herein may be used to detect the non-luminescent enzymes.

e. Bioluminescence Resonance Energy Transfer (BRET)

The CBR variant and bioluminescence system may be used in any method for detecting ligand-protein and/or protein-protein interactions. In various embodiments, the CBR variant enzymes may be used to transfer energy to an energy acceptor. One such method is Bioluminescence Resonance Energy Transfer (BRET). With respect to BRET, energy transfer from a bioluminescent donor to a fluorescent acceptor results in a shift in the spectral distribution of the emission of light. This energy transfer may enable real-time monitoring of protein-protein or ligand-protein interaction in vitro or in vivo.

In some embodiments, the CBR variant enzymes used in BRET analysis can be used to determine if two molecules are capable of binding to each other or co-localize in a cell. For example, a CBR variant enzyme can be used as a bioluminescence donor molecule which is combined with a molecule or protein of interest to create a first fusion protein. In various embodiments, the first fusion protein contains a CBR variant enzyme and a protein of interest. In various embodiments, the first fusion proteins containing the CBR variant enzyme can be used in BRET analysis to detect protein/protein interaction in systems including but not limited to cell lysates, intact cells, and living animals. In various embodiments, HALOTAG® can be used as a fluorescent acceptor molecule. In some embodiments, HALOTAG® can be fused to a second protein of interest or to a CBR variant enzyme. For example, a CBR variant enzyme can be fused to HALOTAG®, expressed in cells or animals, and labeled with a fluorescent HALOTAG® ligand such as HALOTAG® TMR ligand. The fusion can subsequently be excited to fluoresce in the presence of a cell-permeant CBR variant enzyme substrate. In some embodiments, BRET may be performed using CBR variant enzymes in combination with fluorescent proteins, including but not limited to Green Fluorescent Protein (GFP), Red Fluorescent Protein (RFP), far red fluorescent protein, and near infrared fluorescent proteins, such as iRFP and IFP1.4, or fluorescent labels including fluorescein, rhodamine green, Oregon green, Alexa 488, to name a few non-limiting examples. The fluorescent label may be a fluorescent BRET acceptor that absorbs at the emission of the luciferase (e.g., 650-750 nm), such as IRDye® 800CW, IRDye® 800RS, IRDye® 800 phosphoramidite, IRDye® 750, IRDye® 700DX, IRDye® 700 phosphoramidite, IRDye® 680LT, IRDye® 680RD, IRDy IRDye® e 650, 1,1',3,3,3',3'-Hexamethylindotricarbocyanine iodide, 1,1'-Diethyl-2,2'-dicarbocyanine iodide, 1,1'-Diethyl-4,4'-carbocyanine iodide, 1,4,8,11,15,18,22,25-Octabutoxy-29H,31H-phthalocyanine, 2,11,20,29-Tetra-tert-butyl-2,3-naphthalocyanine, 2,3,9,10,16,17,23,24-Octakis(octyloxy)-29H,31H-phthalocyanine, 2,3-Naphthalocyanine Dye content, 2,9,16,23-Tetra-tert-butyl-29H,31H-Phthalocyanine, 29H,31H-Phthalocyanine ß-form, 3,3'-Diethylthiadicarbocyanine iodide, 3,3'-Diethylthiatricarbocyanine iodide, 3,3'-Diethylthiatricarbocyanine perchlorate, Aluminum 1,8,15,22-tetrakis(phenylthio)-29H,31H-phthalocyanine chloride, Aluminum 2,9,16,23-tetrakis(phenylthio)-29H,31H-phthalocyanine chloride, Aluminum 2,9,16,23-tetraphenoxy-29H,31H-phthalocyanine chloride, Aluminum 2,9,16,23-tetraphenoxy-29H,31H-phthalocyanine hydroxide, Aluminum phthalocyanine chloride, Aluminum phthalocyanine hydroxide, Cobalt(II) 1,2,3,4,8,9,10,11,15,16,17,18,22,23,24,25-hexadecafluoro-29H,31H-phthalocyanine, Cobalt(II) 2,3-naphthalocyanine, Cobalt(II) phthalocyanine ß-form, Copper phthalocyanine-3,4',4?,4?'-tetrasulfonic acid tetrasodium salt, Copper(II) 1,2,3,4,8,9,10,11,15,16,17,18,22,23,24,25-hexadecafluoro-29H,31H-phthalocyanine, Copper(II) 1,4,8,11,15,18,22,25-octabutoxy-29H,31H-phthalocyanine, Copper(II) 2,3,9,10,16,17,23,24-octakis(octyloxy)-29H,31H-phthalocyanine, Copper(II) 2,3-naphthalocyanine, Copper(II) 2,9,16,23-tetra-tert-butyl-29H,31H-phthalocyanine, Copper(II) phthalocyanine-tetrasulfonic acid tetrasodium salt, Copper(II) phthalocyanine, Copper(II) phthalocyanine ß-form, Copper (II) phthalocyanine sublimed grade, Copper(II) phthalocyanine, Dilithium phthalocyanine, Disodium phthalocyanine, Gallium(III)-phthalocyanine chloride, IR-775 chloride, IR-780 iodide, IR-783, IR-792 perchlorate, IR-797 chloride, Iron(II) phthalocyanine, Iron(III) phthalocyanine chloride, Iron(III) phthalocyanine-4,4',4'',4'''-tetrasulfonic acid, compound with oxygen monosodium salt hydrate, Lead(II) phthalocyanine, Lead(II) tetrakis(4-cumylphenoxy)phthalocyanine, Magnesium phthalocyanine, Manganese(II) phthalocyanine, Manganese(III) phthalocyanine chloride, Methylsilicon(IV) phthalocyanine hydroxide, Naphthol Green B, Nickel(II) 1,4,8,11,15,18,22,25-octabutoxy-29H,31H-phthalocyanine, Nickel(II) phthalocyanine-tetrasulfonic acid tetrasodium salt, Nickel(II) phthalocyanine, Poly(copper phthalocyanine), Silicon 2,3-naphthalocyanine bis(trihexylsilyloxide), Silicon 2,3-naphthalocyanine dichloride, Silicon 2,3-naphthalocyanine dihydroxide, Silicon 2,3-naphthalocyanine dioctyloxide, Silicon 2,9,16,23-tetra-tert-butyl-29H,31H-phthalocyanine dihydroxide, Silicon phthalocyanine dichloride, Silicon phthalocyanine dihydroxide, Tin(IV) phthalocyanine oxide, Titanium(IV) phthalocyanine dichloride, Titanyl phthalocyanine, Titanyl phthalocyanine, Vanadyl 2,3-naphthalocyanine, Vanadyl 3,10,17,24-tetra-tert-butyl-1,8,15,22-tetrakis(dimethylamino)-29H,31H-phthalocyanine Dye content 80%, Zinc 1,2,3,4,8,9,10,11,15,16,17,18,22,23,24,25-hexadecafluoro-29H,31H-phthalocyanine, Zinc 1,4,8,11,15,18,22,25-octabutoxy-29H,31H-phthalocyanine, Zinc 2,11,20,29-tetra-tert-butyl-2,3-naphthalocyanine, Zinc 2,3,9,10,16,17,23,24-octakis(octyloxy)-29H,31H-phthalocyanine, Zinc 2,9,16,23-tetra-tert-butyl-29H,31H-phthalocyanine, Zinc phthalocyanine, or Zinc(II) tetranitrophthalocyanine.

f. Protein Proximity Assays for Live Cells or Lytic Formats

In some embodiments, the CBR variant may be used as a circularly permuted (CP) or straight split (SS) luminescent enzyme fusion protein to measure protein proximity. The CBR variant enzyme is permuted or split via insertion of a protease substrate amino acid sequence (e.g., TEV) to generate low bioluminescence. The CBR variant luminescent enzyme is tethered (e.g., via genetic fusion) to a monitor protein. A potential interacting protein is tethered (e.g., via genetic fusion) to a protease (e.g., TEV). When the two monitor proteins interact or are in sufficient proximity (e.g., via a constitutive interaction, a drug stimulus or a pathway response), the CBR variant enzyme is cleaved to generate increased bioluminescence activity. The example may be applied to measurements of protein proximity in cells or in biochemical assays.

g. Protein Complementation Assays

In some embodiments, the disclosed compounds may be used in other methods for detecting ligand-protein and protein-protein interactions or proximity, such as the protein complementation assay (PCA) or enzyme fragmentation assay. Protein complementation assays (PCA) provide a means to detect the interaction of two biomolecules, e.g., polypeptides. PCA utilizes two fragments of the same protein, e.g., the CBR variant, that when brought into close proximity with each other can reconstitute into a functional, active protein. In some embodiments, the PCA utilizing a CBR variant may be used to detect molecular proximity by virtue of the reconstitution of the CBR variant via the binding interaction of enzyme components or subunits. Fragments of the CBR variant are fused to proteins of interest. If the proteins of interest interact, the fragments of the CBR variant interact to reconstitute a full-length CBR variant enzyme.

For example, the CBR variant enzyme can be separated into two fragments at a site(s) tolerant to separation and each fragment of the separated CBR variant enzyme can be fused to one of a pair of polypeptides of interest believed to interact, e.g., FKBP and FRB. If the two polypeptides of interest do in fact interact, the CBR variant enzyme fragments, for example, then come into close proximity with each other to reconstitute the functional, active CBR variant enzyme. In some embodiments, the activity of the reconstituted CBR variant enzyme can then be detected and measured using the disclosed compounds and the cell-permeable substrate. In some embodiments, the split CBR variant enzyme can be used in a more general complementation system similar to lac-Z (Langley et al., PNAS 72:1254-1257 (1975)) or ribonuclease S (Levit and Berger, J. Biol. Chem. 251:1333-1339 (1976)). In some embodiments, a CBR variant enzyme fragment (designated "A") known to complement with another CBR variant enzyme fragment ("B") can be fused to a target protein, and the resulting fusion can be monitored via luminescence in a cell or cell lysate containing fragment B. In some embodiments, the source of fragment B could be the same cell (e.g., if the gene for fragment B is integrated into the genome of the cell or is contained on another plasmid within the cell) or it could be a lysate or purified protein derived from another cell. In some embodiments, this same fusion protein (fragment A) could be captured or immobilized using a fusion between fragment B and a polypeptide such as HALOTAG® capable of attachment to a solid support. In some embodiments, luminescence can be used to demonstrate successful capture or to quantify the amount of material captured.

h. Biosensors

The CBR variants may be used as biosensors, which, in the presence of another molecule (e.g., one or more molecules of interest), or under certain conditions, has one or more altered activities. Upon interacting with a molecule of interest or being subject to certain conditions, the biosensor undergoes a conformational change or is chemically altered which causes an alteration of the enzyme activity or luminescence, e.g., specific activity, spectral distribution, or emission kinetics. For example, the CBR variant of the present invention, for example a circularly permuted variant, can comprise an interaction domain for a molecule of interest. Alternatively, for example, the CBR variant may be coupled to an energy acceptor, for example a fluorescent protein, and comprise an interaction domain that alters the efficiency of energy transfer from the enzyme to the energy acceptor. For example, the biosensor could be generated to detect proteases, kinases, a ligand, a binding protein such as an antibody, cyclic nucleotides such as cAMP or cGMP, or a metal such as calcium, by insertion of a suitable sensor region into the CBR variant sequence. One or more sensor region can be inserted at the C-terminus, the N-terminus, and/or at one or more suitable location in the polypeptide sequence, where the sensor region comprises one or more amino acids. In the case of a circularly-permuted CBR variant, the sensor region may be inserted between the N- and C-termini of the parent CBR variant. In addition, one or all of the inserted sensor regions may include linker amino acids to couple the sensor to the remainder of the CBR variant polypeptide.

In some embodiments, full-length circularly permuted CBR variant enzymes may be fused to respective binding partners, e.g., FRB and FKBP, and used in a protein complementation-type assay with the luciferin or novel luciferin derivative. The key difference between the method disclosed herein and traditional protein complementation is that there was no complementation, but rather there was dimerization of two full length enzymes, e.g., circularly permuted CBR variant enzymes.

Briefly, the circularly permuted reporter proteins similarly configured for low activity are fused to both of the fusion protein partners. For example, each fusion partner may be linked to identically structured, permuted reporters. Interaction of the fusion partners brought the permuted reporters into close proximity, thereby allowing reconstitution of a hybrid reporter having higher activity.

5. Sample

The disclosed CBR variants and/or near-IR bioluminescent systems may be used with samples containing biological components. The sample may comprise cells and/or tissue. The sample may comprise heterogeneous mixtures of components (including intact cells, cell extracts, cell lysates, bacteria, viruses, organelles, and mixtures thereof) or a single component or homogeneous group of components (e.g., natural or synthetic amino acid, nucleic acid or carbohydrate polymers, or lipid membrane complexes). The compounds are generally non-toxic to living cells and other biological components within the concentrations of use.

The sample may include an animal (e.g., a vertebrate), a plant, a fungus, physiological fluid (e.g., blood, plasma, urine, mucous secretions and the like), a cell, a cell lysate, a cell supernatant, or a purified fraction of a cell (e.g., a subcellular fraction). In certain embodiments, the sample may be a cell. In some embodiments, the sample may be a live cell. The cell may be a eukaryotic cell, e.g., yeast, avian, plant, insect or mammalian cells, including but not limited to human, simian, murine, canine, bovine, equine, feline, ovine, caprine or swine cells, or prokaryotic cells, or cells from two or more different organisms, or cell lysates or supernatants thereof. The cells may not have been genetically modified via recombinant techniques (nonrecombinant cells), or may be recombinant cells which are transiently transfected with recombinant DNA and/or the genome of which is stably augmented with a recombinant DNA, or which genome has been modified to disrupt a gene, e.g., disrupt a promoter, intron or open reading frame, or replace one DNA fragment with another. The recombinant DNA or replacement DNA fragment may encode a molecule to be detected by the methods of the invention, a moiety which alters the level or activity of the molecule to be detected, and/or a gene product unrelated to the molecule or moiety that alters the level or activity of the molecule. The cells may have been genetically modified via recombinant techniques.

6. Kit

Kits for using the CBR variant and/or the near-IR bioluminescent systems are provided herein. Such kits comprise an active CBR variant and luciferin substrate. The kits may further include a buffer and instructions. The kit components, compositions, and buffers may also be modified by the addition of suitable components. Suitable kit components, compositions and buffers that may be used in the described methods can also be obtained commercially. The different components may comprise subsets of these parts and may be combined in any way that either facilitates the application of the invention or prolongs storage life.

In some embodiments, the kit comprises a separate container comprising lyophilized luciferase. In some embodiments, the container comprising lyophilized luciferase further comprises lyophilized luciferin or a derivative thereof that is a luciferase substrate.

One or more reagents may be supplied in a solid form or liquid buffer that is suitable for inventory storage, and later for addition into the reaction medium when the method of using the reagent is performed. Suitable packaging is provided.

(1) Containers/Vessels

The reagents included in the kits can be supplied in containers of any sort such that the life of the different components are preserved and are not adsorbed or altered by the materials of the container. For example, sealed glass ampules may contain lyophilized luciferase or buffer that has been packaged under a neutral, non-reacting gas, such as nitrogen. Ampules may consist of any suitable material, such as glass, organic polymers, such as polycarbonate, polystyrene, etc., ceramic, metal or any other material typically employed to hold reagents. Other examples of suitable containers include simple bottles that may be fabricated from similar substances as ampules, and envelopes, that may consist of foil-lined interiors, such as aluminum or an alloy. Other containers include test tubes, vials, flasks, bottles, syringes, or the like. Containers may have a sterile access port such as a bottle having a stopper that can be pierced by a hypodermic injection needle. Other containers may have two compartments that are separated by a readily removable membrane that upon removal permits the components to mix. Removable membranes may be glass, plastic, rubber, etc.

(2) Instructional Materials

The kits may also be supplied with instructional materials. Instructions may be printed on paper or other substrate and/or may be supplied as an electronic-readable medium such as a floppy disc, CD-ROM, DVD-ROM, Zip disc, videotape, audio tape, etc. Detailed instructions may not be physically associated with the kit; instead, a user may be directed to an internet web site specified by the manufacturer or distributor of the kit, or supplied as electronic mail.

7. Examples

The present invention can be utilized as illustrated by the following non-limiting examples.

Example 1

Characterization of Near-IR Substrates PBI-4739 and PBI-4813 with Ultra-Glo™ Luciferase, QuantiLum® Recombinant Luciferase, and Purified Click Beetle Red Luciferase (CBR)

Materials:

The following were used in the Examples: Ultra-Glo™ Luciferase (Promega Cat. No. E140); QuantiLum® Recombinant Luciferase (Promega Cat. No. E1701); Click Beetle Red Luciferase (CBR; 0.5 mg/mL purified; Promega); Bright-Glo™ assay buffer (Promega Cat. No. E264A); PBI-4739 (Promega—See FIG. 1); and PBI-4813 (Promega—See FIG. 1).

Experimental Details.

The substrates, PBI-4813 and PBI-4739, were diluted to 1 mM (final concentration) in Bright-Glo™ Assay buffer+1 mM ATP. 50 µL of substrate solution was added to 50 µL of Click Beetle Red, UltraGlo® or QuantiLum® purified enzyme (0.5 mg/mL diluted in DMEM+0.1% Prionex) in triplicate, and then the samples assayed using a Tecan M-1000 plate reader in spectral scan mode.

Figure 2A:
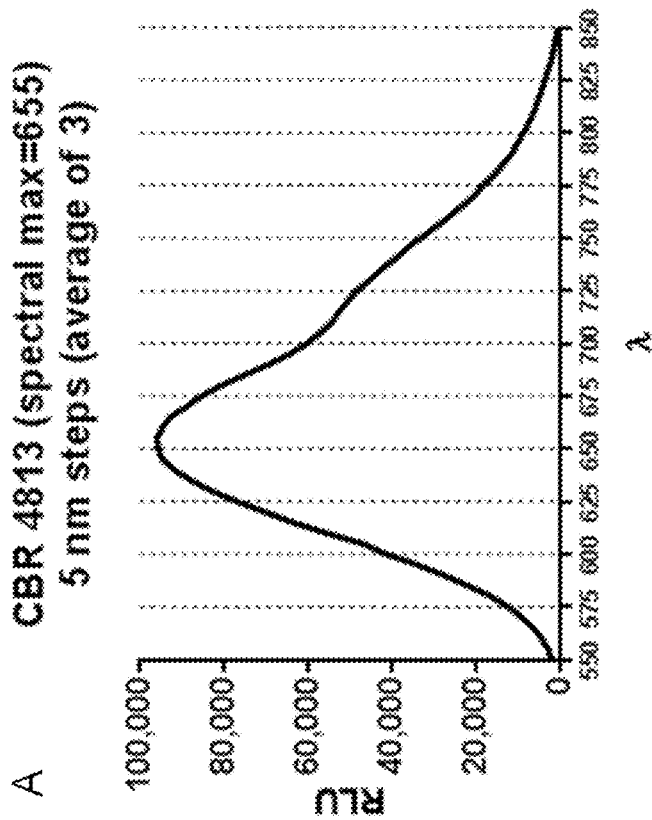
Figure 3B:
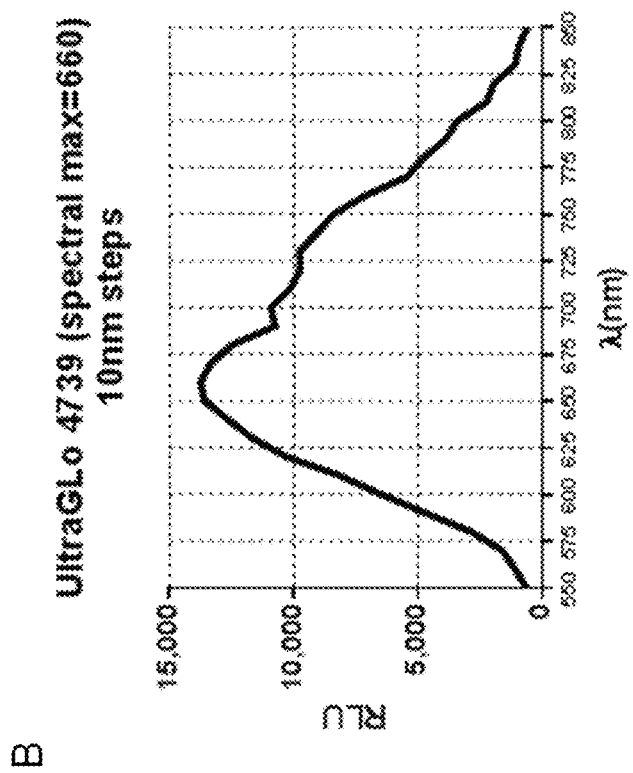
FIG. 3A and FIG. 3B illustrate spectral scans of Ultra-Glo™ Luciferase using PBI-4813 (FIG. 3A) and PBI-4739 (FIG. 3B) as substrates.
Figure 3A:
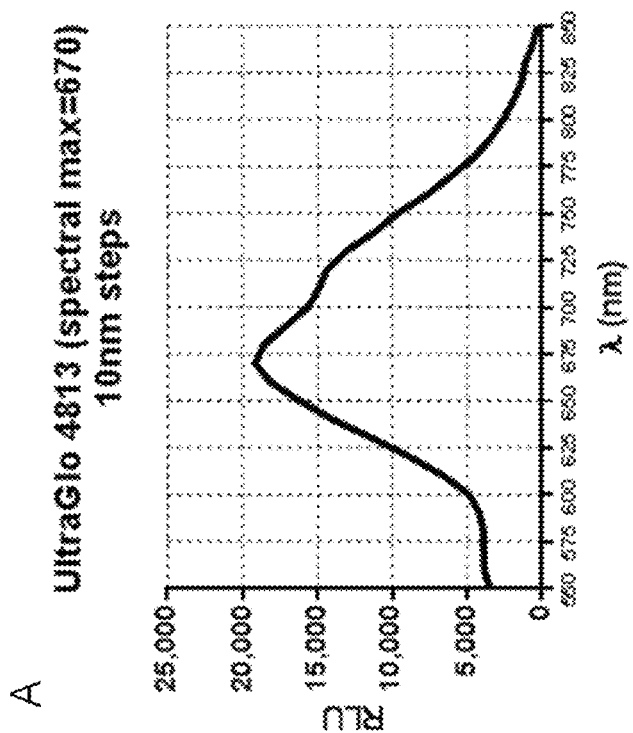
Figure 4A:
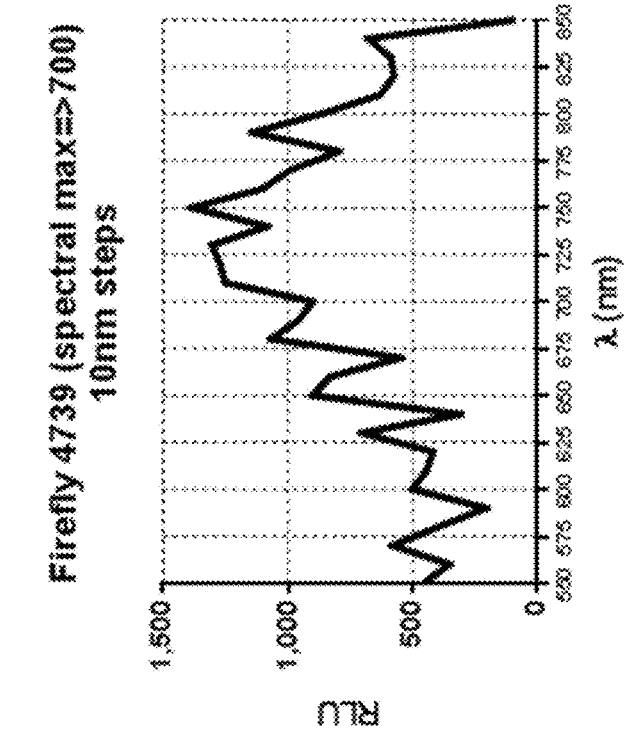
FIG. 4A and FIG. 4B illustrate spectral scans of Quanti-Lum® Recombinant Luciferase ("Firefly") using PBI-4813 (FIG. 4A) and PBI-4739 (FIG. 4B) as substrates.
Figure 4B:
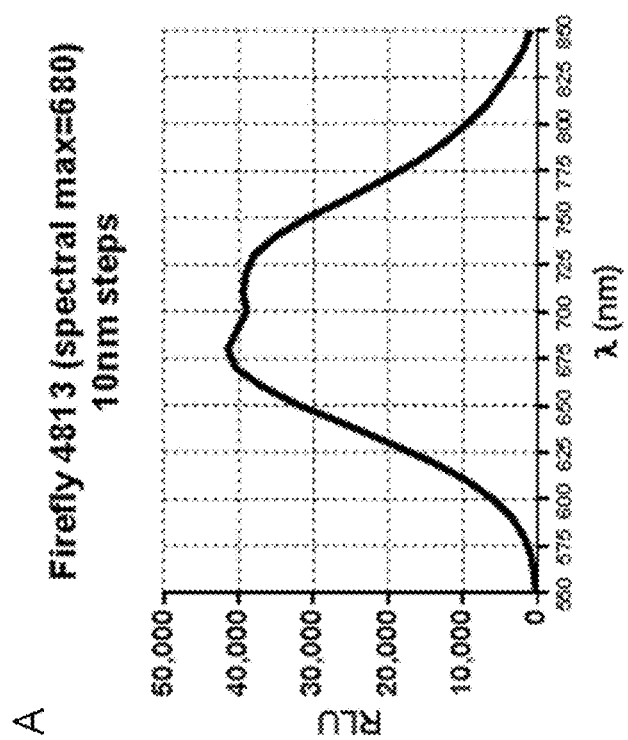

FIG. 2 provides the spectral data for Click Beetle Red Luciferase with PBI-4813 (A) and PBI-4739 (B), where the spectral maximum was 655 nm for PBI-4813 and 760 nm for PBI-4739. FIG. 3 provides the spectral data for UltraGlo® luciferase with PBI-4813 (A) and PBI-4739 (B), where the spectral maximum was 670 nm for PBI-4813 and 660 nm for PBI-4739. FIG. 4 provides the spectral data for QuantiLum® luciferase (firefly) with PBI-4813 (A) and PBI-4739 (B), where the spectral maximum was 680 nm for PBI-4813 and equal to or greater than 700 nm for PBI-4739.

Example 2

Library Screening

A library of Click Beetle Red variants was prepared using the Diversify™ PCR Random Mutagenesis Kit (Clontech) according to the manufacturer's instructions using pF4Ag-HT7-CBR as a template, i.e., CBR-HALOTAG® fusion protein. The library of variant DNA was cloned into the pF4Ag-HT7 (Promega) and transformed into 50 µL KRX competent cells (Promega Corporation). The cells were grown overnight on LB-ampicillin plates at 37° C.

Colonies were picked and grown overnight at 37° C. in 200 µL of M9-minimal media (1×M9 salts, 0.1 mM CaCl$_2$, 2 mM MgSO$_4$, 1 mM Thiamine-HCL, 1% gelatin, 0.2% glycerol and 100 µg/mL Ampicillin) in wells of 96-well plates. 10 µL of the overnight culture was diluted into 190 µL M9-minimal media and grown overnight at 37° C. 10 µL of the second overnight culture was diluted into 190 µL M9-minimal induction media (M9 minimal media+0.05% glucose and 0.02% rhamnose) and grown overnight at 25° C.

The cells were assayed via a robot. Briefly, 25 µL of cell culture was added to 25 µL of lysis buffer (50 mM HEPES pH 7.5, 0.3× Passive Lysis Buffer (PLB; Promega Corporation), 0.006 U RQ1 DNase1 (Promega Corporation)) and incubated for 3 min. 50 µL of Bright-Glo™ Assay Reagent (Promega Corporation) or PBI-4813 assay reagent (Bright-Glo™ Assay buffer+ATP (to 1 mM) and PBI-4813 (to 5 µM)) was added to lysed cells, and luminescence detected on Tecan Genios Pro (Table 1).

TABLE 1

| Sequence # | Sample | PBI-4813 Secondary screen | Bright-Glo ™ Secondary screen | Mutation AA |
|---|---|---|---|---|
| 45 | 91B4 | 3 | 1.5 | G251S |
| 8 | 18D5 | 2.6 | 1.30 | Y252C |
| 33 | 74C2 | 2.5 | 3 | I389F |
| 34 | 74F8 | 2.5 | NA | I131T, K146E, V285A, N401S |
| 27 | 46H5 | 2.4 | 1.30 | I389F |
| 32 | 74A8 | 2.4 | 2 | H218L, D471V |
| 26 | 44C9 | 2.2 | 1.00 | F87S, E453K, K484E |

TABLE 1-continued

| Sequence # | Sample | PBI-4813 Secondary screen | Bright-Glo ™ Secondary screen | Mutation AA |
|---|---|---|---|---|
| 1 | 01 E5 | 2.1 | 1.04 | L113Q, H218Y |
| 23 | 29C11 | 2.1 | 3.10 | Y252C, E501G |
| 9 | 19A3 | 2 | 1.60 | F87S |
| 30 | 63D9 | 2 | 1.10 | V431A |
| 16 | 09G5 | 1.9 | 1.80 | I131N |
| 29 | 63D7 | 1.9 | 1.10 | T528A |
| 21 | 15C7 | 1.8 | 1.20 | C335S |
| 25 | 40D8 | 1.8 | 3.70 | N83H |
| 38 | 75B4 | 1.73 | 2.6 | E253K, T363S |
| 15 | 16D2 | 1.7 | 2.00 | E82G, D412G |
| 43 | 87A4 | 1.7 | 2.2 | I79V, V394M |
| 47 | 95F4 | 1.7 | 1 | N211N |
| 4 | 13F1 | 1.6 | 2.60 | Y170C, S358P, T363A, K539R |
| 19 | 17D7 | 1.6 | 1.30 | I109V, K484M |
| 46 | 94F9 | 1.6 | 1.5 | I409T |
| 20 | 40B9 | 1.5 | 1.80 | L228P |
| 36 | 100D1 | 1.5 | 1.1 | V104D, K484R |
| 41 | 83E 2 | 1.5 | 1.2 | S444R |
| 42 | 85 A2 | 1.5 | 1.3 | F55V, E473A |
| 44 | 90B7 | 1.5 | 2.6 | V255D |
| 50 | 100B2 | 1.5 | 1.3 | M117T, K136N, N156D |
| 7 | 13G5 | 1.4 | 0.80 | E319G |
| 17 | 12D5 | 1.4 | 1.30 | F55L, Y496H |
| 39 | 79G9 | 1.4 | 3.2 | N130K, V255F |
| 48 | 96H5 | 1.4 | 2.5 | V455D |
| 3 | 09G7 | 1.3 | 2.70 | H34Y, N74S, R280S |
| 5 | 06G4 | 1.3 | 0.60 | K179S, H218Y, V516A |
| 6 | 13A3 | 1.3 | 0.84 | M393K, S444C, K457N |

Example 3

Click Beetle Red Mutation Combinations

Figure 5:
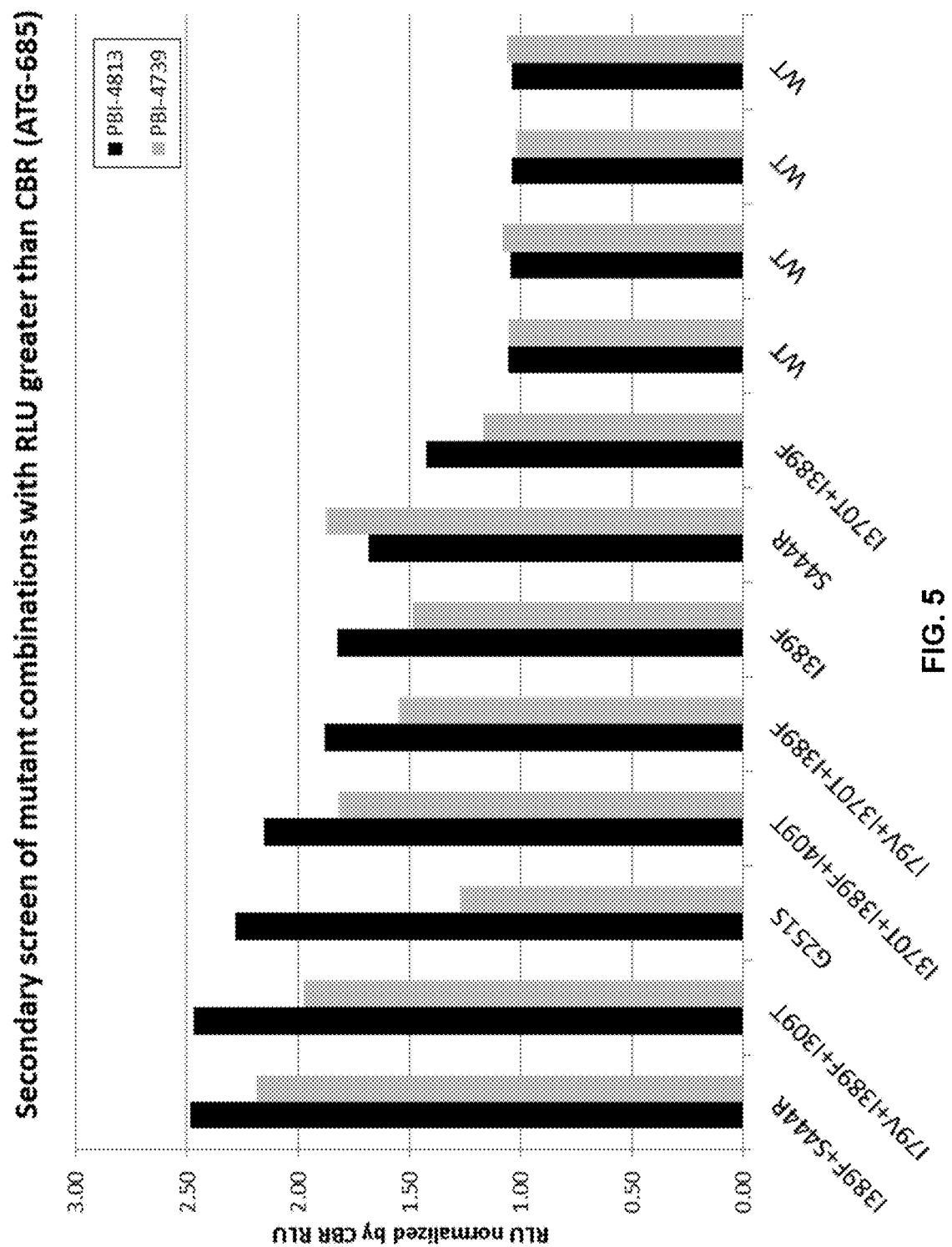
FIG. 5 illustrates the normalized luminescence of CBR variants and CBR ("WT") using PBI-4813 (dark bars) and PBI-4739 (light bars) as substrates.

Some of the mutations identified in the library screen outlined in Example 2 were combined to identify beneficial combinations of mutations. The mutations were introduced into the Click Beetle Red (CBR) luciferase (SEQ ID NO: 1) using the QuikChange Multi Site-Directed Mutagenesis Kit (Agilent). Variants were cloned, expressed and screened as described in Example 2. Table 2 and FIG. 5 list the variants and their fold change in luminescence over CBR luciferase with the substrate PBI-4813 or PBI-4739.

TABLE 2

| Sample sequence | Sample | PBI-4813 | PBI-4739 |
|---|---|---|---|
| I389F + S444R | ATG 1078 | 2.48 | 2.19 |
| I79V + I389F + I309T | 11G11 | 2.47 | 1.98 |
| G251S | ATG 1023 | 2.28 | 1.27 |
| I370T + I389F + I409T | 11A8 | 2.16 | 1.81 |
| I79V + I370T + I389F | 11C4 | 1.88 | 1.55 |
| I389F | ATG 1032 | 1.82 | 1.48 |
| S444R | ATG 1020 | 1.68 | 1.87 |
| I370T + I389F | 1G11 | 1.42 | 1.17 |
| WT | WT | 1.06 | 1.05 |
| WT | WT | 1.05 | 1.08 |
| WT | WT | 1.04 | 1.02 |
| WT | WT | 1.04 | 1.06 |

Example 4

Variants Tested in Mammalian Cells

Some of the variants identified in Examples 2 and 3 were screened for their performance in mammalian cells. DNA was prepared by Plasmid.com. HEK293 and HeLa cells were plated into wells of a 24-well plate at $0.05 \times 10^6$ cells/mL and grown overnight at 37° C. with $CO_2$. 2.2 µg variant DNA was mixed with 80 µL OptiMEM and 6.6 µL FuGENE® HD transfection reagent (Promega Corporation) and incubated at room temperature for 5 min. 25 µL of the DNA mixture was added to each well.

Figure 6:
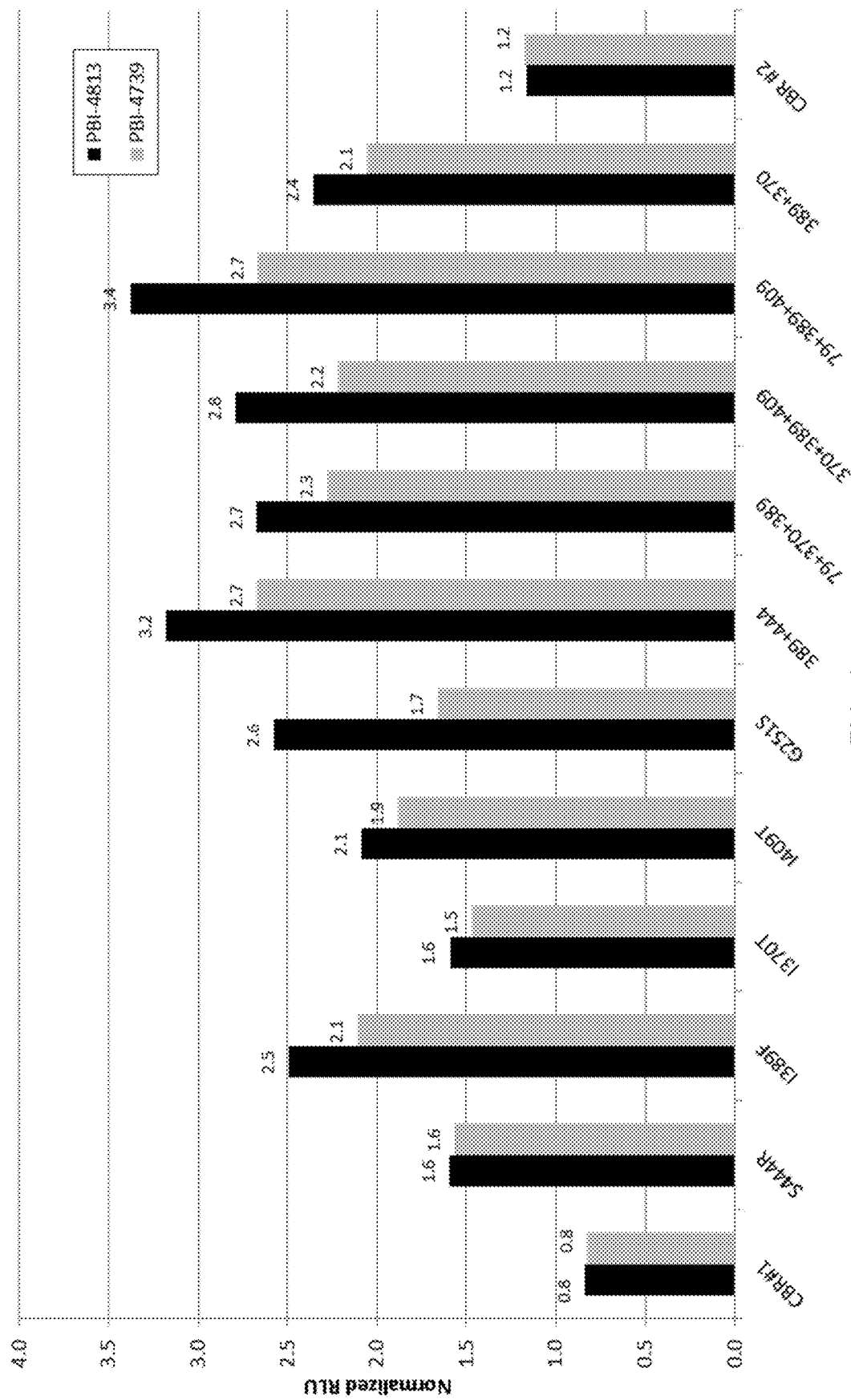
FIG. 6 illustrates the normalized luminescence of CBR variants and CBR in HEK293 cells using PBI-4813 (dark bars) and PBI-4739 (light bars) as substrates.
Figure 7:
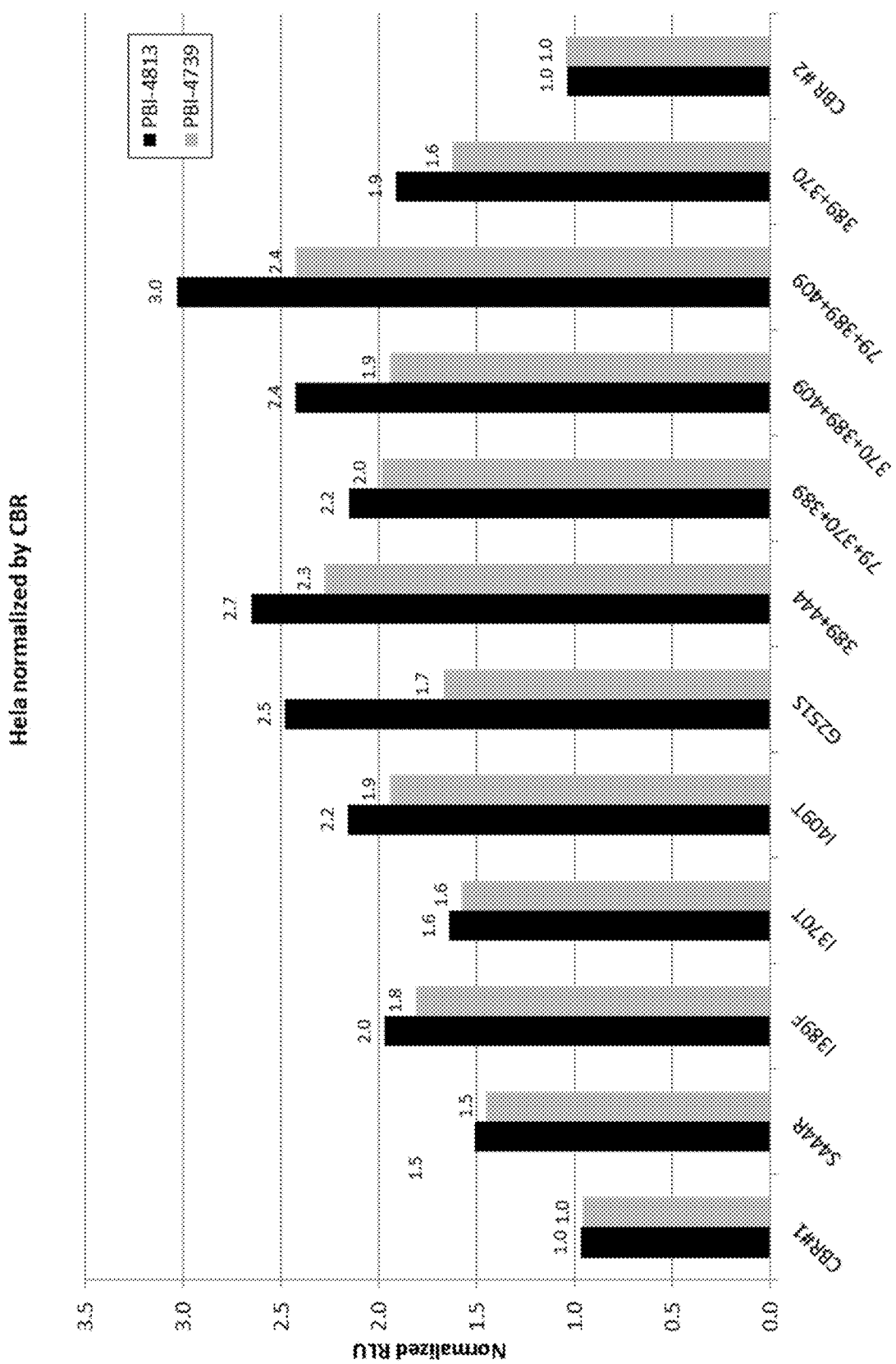
FIG. 7 illustrates the normalized luminescence of CBR variants and CBR in HeLa cells using PBI-4813 (dark bars) and PBI-4739 (light bars) as substrates.

After overnight incubation, the media was removed from the cells and 1 mL DPBS (Life Technologies) was added. The cells then underwent a freeze-thaw to generate cell lysates. 50 µL of the lysate was aliquoted into wells of a 96-deep well plate. 50 µL of assay reagent (20 µM of PBI-4813 or PBI-4739 in Bright-Glo™ Assay buffer containing 1 mM ATP) was added to the lysates, and luminescence was detected on an ImageQuant Luminescence of the variants was normalized to the average of two CBR samples (FIG. 6 and FIG. 7).

Example 5

Hydrogen Acceptor Mutagenesis Design

The amino acid differences between CBR and CBG99 contribute to color change, such as amino acid changes that have a major contribution, Y224V, H247S, and Q348H, and amino acid changes that have a minor contribution, I346N and T349S. At position 351, the amino acid is glycine in CBR and CBG99 and arginine in CBG68.

Efficient light emission from some red-shifted luciferin derivatives may require the presence of an amino acid that can serve as a hydrogen acceptor (H-acceptor) at an appropriate position in the active site of a CBR variant. For example, PBI-4739 may require an H-acceptor in the vicinity of its hydroxyl group. The computational experiments described below were performed using Discovery Studio software (Accelrys). A homology model of CBR was generated based on an X-ray structure template of the related *Luciola cruciata* luciferase complexed with DLSA (Protein Data Bank accession 2D1S). The PBI-4739 ligand was manually docked into this model to match the position of the DLSA ligand in 2D1S, and amino acid side chains within 5 Å of PBI-4739 were energy minimized. Molecular dynamics simulation was performed on CBR amino acid side chains within 5 Å of PBI-4739. Representative output conformations were used to examine in silico which CBR mutations (amino acid replacements) might provide the desired H-acceptor.

A first group of mutations was identified based on restructuring a network of interacting side chains. The targeted positions were in the vicinity of the PBI-4739 hydroxyl and at least partially exposed to solvent. Based on an alignment of representative beetle luciferases (firefly, click beetle, glowworm), it was determined that the side chains at these positions are conserved (E308), mostly conserved (R334 and T226) or variable (G351). Various combinations of side chains at these positions allowed formation of a stabilizing H-bond network that shields the ligand from solvent and bridges multiple secondary structure elements. The mutation combinations below were intended to provide different H-bond networks while at the same time recruited one of the side chains as an H-acceptor for interaction with hydroxyl of PBI-4739:

G351R+R334 (E, Q, D, N, H, S, T, C, Y)
G351K+R334 (E, Q, D, N, H, S, T, C, Y)
G351K+T226N+R334 (E, Q, D, N, H, S, T, C, Y)
G351E+E308R+R334 (E, Q, D, N, H, S, T, C, Y)
E308R+R334 (E, Q, D, N, H, S, T, C, Y)
T226N+R334 (E, Q, D, N, H, S, T, C, Y)

A second group of mutations was suggested based on targeting individual positions that can accommodate a variety of H-acceptors. Preference was given to substitutions that would not be accessible by a random mutagenesis approach, i.e. not accessible by single base substitutions:

T226 (N, Q, E, D, H, C, Y)
C310 (Q, E, N, D, H)
Q348 (H, E)
S281 (N, Q, H, Y)

Example 6

Hydrogen Acceptor Mutagenesis Variant Screen

A. Mutagenesis.

Hydrogen acceptor mutagenesis was performed using the QuikChange Multi Site-Directed Mutagenesis Kit (Agilent) as previously described using degenerate oligos specific to the amino acids listed below. The following variants were cloned and expressed as described in Example 2:

T226 (Q,N,E,D,H,C,Y)
C310 (Q,E,N,D,H)
S281 (Q,N,H,Y)
Q348 ((H,E)
G351R+R334 (E,Q,D,N,H,S,T,C,Y)
G351K+R334 (E,Q,D,N,H,S,T,C,Y)
G351+226N+R334 (E,Q,D,N,H,S,T,C,Y)
G351E+E308R+R334 (E,Q,D,N,H,S,T,C,Y)
E308R+R334 (C,Y)
T226N+R334 (E,D,S,T,C,Y)

B. Primary Screen.

1. One plate of clones was picked for each of the 10 sets of amino acid combinations described. These plates were then sequenced and assayed as previously described.

Figure 8:
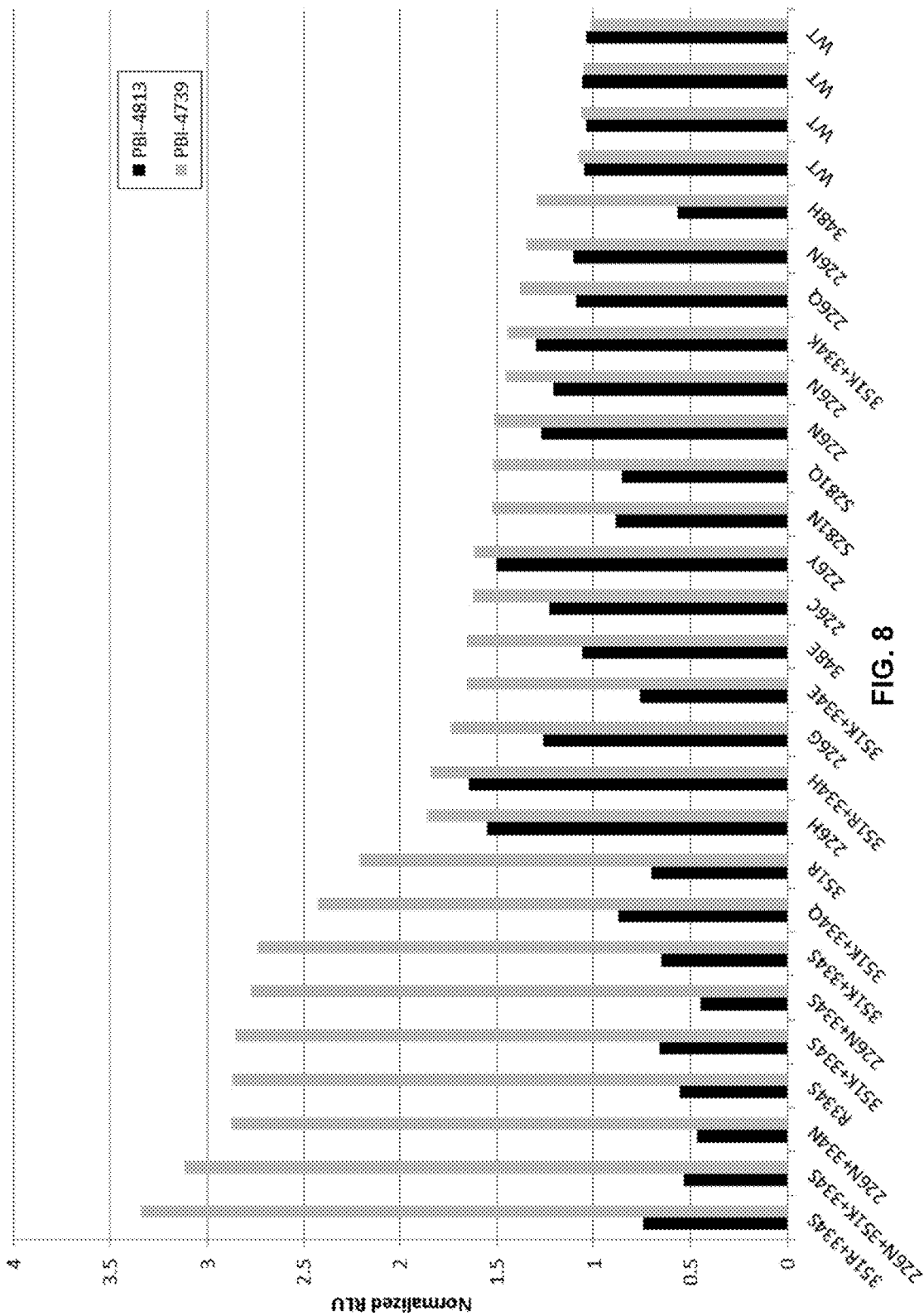
FIG. 8 illustrates the normalized luminescence of CBR variants and CBR ("WT") using PBI-4813 (dark bars) and PBI-4739 (light bars) as substrates.

2. Cell lysates were prepared from cells containing the variants listed in Table 3 by diluting 100 μL of induced culture with 100 μL of lysis buffer (0.3×PLB, 0.006 U RQ DNAse1) using a Tecan liquid handling robot. 50 μL of each cell lysate was assayed with either PBI-4813 or PBI-4739 (20 μM in Bright-Glo™ assay buffer containing 1 mM ATP), and luminescence detected on an ImageQuant CCD imager. Luminescence of the variants was normalized to CBR luciferase (FIG. 8).

C. Secondary Screen.

1. Hits from the primary screen were selected and then processed in a secondary screen. Each sample was assayed in quadruplicate using the same assay method described above for the primary screen.

2. The variants were assayed as described above in for the primary screen. Luminescence of the variants was normalized to CBR luciferase (Table 3).

TABLE 3

| Sample sequence | Sample | PBI-4813 | PBI-4739 |
| --- | --- | --- | --- |
| 351R + 334S | 5D5 | 0.7 | 3.3 |
| 226N + 351K + 334S | 7D1 | 0.5 | 3.1 |
| 226N + 334N | 10B2 | 0.5 | 2.9 |
| R334S | 5B9 | 0.6 | 2.9 |
| 351K + 334S | 6F9 | 0.7 | 2.9 |
| 226N + 334S | 10F2 | 0.4 | 2.8 |
| 351K + 334S | 6A1 | 0.6 | 2.7 |
| 351K + 334Q | 6G7 | 0.9 | 2.4 |
| 351R | 5E 2 | 0.7 | 2.2 |
| 226H | 1F9 | 1.6 | 1.9 |
| 351R + 334H | 5C4 | 1.6 | 1.8 |
| 226G | 1B3 | 1.3 | 1.7 |
| 351K + 334E | 6G3 | 0.8 | 1.7 |
| 348E | 4D1 | 1.1 | 1.7 |
| 226C | 1H3 | 1.2 | 1.6 |
| 226Y | 1A12 | 1.5 | 1.6 |
| S281N | S281N | 0.9 | 1.5 |
| S281Q | S281Q | 0.9 | 1.5 |
| 226N | 1G2 | 1.3 | 1.5 |
| 226N | 7G4 | 1.2 | 1.5 |
| 351K + 334K | 6C1 | 1.3 | 1.4 |
| 226Q | 1D5 | 1.1 | 1.4 |
| 226N | 1F8 | 1.1 | 1.4 |
| 348H | 4H1 | 0.6 | 1.3 |
| WT | WT | 1.0 | 1.1 |
| WT | WT | 1.0 | 1.1 |
| WT | WT | 1.1 | 1.1 |
| WT | WT | 1.0 | 1.0 |

Example 7

Combinations of H-Acceptor Mutagenesis and Library Screen Mutants

Figure 9:
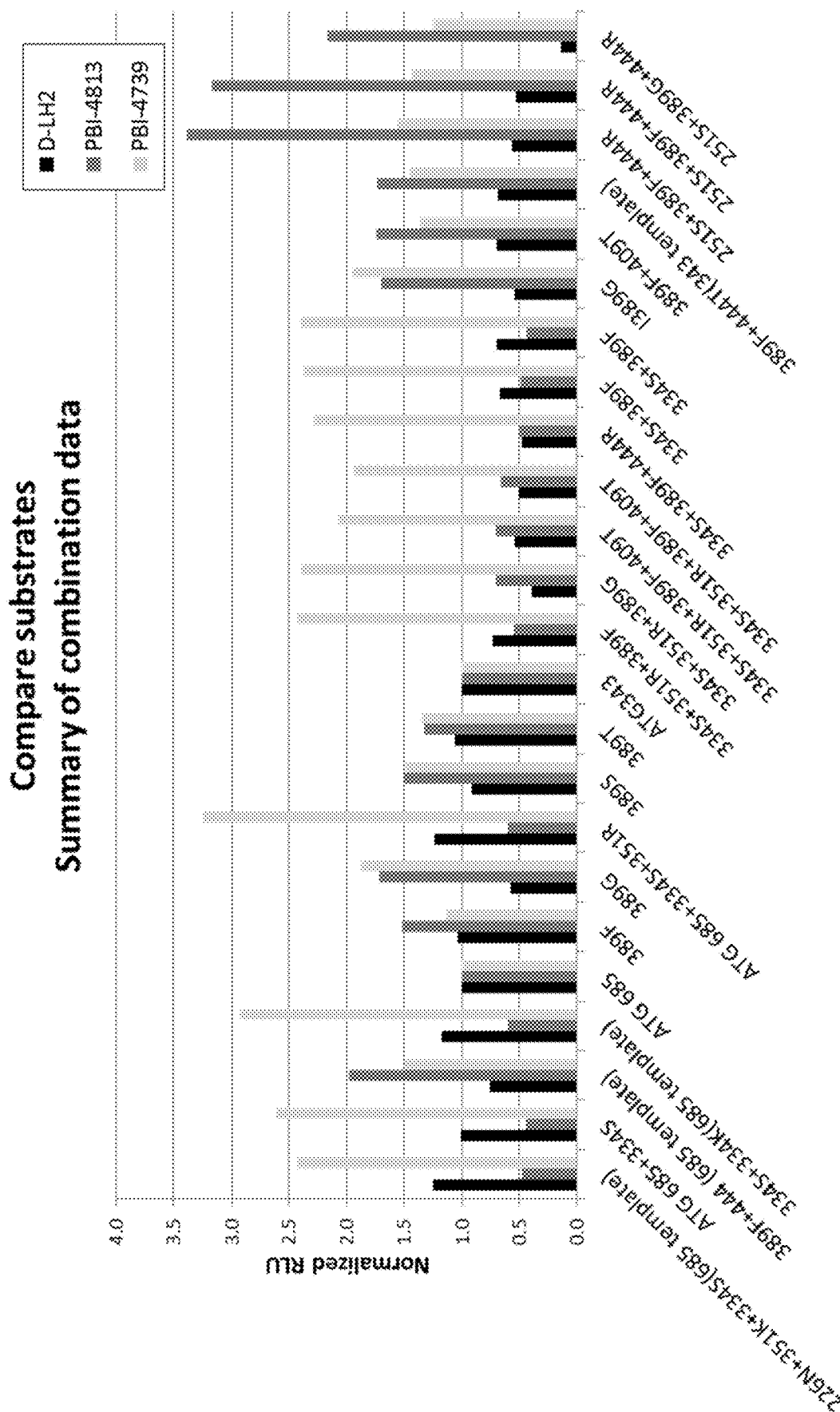
FIG. 9 illustrates the normalized luminescence of CBR variants and CBR ("ATG 685") using luciferin ("D-LH2"; dark bars), PBI-4813 (medium dark bars) and PBI-4739 (light bars) as substrates.

Combinations of the Hydrogen acceptor mutants identified in Example 6 were designed and prepared using the QuikChange Multi Site-Directed Mutagenesis Kit (Agilent). Variants were cloned and expressed as described in Example 2 except the template was pF4Ag-CBR. Variants were screened as described in Example 6. Luminescence of the variants using luciferin ("D-LH2"), PBI-4813, and PBI-4739 was normalized to CBR luciferase (Table 4 and FIG. 9).

TABLE 4

| Sequence | D-LH2 (luciferin) | PBI-4813 | PBI-4739 |
| --- | --- | --- | --- |
| 226N + 351K + 334S (685 template) | 1.2 | 0.5 | 2.4 |
| ATG 685 + 334S | 1.0 | 0.4 | 2.6 |

TABLE 4-continued

| Sequence | D-LH2 (luciferin) | PBI-4813 | PBI-4739 |
|---|---|---|---|
| 389F + 444 (685 template) | 0.8 | 2.0 | 1.5 |
| 334S + 334K(685 template) | 1.2 | 0.6 | 2.9 |
| ATG 685 | 1.0 | 1.0 | 1.0 |
| 389F (343 template) | 1.0 | 1.5 | 1.1 |
| 389G (343 template) | 0.6 | 1.7 | 1.9 |
| ATG 685 + 334S + 351R | 1.2 | 0.6 | 3.2 |
| 389S (343 template) | 0.9 | 1.5 | 1.5 |
| 389T (343 template) | 1.1 | 1.3 | 1.3 |
| ATG 343 | 1.0 | 1.0 | 1.0 |
| 334S + 351R + 389F (343 template) | 0.7 | 0.5 | 2.4 |
| 334S + 351R + 389G (343 template) | 0.4 | 0.7 | 2.4 |
| 334S + 351R + 389F + 409T (343 template) | 0.5 | 0.7 | 2.1 |
| 334S + 351R + 389F + 409T (343 template) | 0.5 | 0.7 | 1.9 |
| 334S + 389F + 444R (343 template) | 0.5 | 0.5 | 2.3 |
| 334S + 389F (343 template) | 0.7 | 0.5 | 2.4 |
| 334S + 389F (343 template) | 0.7 | 0.4 | 2.4 |
| I389G (343 template) | 0.5 | 1.7 | 2.0 |
| 389F + 409T (343 template) | 0.7 | 1.7 | 1.4 |
| 389F + 444T (343 template) | 0.7 | 1.7 | 1.4 |
| 251S + 389F + 444R (343 template) | 0.6 | 3.4 | 1.6 |
| 251S + 389F + 444R (343 template) | 0.5 | 3.2 | 1.4 |
| 251S + 389G + 444R (343 template) | 0.1 | 2.2 | 1.2 |

Example 8

Evaluation of Clone 1230 and 1240

Variant clones identified as ATG 1230 (CBR+389F+444R+251S) and ATG 1240 (CBR+334S+351R) were further evaluated for their luminescence, spectral property, Km and live cell kinetics with either PBI-4813 or PBI-4739. These variants were cloned and expressed as described in Example 2 except the template was pF4Ag-CBR, i.e., no HALOTAG®.

A. Luminescence with PBI-4813 and PBI-4739.

Figure 10:
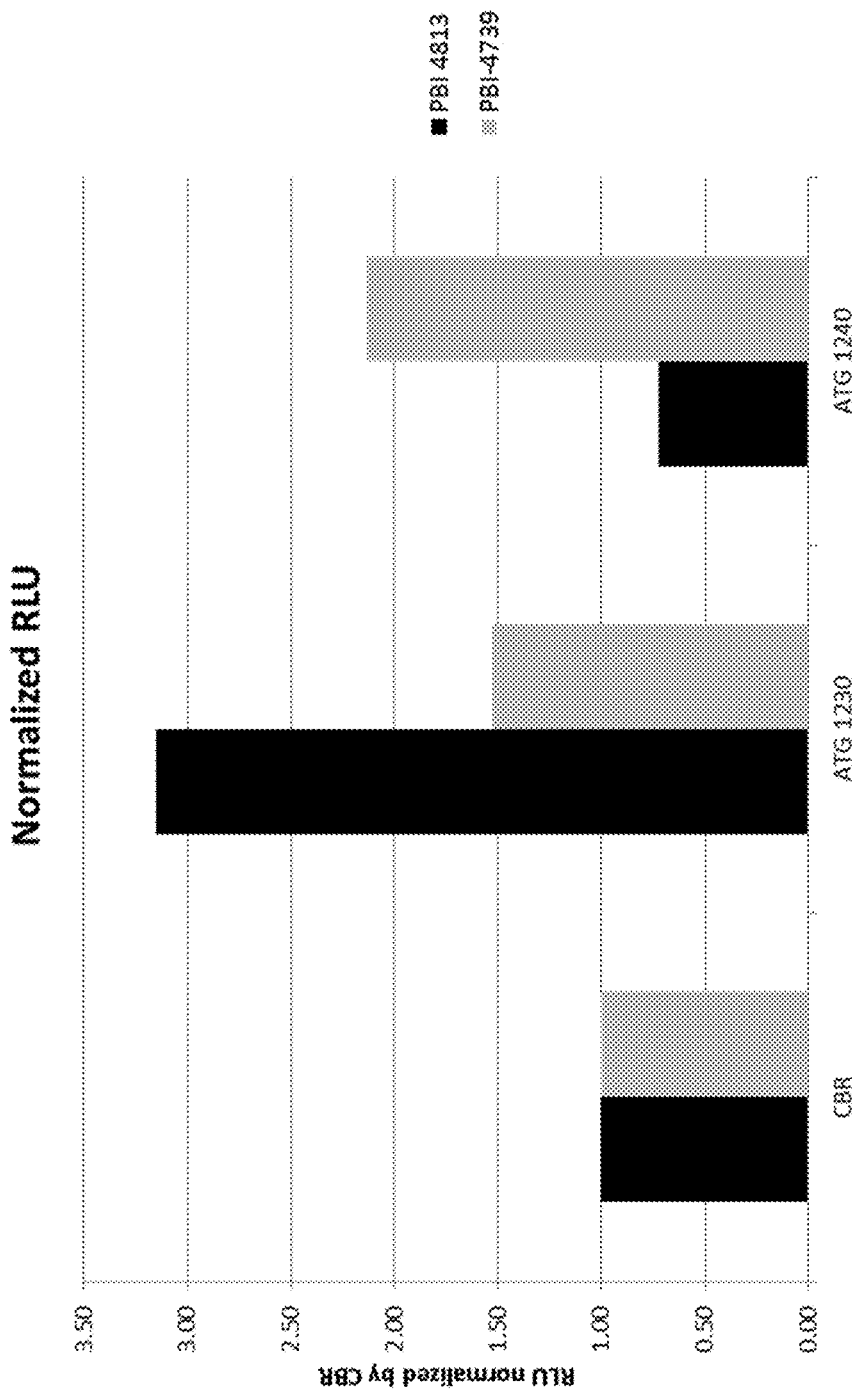
FIG. 10 illustrates the normalized luminescence of CBR variants ATG 1230 and ATG 1250 and CBR using PBI-4813 (dark bars) and PBI-4739 (light bars) as substrates.

Cell lysates of these variant clones were prepared and assayed for luminescence as described in Example 6. Luminescence was detected on a GloMax® Discover equipped with a red-sensitive photomultiplier tube (PMT) and compared to CBR luciferase (Table 5 and FIG. 10).

TABLE 5

| Clone | PBI 4813 | stdev | cv | PBI-4739 | stdev | cv | PBI-4813/PBI-4739 |
|---|---|---|---|---|---|---|---|
| CBR | 98,556 | 605.016 | 0.6% | 17,431 | 605.016 | 3% | 5.7 |
| ATG 1230 | 310,342 | 1133.41 | 0.4% | 26,595 | 1133.41 | 4% | 11.7 |
| ATG 1240 | 71,299 | 1614.31 | 2.3% | 37,169 | 1614.31 | 4% | 1.9 |

B. Spectral Measurements.

Figure 11B:
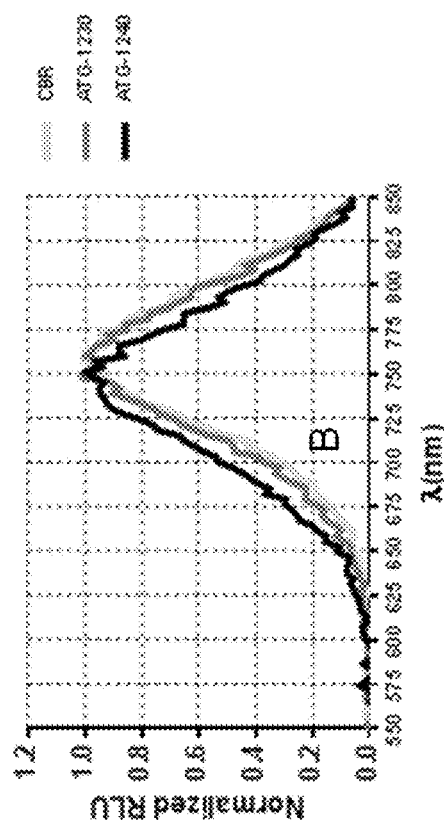
FIG. 11A and FIG. 11B illustrate the spectral properties of CBR variants ATG 1230 and ATG 1240 compared with CBR using PBI-4813 (FIG. 11A) and PBI-4739 (FIG. 11B) as substrates.
Figure 11A:
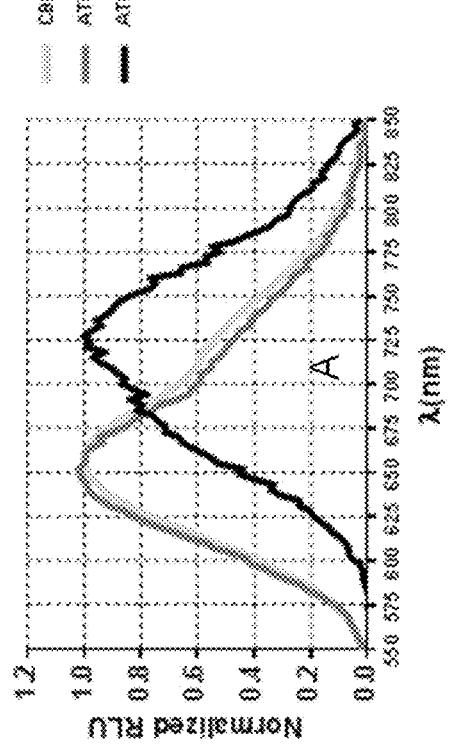

Purified ATG 1230 and ATG 1240 enzyme were prepared. CBR was diluted 1:10 in 0.3×PLB+0.1% Prionex. The enzymes were assayed in triplicate by adding 50 μL of enzyme to 50 μL of assay reagent (20 μM PBI-4813 or PBI-4739 in Bright-Glo™ Assay buffer containing 1 mM ATP). Luminescence was detected on a Tecan-M1000 using spectral scan mode (FIG. 11). Using PBI-4813 as substrate, ATG-1240 had a spectral max at about 725 nm while CBR and ATG-1230 had a spectral max of about 650 nm. Using PBI-4739 as substrate, ATG-1240 had a spectral max at about 750 nm while CBR and ATG-1230 had a spectral max of about 760 nm.

C. Km Titration.

Figures 12A, 12B:
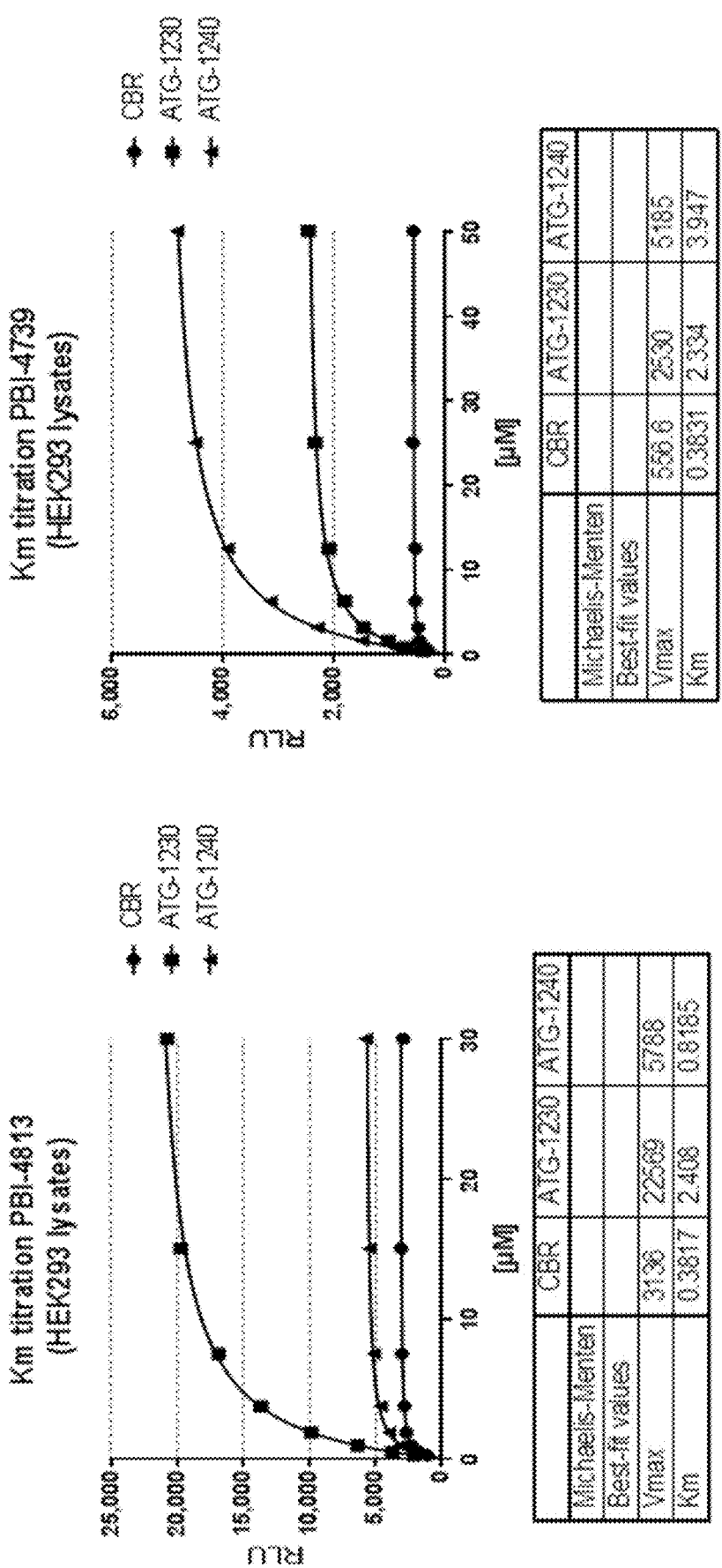
FIG. 12A and FIG. 12B illustrate the Km titration of CBR variants ATG 1230 and ATG 1240 compared with CBR for PBI-4813 (FIG. 12A) and PBI-4739 (FIG. 12B) as substrates.

Cell lysates of ATG 1230 and ATG 1240 expressed in HEK293 cells were prepared as described in Example 4. The cell lysates were then diluted 1:10 in 0.3×PLB+0.1% Prionex. Dilutions (2×) of each substrate (PBI-4813 or PBI-4739) were prepared in Bright-Glo™ Assay buffer containing 1 mM ATP. 50 μL of diluted cell lysate was assayed with 50 μL of each substrate assay solution. Luminescence was detected on the GloMax® Discover (FIG. 12). FIG. 12A and FIG. 12B show the relative Vmax (RLU) and Km (μM) values for ATG 1230 and ATG 1240 lysates using PBI-4813 and PBI-4739 as substrates. Because the enzyme concentration is not known for the lysates of for live cell titrations, Vmax as expressed as a velocity is not possible. Instead, the relative Vmax calculates the maximum brightness for each lysate with different substrates. The Km for PBI-4813 with CBR in the lysates was about 30× lower than CBR with D-luciferin. The Km for PBI-4813 with ATG1240 was about 5× lower than CBR with D-luciferin.

D. Live Cell Kinetics.

Figure 13:
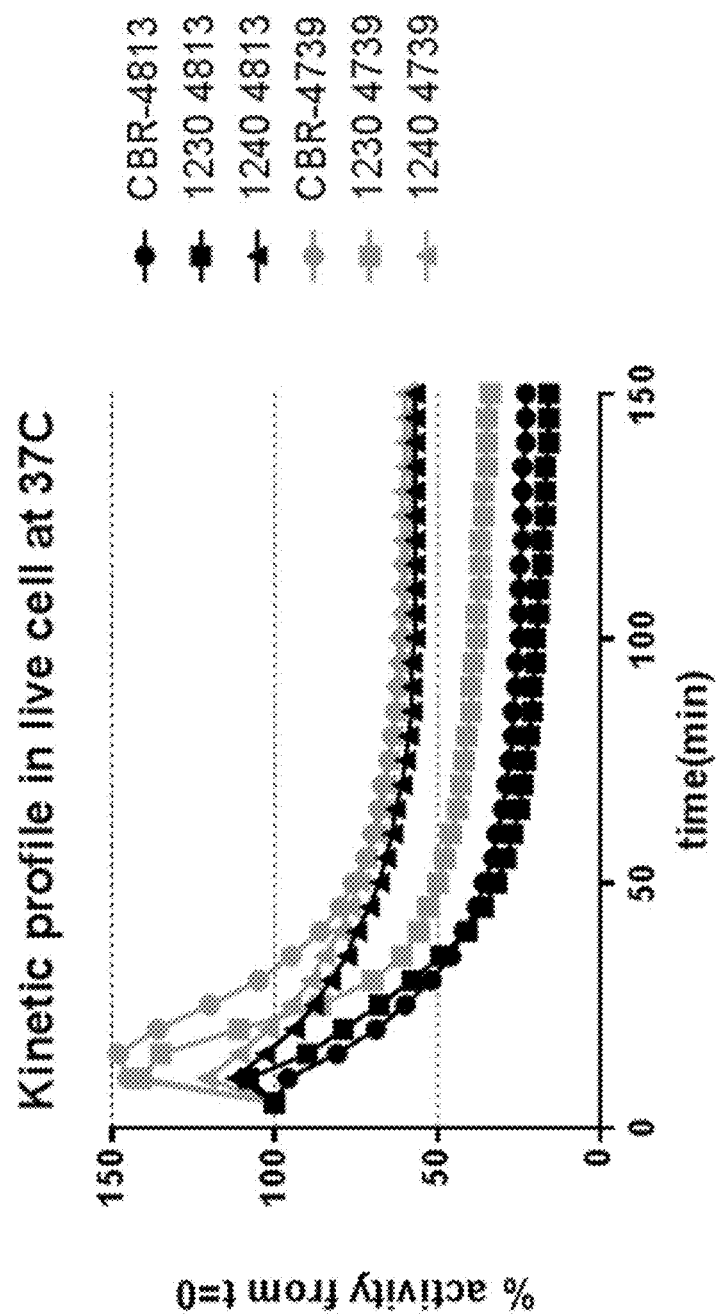
FIG. 13 illustrates the kinetic profile of CBR and CBR variants ATG 1230 and ATG 1240 in live cell at 37° C. using PBI-4813 and PBI-4739 as substrates.
Figure 14:
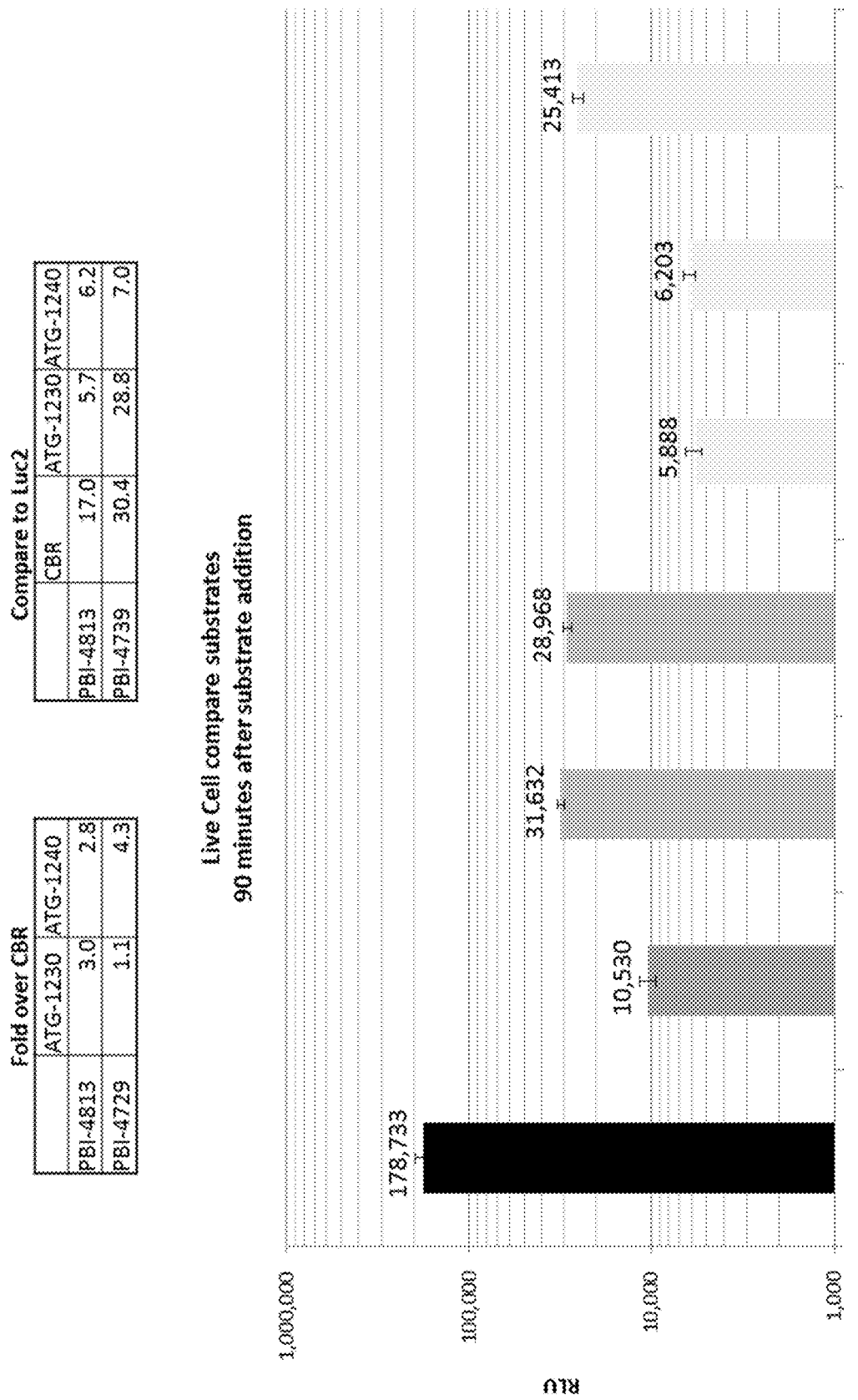
FIG. 14 illustrates the luminescence between CBR variants ATG 1230 and ATG 1240 compared with CBR using PBI-4813 (medium dark bars) and PBI-4739 (light bars) as substrates and with firefly luciferase ("Luc2") using luciferin ("D-LH2") as substrate (dark bar).

HEK293 cells were plated into wells of a 96-well plate at 10,000 cells/well for the kinetic read and 5,000 cells/well for luminescence detection. Cells were transfected (n=24 for each sample) using 17 μg of each DNA (ATG 1230 or ATG 1240) in a total of 776 μL of OptiMEM. 50 μL of FuGENE® HD (Promega Corporation) was then added, and the samples were incubated for 10 min at room temperature. 5 μL of DNA complex was added to 12 wells/clone to each plate. Plates were then incubated overnight at 37° C. with CO₂. Cells were assayed by first removing the growth media and replacing it with CO₂ independent media+0.5% FBS containing diluted substrate (100 μM of PBI-4813, 1 mM of PBI-4739, or 3 mM of D-luciferin). For the kinetic reading, the plate was incubated at room temperature for 5 min, and the kinetics were measured for 150 min at 37° C. on a GloMax® Discover (FIG. 13). For luminescence detection, the plate was incubated in a CO₂ incubator for 90 min, and luminescence was detected on a GloMax® Discover (FIG. 14).

HeLa cells were plated at 20,000 cells/well into wells of 96-well white assay plates and grown overnight. A transfection mixture was made containing 13 µg of CBR DNA and 40 µL FuGENE® HD in a total volume of 620 µL OptiMEM. The mixture was incubated at room temperature for 10 min. The cells were then transfected, in triplicate, with 5 µL of transfection complex and grown overnight.

Figures 21A, 21B:
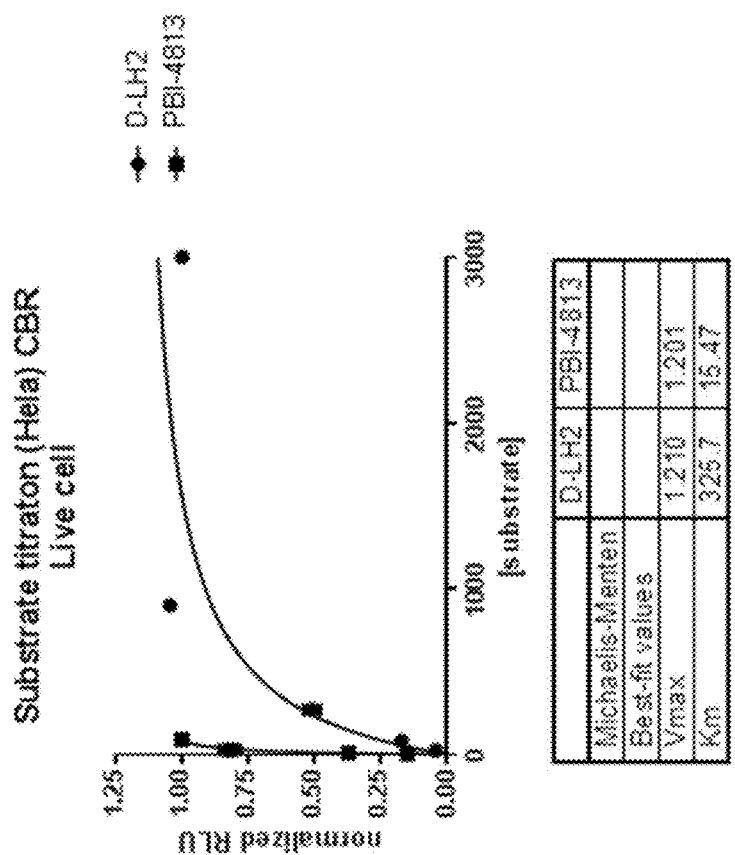
FIG. 21A and FIG. 21B illustrate the Km titration of CBR for PBI-4813 and D-luciferin ("D-LH2") as substrates in live HeLa cells.

The transfected cells were then assayed. 3× serial dilutions of D-luciferin starting at 3 mM in $CO_2$ independent media+0.5% FBS, and 3× serial dilutions of PBI-4813 starting at 0.3 mM were prepared. The growth media from the transfected cells was removed and replaced with one of the 3× serial diluted substrate containing media. The cells were incubated for 60 min at 37° C. Luminescence was detected on a GloMax®-Multi+luminometer (FIG. 21A and FIG. 21B). For CBR in live cells, the Km for PBI-4813 was about 20 times lower than the Km for D-luciferin.

HEK293T cells were plated at 15,000 cells/well into wells of 96-well white assay plates and grown overnight. A transfection mixture was made containing 13 µg of CBR DNA and 40 µL FuGENE® HD in a total volume of 620 µL OptiMEM. The mixture was incubated at room temperature for 10 min. The cells were then transfected, in triplicate, with 5 µL of transfection complex and grown overnight.

Figure 22:
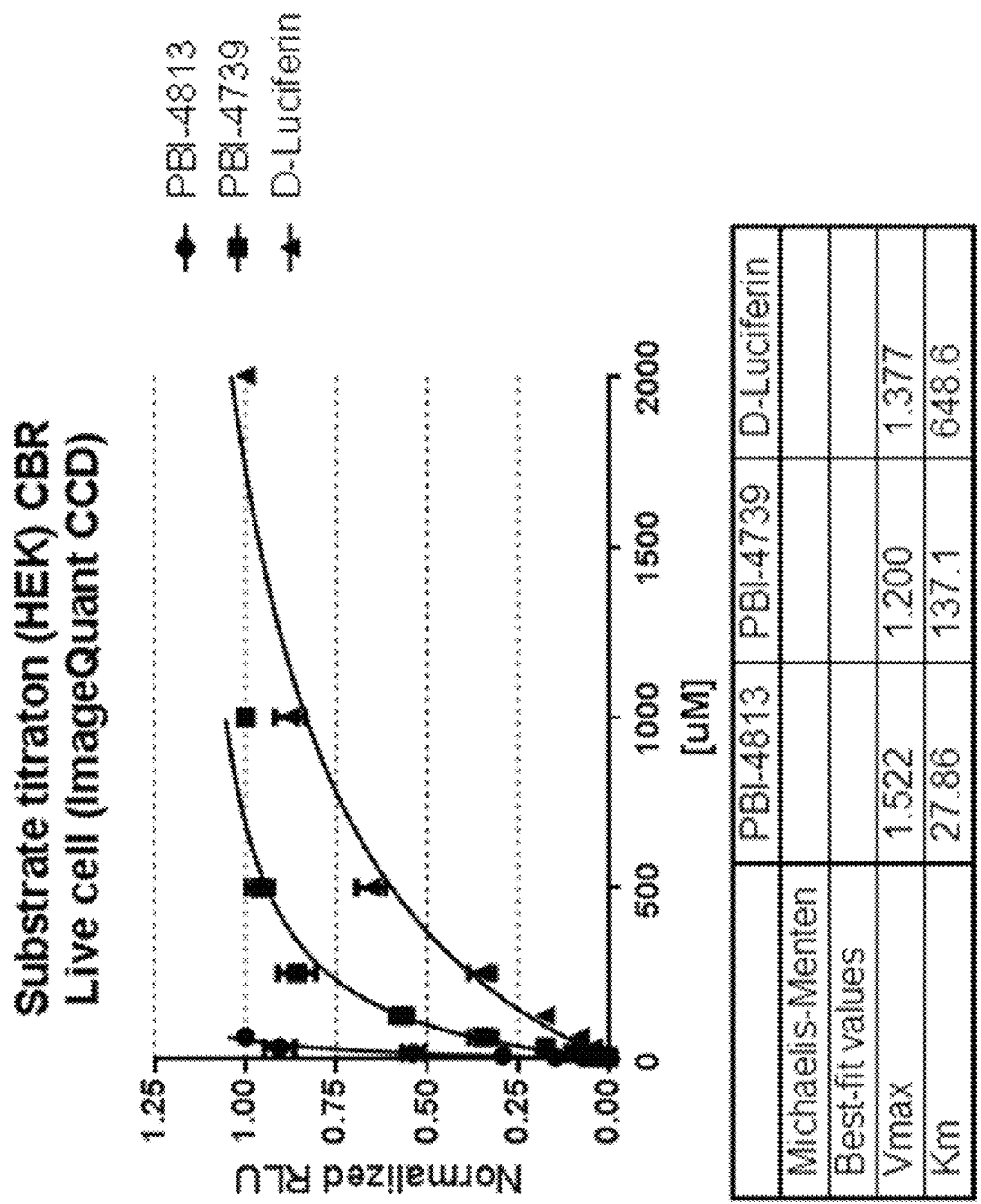
FIG. 22 illustrates the Km titration of CBR for PBI-4813, PBI-4739, and D-luciferin as substrates in live HEK293T cells.

The transfected cells were then assayed. 2× serial dilutions of D-luciferin starting at 2 mM in $CO_2$ independent media+0.5% FBS, and 2× serial dilutions of PBI-4813 and PBI-4739 starting at 1 mM were prepared. The growth media from the transfected cells was removed and replaced with one of the 3× serial diluted substrate containing media. The cells were incubated 60 min at 37° C., and the cells were imaged on a ImageQuant CCD imager (FIG. 22). For CBR, the Km of PBI-4739 was about 5 times lower relative to D-luciferin while the Km of PBI-4813 was about 23 times lower relative to D-luciferin.

HEK293T cells were plated at 15,000 cells/well into wells of 96-well white assay plates and grown overnight. A transfection mixture was made containing 6.6 µg of CBR or ATG-1240 DNA and 20 µL FuGENE® HD in a total volume of 310 µL OptiMEM. The mixture was incubated at room temperature for 10 min. The cells were then transfected, in triplicate, with 5 µL of transfection complex and grown overnight.

Figure 23B:
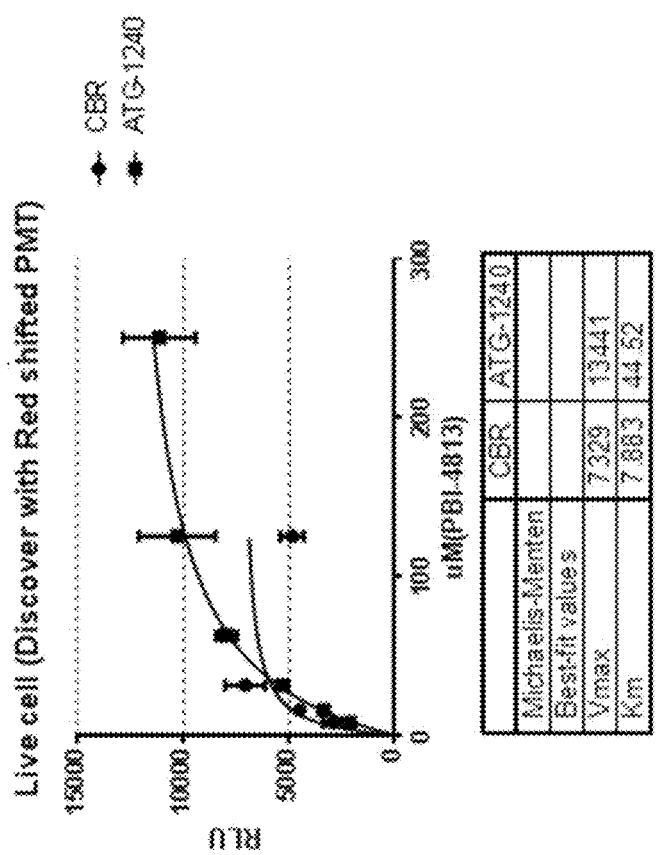
FIG. 23A and FIG. 23B illustrate the Km titration of CBR variant ATG 1230 compared with CBR for PBI-4813 (FIG. 23A) and PBI-4739 (FIG. 23B) as substrates in live HEK293T cells.
Figure 23A:
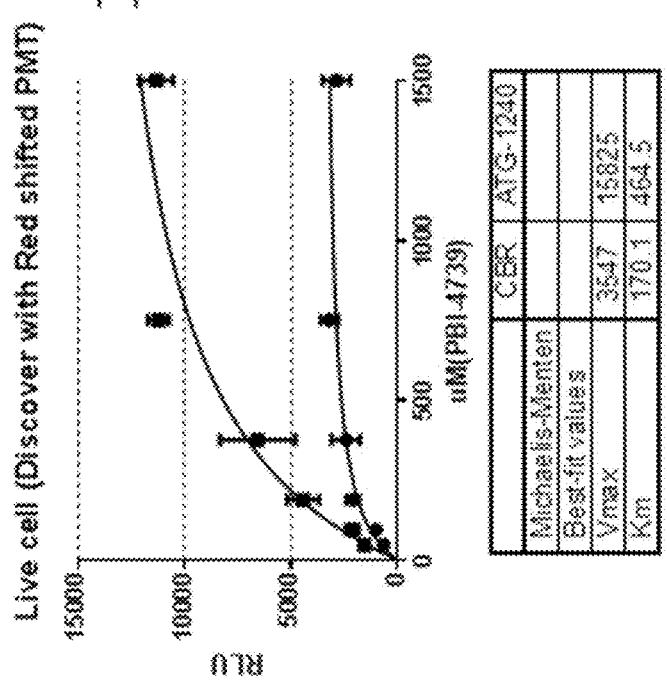

The transfected cells were then assayed. 2× serial dilutions of PBI-4813 and PBI-4739 starting at 2 mM in $CO_2$ independent media+0.5% FBS were prepared. The growth media from the transfected cells was removed and replaced with one of the serial diluted substrate containing media. The cells were incubated 60 min at 37° C., and luminescence detected on a modified GloMax® Discover luminometer containing a red shifted PMT (see FIG. 23A and FIG. 23B). The Km of ATG 1240 was about 5 times higher than the Km of CBR with PBI-4813. The Km of ATG 1240 was about 3 times higher than the Km of CBR with PBI-4739.

Example 9

Secondary Library Screen Using ATG 1240 as a Template

A random clone library was prepared as described in Example 2 using ATG 1240 as a template. The variants were then cloned into pF4Ag (no HT7). The library was screened as follows (50 plates total):

i. Primary Screen.

Cells were grown as described in Example 2. Cell lysates were prepared by diluting 100 µL of induced culture with 100 µL of lysis buffer (0.3×PLB+0.006 U RQDNAseI) using a Tecan liquid handling robot. 50 µL of each cell lysate was then assayed with either PBI-4813 or PBI-4739. (20 µM substrate in Bright-Glo™ assay buffer containing 1 mM ATP). Luminescence was detected on a GloMax® Discover.

ii. Secondary Screen.

Cells from each hit in the primary screen were streaked onto new plates and grown overnight. Colonies were picked in quadruplicate and cultures were grown as described in Example 2. 50 µL of each cell lysate was assayed with 50 µL of BrightGlo™ assay buffer containing 1 mM ATP and 30 µM PBI-4813 or 50 µM PBI-4739. Luminescence was detected on a GloMax® Discover Multimode Detection System (Table 6). The variants in this library were identified as having on average between 2-3 mutations per gene.

TABLE 6

| Sequence | Sample | PBI-4813 | PBI-4739 |
|---|---|---|---|
| S51N + I119F | 23E 4 | 2.5 | 5.0 |
| I119T + N329D + N400D | 5C4 | 1.2 | 1.5 |
| M393L | 14B12 | 1.1 | 1.5 |
| R4H + I229V | 8D6 | 1.6 | 1.4 |
| D352N | 2C11 | 1.4 | 1.3 |
| H16Q + M73T + I89V + I109N + E489V | 8A8 | 1.4 | 1.3 |
| D47E, I109N, G200G | 48A2 | 1.22 | 1.26 |
| L537W | 16E 8 | 1.7 | 1.2 |
| V186A + I439V | 20D7 | 1.9 | 1.2 |
| L350P, Q535H | 38F8 | 1.34 | 1.17 |
| I439V | 3C2 | 1.7 | 1.2 |
| F420F, V503M | 32C8 | 1.29 | 1.16 |
| K337E, V431A | 48A4 | 1.56 | 1.15 |
| I119F, G251I, I346N | 30A12 | 0.69 | 1.12 |
| WT | ATG-1240 | 1.2 | 1.1 |
| L537W | 43 E8 | 1.12 | 1.09 |
| M73K, Y508C | 49F9 | 1.19 | 1.08 |
| L537W | 29H1 | 1.04 | 1.07 |
| N156K + Q445H | 4D11 | 1.4 | 1.1 |
| WT | ATG-1240 | 1.01 | 1.05 |
| Y422C + E531G | 2D4 | 1.4 | 1.0 |
| WT | ATG-1240 | 1.0 | 1.0 |
| WT | ATG-1240 | 0.9 | 1.0 |
| WT | ATG-1240 | 1.01 | 0.99 |
| WT | ATG-1240 | 1.02 | 0.99 |
| I124V, G225S | 40G2 | 0.97 | 0.97 |
| WT | ATG-1240 | 0.97 | 0.97 |
| WT | ATG-1240 | 0.9 | 0.9 |
| K72E, N133D, F144L, I409T | 49E 3 | 1.29 | 0.86 |
| Y52C | 35H1 | 1.39 | 0.82 |
| E437G, I390I | 43C10 | 0.99 | 0.80 |
| E437G, I390I | 45H2 | 0.95 | 0.79 |
| V234A, V467A | 46H12 | 0.99 | 0.67 |

Example 10

Insertion Mutagenesis: Engineering the Click Beetle Red-Luciferin Binding Pocket The goal was to significantly increase the light emission from Click Beetle Red (CBR) mutant(s) with the red-shifted substrates, e.g., PBI-4739 (more red and less soluble), PBI-4813 (brighter, possible substrate inhibition). The previously described random mutagenesis and site-directed mutagenesis yielded about 3-fold improvement in light emission.

Approach 1 was to perform cassette mutagenesis of contiguous residue stretches in the vicinity of luciferin ligand binding. Approach 2 was to attempt to expand the luciferin ligand binding pocket by inserting single Ala residues at specific sites.

Suitable insertion sites were identified by visual inspection of the previously generated 3D structure model of CBR with PBI-4739, as described in Example 5. Additional information on sites that tolerate insertions/deletions was obtained from an alignment of diverse beetle luciferase protein sequences (e.g., firefly, click beetle, and glowworm) retrieved from the public GenBank and UniProt databases. Further information was obtained from superimposing 3D structures of luciferases (e.g. firefly luciferase with ligand, PDB accession 2D1S) and related non-luciferases (e.g. CoA-ligase with ligand, PDB accession 3N12) and examining how sequence changes such as insertions/deletions allow secondary structure elements move to accommodate different ligands in the binding pocket.

Based on combined analyses of the 3D structures and protein sequence alignment, several sites in CBR were identified as targets for insertion mutagenesis. Single Ala residues were inserted after these positions (bolded and underlined in FIG. 18) in CBR.

Variant constructs generated by the insertion mutagenesis were prepared by Gene Dynamics. Cells from each variant clone were grown overnight onto LB-ampicillin plates, and colonies picked in quadruplicate and grown in cultures as described in Example 6. Cell lysates were prepared as previously described, and 50 µL of cell lysate was assayed with 50 µL of Bright-Glo™ assay buffer containing 1 mM ATP and 30 µM PBI-4813 or PBI-4739. Luminescence was detected on a GloMax® Discover and normalized to CBR (Table 7).

TABLE 7

| Neutral insertion mutations | | |
|---|---|---|
| Sample | PBI-4813 | PBI-4739 |
| 38 | 0.9 | 0.8 |
| 39 | 0.9 | 1.0 |
| 40 | 0.9 | 1.0 |
| 144 | 0.9 | 0.8 |
| 145 | 0.9 | 0.9 |
| 146 | 1.0 | 0.9 |
| 147 | 1.0 | 1.1 |
| 171 | 0.9 | 0.9 |
| 173 | 1.0 | 0.9 |
| 227 | 1.0 | 0.9 |
| 264 | 0.6 | 1.1 |
| 265 | 0.8 | 1.1 |
| 350 | 1.1 | 0.8 |
| 351 | 1.2 | 1.0 |

Note:
("A" inserted at designated position)

Example 11

Recombination of ATG 1240 Library Mutants

Figure 15:
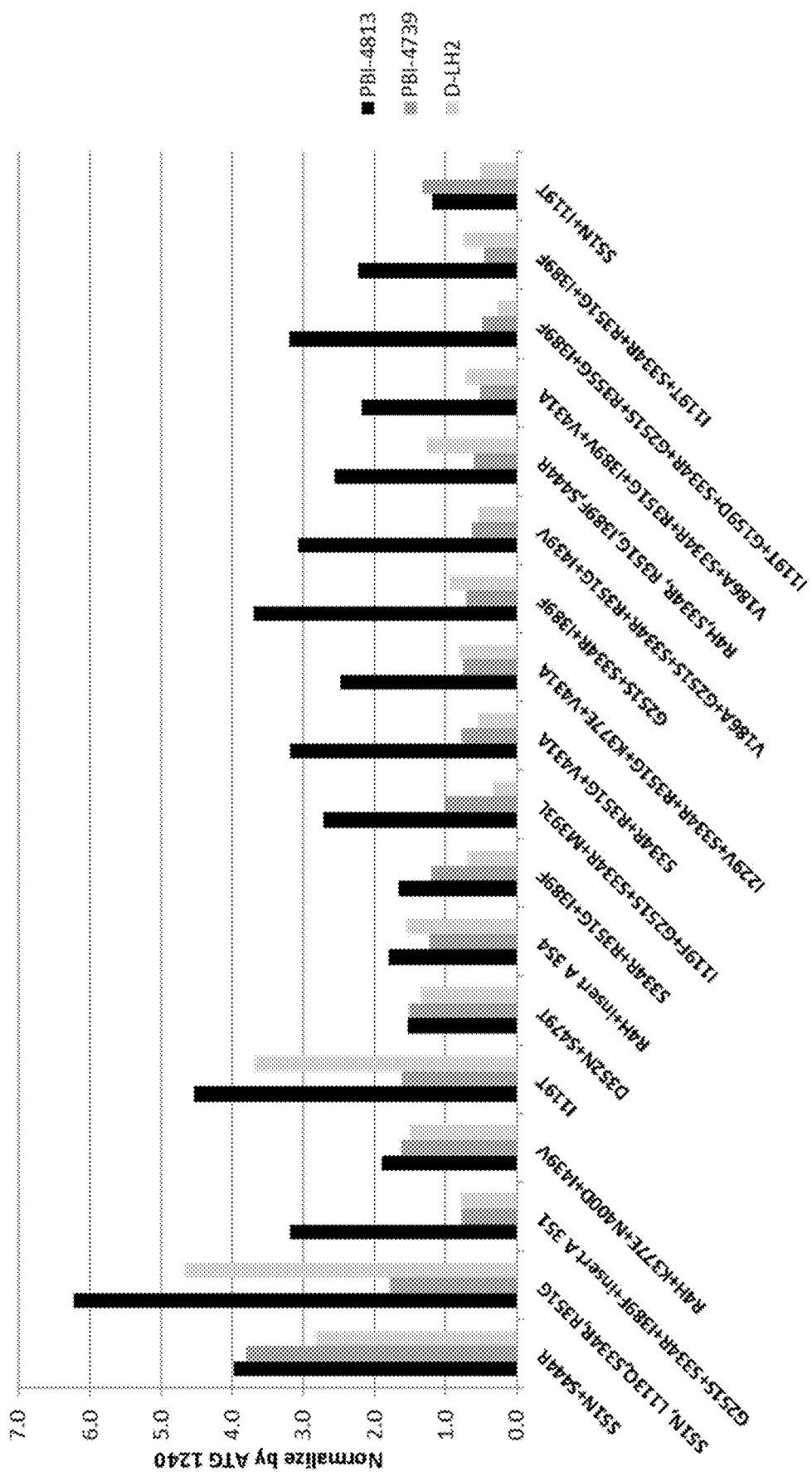
FIG. 15 illustrates the normalized luminescence of CBR variants using luciferin ("D-LH2"; light bars), PBI-4813 (dark bars), and PBI-4739 (medium dark bars) as substrates.

Combinations of the ATG 1240 library mutants identified in Example 9 were designed and prepared using DNA shuffling (Stemmer (1994) PNAS USA 91:10747-10751). Briefly, a library of mutant genes was created via DNA shuffling. The mutant genes were then cloned into the pF4Ag vector and screened as described in Example 6. Luminescence was detected on a GloMax® Discover Multimode Detection System and normalized to ATG-1240 luciferase (Table 8 and FIG. 15).

TABLE 8

| Sample | Sequence | PBI-4813 | PBI-4739 | D-LH2 |
|---|---|---|---|---|
| 5G5 | S51N + S444R | 4.0 | 3.8 | 2.8 |
| 8D10 | S51N, L113Q, S334R, R351G | 6.2 | 1.8 | 4.7 |
| 18C9 | G251S + S334R + I389F + insert A 351 | 3.2 | 0.8 | 0.8 |
| 3B9 | R4H + K377E + N400D + I439V | 1.9 | 1.6 | 1.5 |
| 8C10 | I119T | 4.5 | 1.6 | 3.7 |
| 9F10 | D352N + S479T | 1.5 | 1.5 | 1.3 |
| 11D10 | R4H + insert A 354 | 1.8 | 1.2 | 1.5 |
| 17A4 | S334R + R351G + I389F | 1.7 | 1.2 | 0.7 |
| 10A7 | I119F + G251S + S334R + M393L | 2.7 | 1.0 | 0.4 |
| 18C9 | S334R + R351G + V431A | 3.2 | 0.8 | 0.5 |
| 4H12 | I229V + S334R + R351G + K377E + V431A | 2.5 | 0.8 | 0.8 |
| 7G5 | G251S + S334R + I389F | 3.7 | 0.7 | 0.9 |
| 10 E5 | V186A + G251S + S334R + R351G + I439V | 3.1 | 0.6 | 0.5 |
| 6D7 | R4H, S334R, R351G, I389F, S444R | 2.6 | 0.6 | 1.3 |
| 8A1 | V186A + S334R + R351G + I389V + V431A | 2.2 | 0.5 | 0.7 |
| 4C8 | I119T + G159D + S334R + G251S + R355G + I389F | 3.2 | 0.5 | 0.3 |
| 1E 2 | I119T + S334R + R351G + I389F | 2.2 | 0.5 | 0.7 |
| 10C11 | S51N + I119T | 1.2 | 1.3 | 0.5 |

Example 12

Live Cell Substrate Titration

HEK293 cells were plated into wells of a 96-well plate at 5,000 cells/well and grown overnight. Cells were then transfected (n=24 for each sample) using 17 µg of ATG 1240 DNA in a total of 776 µL of OptiMEM. 50 µL of FuGENE® HD (Promega Corporation) was then added, and the samples incubated for 10 min at room temperature. 5 µL of DNA complex was added to 18 wells/sample to each plate. Plates were then incubated overnight at 37° C. with $CO_2$.

Figure 16A:
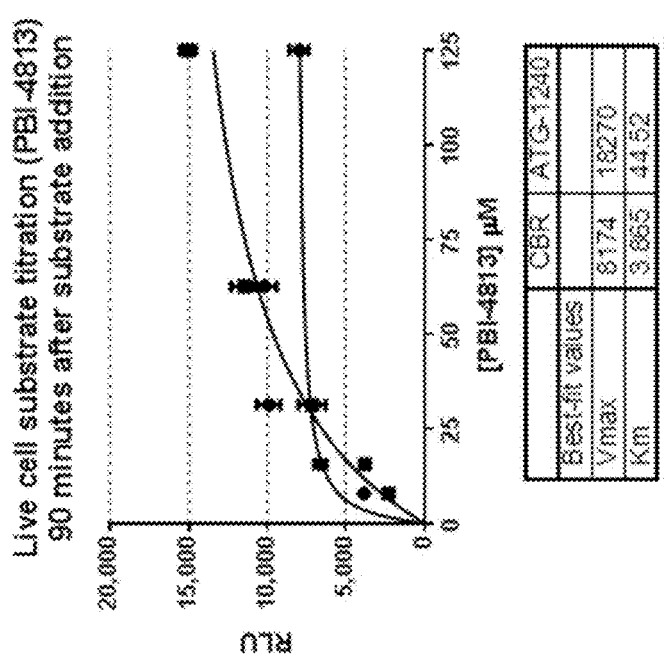
FIG. 16A and FIG. 16B illustrate live cell substrate titration of CBR variant ATG 1240 compared to CBR using PBI-4739 (FIG. 16A) and PBI-4813 (FIG. 16B) as substrates.
Figure 16B:
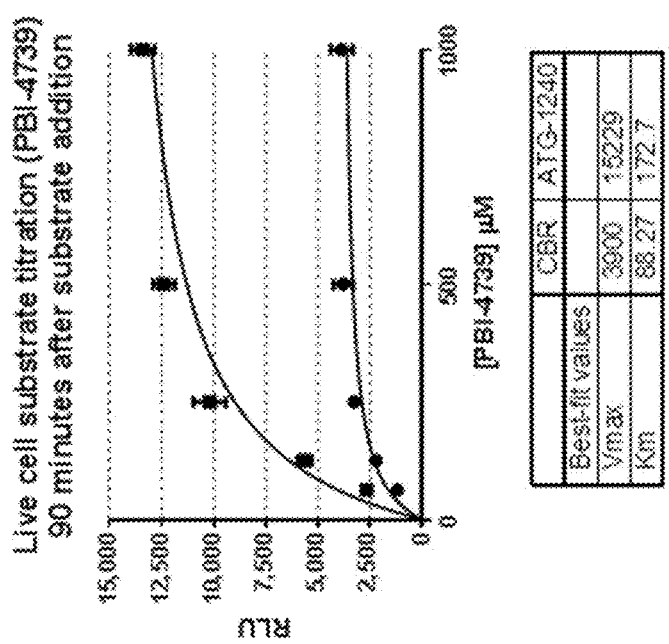

Cells were assayed by first removing the growth media and replacing it with $CO_2$ independent media+0.5% FBS containing 2× diluted substrate (PBI-4813 or PBI-4739). 100 µL of each diluted substrate was added in triplicate to the transfected cells and incubated for 60 min. Luminescence was detected on a GloMax® Discover (FIG. 16).

Example 13

Mimicry of Tissue Attenuation Using Long Pass Filters

This example demonstrates how much light is produced in cells transfected with Luc2 (*Photinus pyralis* luciferase) and assayed with D-luciferin compared to ATG 1240 assayed with D-luciferin, PBI-4813 or PBI-4739 using various long pass cut-off filters.

A transfection complex was prepared by diluting ATG 1240 DNA or Luc2 DNA (pF4Ag-Luc2) to 100 ng/µL, and then 2× serial dilutions prepared in 50 ng/µL pGEM carrier DNA. 40 µL of the diluted DNA was the mixed with 160 µL phenol red free OptiMEM and 16 µL of FuGENE® HD and incubated for 20 min. 5 µL of each transfection complex was added to wells of a 96-well black assay plates and then 100 µL of diluted HEK293T cells (200,000/mL in DMEM+10% FBS) was added. The cells were grown overnight at 37° C. with $CO_2$.

To assay the cells, 4 mM D-luciferin, 2 mM PBI-4813 and 2 mM PBI-4739 substrate solutions were prepared in DMEM+10% FBS. 100 µL of the D-luciferin solution was added to cells expressing Luc2 and ATG 1240, and 100 µL of PBI-4813 or PBI-4739 solution was added to ATG 1240 expressing cells. Samples were incubated for 10 min at 37° C., and luminescence detected on GloMax® Discover (heated to 37° C.) with no filter, 610 nm Long Pass (LP) filter, 665 nm LP filter, 695 nm LP filter, 720 nm LP filter or 760 nm LP filter.

Figure 17:
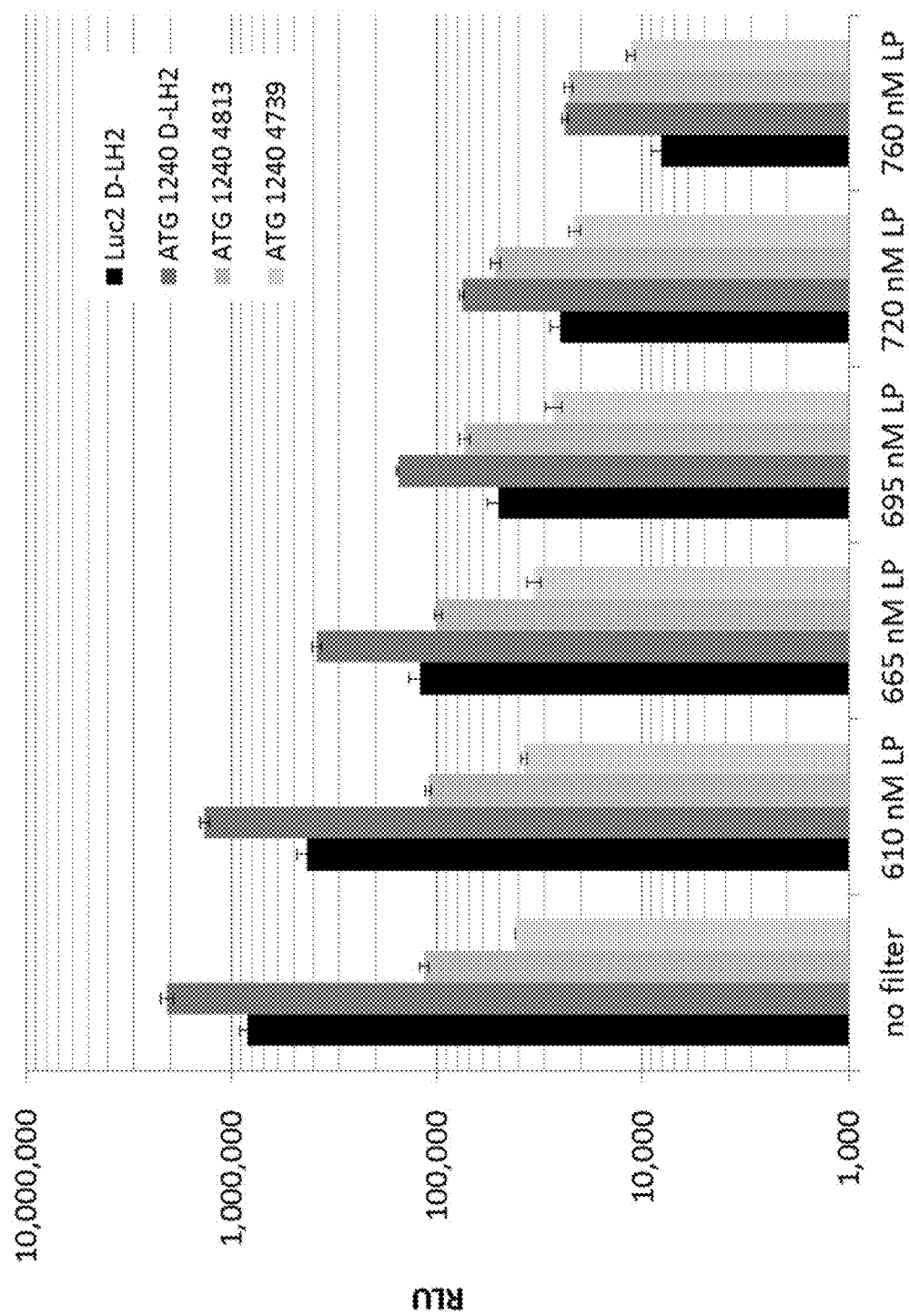
FIG. 17 illustrates the luminescence measured using long pass filters to mimic tissue attenuation of CBR variant ATG 1240 using luciferin ("D-LH2"; medium dark bars), PBI-4813 (medium light bars), and PBI-4739 (light bars) as substrates compared with firefly luciferase ("Luc2") using luciferin (dark bars).
Figure 20A:
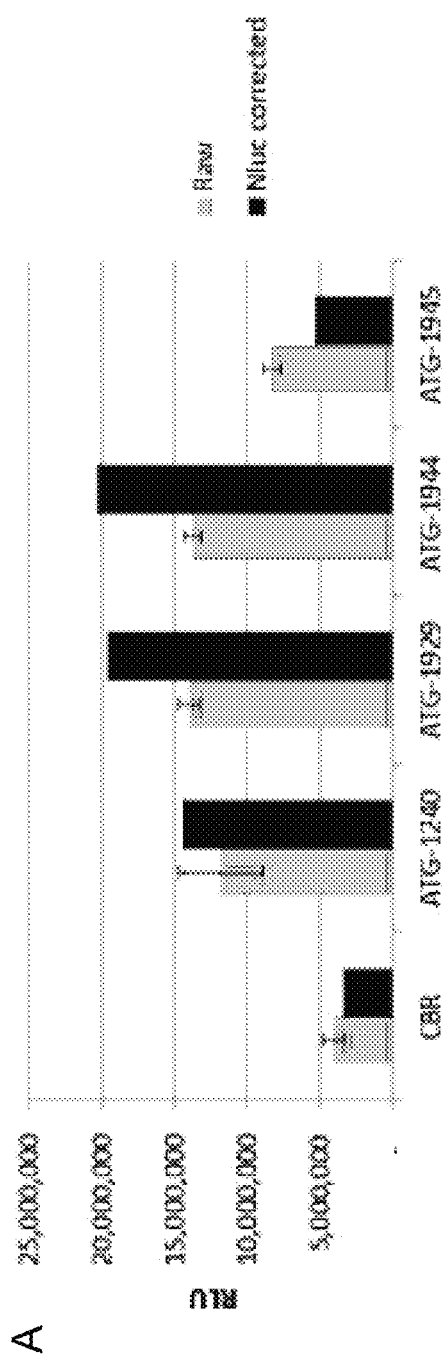
FIG. 20A and FIG. 20B illustrate the luminescence of codon optimized CBR variants expressed in CHO cells (FIG. 20A) or 3T3 cells (FIG. 20B) using Bright-Glo™ assay buffer.
Figure 20B:
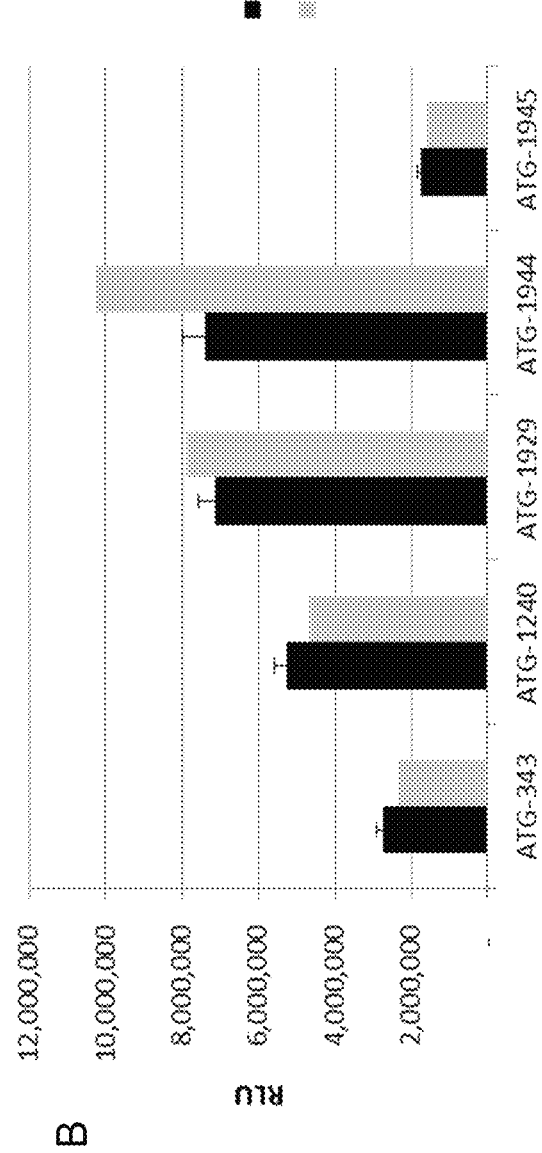

These results in FIG. 17 suggest that ATG 1240 assayed with D-luciferin may be brighter than with PBI-4739 even when light is attenuated with long pass filters. PBI-4813 and D-luciferin are comparable at the greatest light attenuation. Note that the Km for PBI-4813 was more than 10 times less than for D-luciferin in live cell. This could be an advantage for PBI-4813 in live animals.

Example 14

Codon Optimization 600,000 cells (HEK293, 3T3, or CHO cells) in 3 mL were plated in 6 well plates. Briefly, for each cell type grown in t-75 flasks, media was removed from the t-75 flask and the cells were washed with DPBS. 3 mL of Trypsin was added to the cells and the cells were incubated for 3 min. 10 mL of growth media (DMEM+10% FBS for HEK293T and 3T3, Ham F12+10% FBS for CHO) were added. Cells were centrifuged at 500 rpm for 5 min. The cells were counted and diluted to 200,000 per mL. 3 mL of cells were added to each well of a six well plate (i.e., 600,000 cells).

Protocol for transfection of HEK293 cells grown in 3,000 µL of medium in 6-well plates using a FuGENE® HD:DNA ratio of 3.0:1. This protocol will prepare sufficient DNA/FuGENE® HD reagent to transfect 3 wells at 3000 µL/well.

Cell plating. HEK293 cells were plated the day before transfection at a density of $5 \times 10^5$ cells per well of a 6-well plate in 3 ml of complete growth medium (DMEM+10% Fetal Bovine Serum).

Complex preparation. 465 µL of 0.020 µg/µL plasmid solution were prepared in OptiMEM, OptiPro, or sterile deionized water. Briefly, 9.9 µg of test DNA was added in 465 µl total volume. 10 ng of Nanoluc DNA was added to each reaction ("ATG42") for normalization. 30 µl of FuGENE® HD reagent was added and mixed carefully by pipetting (15 times) or by vortexing briefly. The mixture incubated for 5 to 10 min at room temperature. 150 µl of complex was added per well to the cells, and mixed thoroughly. The Reagent:DNA ratio may range from 2.5:1.0 to 3.5:1.0. The recommended Reagent:DNA ratio for HEK293 cells was 3.0:1 at 3.0 µg DNA per well.

Re-plate cells: Growth media was removed and the cells were washed with 1 ml of DPBS. 3 ml of growth media was added and the cells were centrifuged at 500 rpm. For each sample, the pellets were re-suspended in 1 ml of media and the cells were counted. The HEK cells had very little pellet and the cell counts were below 100,000/ml. See Table 9 for dilution of 3T3 and CHO cells. 100 µL of each sample (n=16) were plated in a 96 well plate. One plate was used for each cell type.

TABLE 9

| Construct | Cells/mL * 10E6 | Volume cells (µL) | Volume media (mL) |
|---|---|---|---|
| 3T3 | | | |
| ATG 343 | 1.4 | 286 | 1.7 |
| ATG 1240 | 1.2 | 333 | 1.7 |
| ATG 1929 | 1.5 | 267 | 1.7 |
| ATG 1944 | 1.1 | 364 | 1.6 |
| ATG 1945 | 1.7 | 235 | 1.8 |
| CHO | | | |
| ATG 343 | 1.3 | 308 | 1.7 |
| ATG 1240 | 0.8 | 500 | 1.5 |
| ATG 1929 | 0.6 | 667 | 1.3 |
| ATG 1944 | 0.72 | 556 | 1.4 |
| ATG 1945 | 0.75 | 533 | 1.5 |

Assay: Bright-Glo assay buffer was reconstituted with Bright-Glo assay substrate. 500 µL of furimazine was added to 25 ml of NanoGlo Assay buffer. 100 µL of reconstituted Bright-Glo was added to each sample (n=8) and 100 µL of NanoGlo was added to the other samples (n=8) and read on GloMax®-Multi+.

Legend/background information for codon optimization experiments:

Variant 343=CBR sequence ("ATG 343")
Variant 1240=CBR sequence+R334S/G351R ("ATG 1240")
Variant 1929=CBR sequence+R334S/G351R (codon optimized for RNA structure and codon usage in rodents) ("ATG 1929")
Variant 1944=CBR sequence+R334S/G351R (codon optimized for RNA structure and codon usage in CHO cells) ("ATG 1944")

Variant 1945=CBR sequence+R334S/G351R (codon optimized for RNA structure and codon usage in mouse lung and liver cells) ("ATG 1945")

While the present invention is described in connection with what is presently considered to be the most practical and preferred embodiments, it should be appreciated that the invention is not limited to the disclosed embodiments, and is intended to cover various modifications and equivalent arrangements included within the spirit and scope of the claims. Modifications and variations in the present invention may be made without departing from the novel aspects of the invention as defined in the claims. The appended claims should be construed broadly and in a manner consistent with the spirit and the scope of the invention herein.

For reasons of completeness, various aspects of the invention are set out in the following numbered clauses:

Clause 1. An isolated polynucleotide encoding a click beetle red luciferase (CBR) variant polypeptide having at least 80% amino acid sequence identity to SEQ ID NO: 1 and comprising at least one amino acid substitution at a position corresponding to position 4, 16, 34, 47, 51, 52, 55, 72, 73, 74, 79, 82, 83, 87, 89, 104, 109, 113, 117, 119, 124, 130, 131, 133, 136, 144, 146, 156, 159, 170, 179, 186, 200, 211, 218, 224, 225, 226, 228, 229, 234, 247, 251, 252, 253, 255, 280, 281, 285, 308, 309, 310, 319, 329, 334, 335, 337, 346, 348, 349, 350, 352, 354, 355, 358, 363, 370, 377, 390, 393, 394, 400, 401, 409, 412, 420, 422, 431, 437, 439, 444, 445, 453, 455, 467, 471, 473, 479, 484, 489, 496, 501, 503, 508, 516, 528, 531, 535, 537, 539, or combination thereof, of SEQ ID NO: 1, wherein the variant CBR polypeptide has at least one of enhanced luminescence, altered light emission wavelength, altered substrate specificity, or a combination thereof, as compared to a CBR polypeptide of SEQ ID NO: 1.

Clause 2. The isolated polynucleotide of clause 1, wherein the CBR variant polypeptide further comprises at least one amino acid substitution at a position corresponding to position 351, 389, 457, or combination thereof, of SEQ ID NO: 1.

Clause 3. The isolated polynucleotide of clause 1 or 2, wherein the CBR variant polypeptide comprises a substitution corresponding to at least one of R4H, H16Q, H34Y, D47E, S51N, Y52C, F55L/V, K72E, I79V, M73K/T, N74S, E82G, N83H, F87S, I89V, V104D, I109N/V, L113Q, M117T, I119F/T, I124V, N130K, I131N/T, N133D, K136N, F144L, K146E, N156D, N156K, G159D, Y170C, K179S, V186A, G200G, N211N, H218L/Y, G225S, T226C/G/H/N/Q/Y, L228P, I229V, V234A, G251S, G251I, Y252C, V255D/F, E253K, R280S, S281N/Q, V285A, I309T, E319G, N329D, R334E/Q/H/S/N/K, C335S, K337E, I346N, Q348H/E, L350P, G351K/R, D352N, R355G, S358P, T363A/S, I370T, I389F/G/S/V, I390I, M393K/L, V394M, N400D, N401S, I409T, D412G, F420F, Y422C, V431A, E437G, I439V, S444C/R/T, Q445H, E453K, V455D, K457N, D471V, E473A, S479T, K484E/M/R, E489V, Y496H, E501G, V503M, Y508C, V516A, T528A, E531G, Q535H, L537W, K539R, or combinations thereof, or SEQ ID NO: 1.

Clause 4. The isolated polynucleotide of any one of clauses 1-3, wherein the CBR variant polypeptide comprises an amino acid substitution at a position corresponding to position 389, 444, and 251 of SEQ ID NO: 1.

Clause 5. The isolated polynucleotide of any one of clauses 1-4, wherein the amino acid substitutions comprise I389F, S444R, and G251S.

Clause 6. The isolated polynucleotide of any one of clauses 1-5, wherein the CBR variant polypeptide comprises an amino acid substitution at positions corresponding to positions 334 and 351 of SEQ ID NO: 1.

Clause 7. The isolated polynucleotide of any one of clauses 1-6, wherein the amino acid substitutions comprise R334S and G351R.

Clause 8. The isolated polynucleotide of any one of clauses 1-7, wherein the CBR variant polypeptide further comprises an amino acid substitution at a position corresponding to positions 51 and 444 of SEQ ID NO: 1.

Clause 9. The isolated polynucleotide of any one of clauses 1-8, wherein the amino acid substitutions comprise S51N and S444R.

Clause 10. The isolated polynucleotide of clause 1, wherein the CBR variant polypeptide comprises an amino acid polypeptide of SEQ ID NO: 2, SEQ ID NO: 3, or SEQ ID NO: 4.

Clause 11. The isolated polynucleotide of any one of the preceding clauses, wherein the CBR variant polypeptide has enhanced luminescence compared to a CBR polypeptide of SEQ ID NO: 1.

Clause 12. The isolated polynucleotide of clause 11, wherein the CBR variant polypeptide has enhanced luminescence when a luciferin is utilized by the CBR variant polypeptide to generate luminescence.

Clause 13. The isolated polynucleotide of clause 11, wherein the CBR variant polypeptide has enhanced luminescence when a luciferin derivative is utilized by the CBR variant polypeptide to generate luminescence.

Clause 14. The isolated polynucleotide of clause 13, wherein the luciferin derivative comprises:

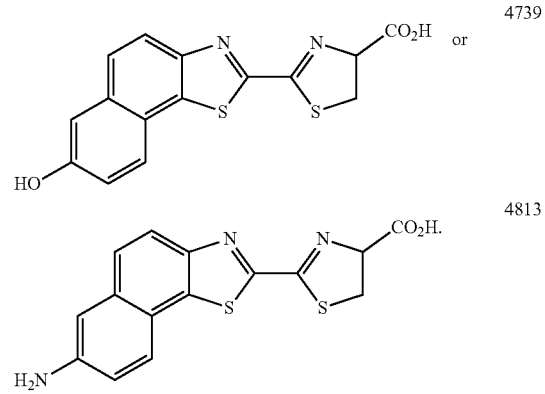

Clause 15. The isolated polynucleotide of clause 14, wherein the CBR variant polypeptide has at least 2 fold increase in luminescence compared to a CBR polypeptide of SEQ ID NO: 1.

Clause 16. The isolated polynucleotide of clause 14, wherein the CBR variant polypeptide has at least 4 fold increase in luminescence compared to a CBR polypeptide of SEQ ID NO: 1.

Clause 17. The isolated polynucleotide of any one of the preceding clauses, wherein the CBR variant polypeptide has altered light emission spectra compared to a CBR polypeptide of SEQ ID NO: 1.

Clause 18. The isolated polynucleotide of clause 17, wherein the CBR variant polypeptide is able to emit light at a longer wavelength when a luciferin is utilized by the CBR variant polypeptide to generate luminescence.

Clause 19. The isolated polynucleotide of clause 17, wherein the CBR variant polypeptide is able to emit light at a longer wavelength when a luciferin derivative is utilized by the CBR variant polypeptide to generate luminescence.

Clause 20. The isolated polynucleotide of clause 19, wherein the luciferin derivative comprises:

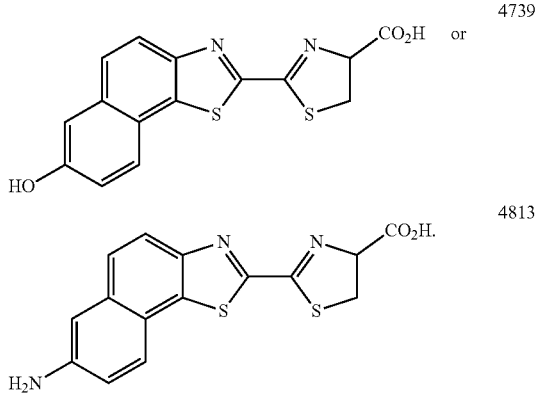

4739

4813

Clause 21. The isolated polynucleotide of clause 20, wherein if the luciferin derivative comprises

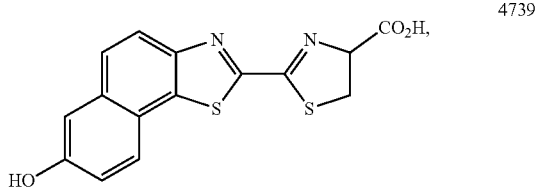 [SMILES: O=C(O)C1CSC(c2nc3ccc4cc(O)ccc4c3s2)=N1]

4739 the CBR variant polypeptide emits light having a shift in spectral maximum of at least about 1 nm to at least about 100 nm relative to the light produced by the CBR polypeptide of SEQ ID NO: 1.

Clause 22. The isolated polynucleotide of clause 21, wherein the CBR variant polypeptide emits light having a spectral maximum between about 650 nm to about 800 nm.

Clause 23. The isolated polynucleotide of clause 21, wherein the CBR variant polypeptide emits light having a spectral maximum between about 725 nm to about 775 nm.

Clause 24. The isolated polynucleotide of clause 21, wherein the CBR variant polypeptide emits light having a spectral maximum of about 750 nm.

Clause 25. The isolated polynucleotide of clause 20, wherein if the luciferin derivative comprises

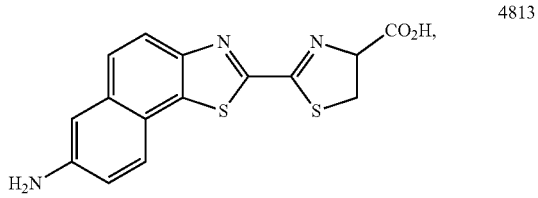 [SMILES: Nc1ccc2c(ccc3nc(C4=NC(C(=O)O)CS4)sc32)c1]

4813 the CBR variant polypeptide emits light having a shift in spectral maximum of at least about 1 nm to at least about 100 nm relative to the light produced by the CBR polypeptide of SEQ ID NO: 1.

Clause 26. The isolated polynucleotide of clause 25, wherein the CBR variant polypeptide emits light having a shift in spectral maximum of at least about 75 nm relative to the light produced by the CBR polypeptide of SEQ ID NO: 1.

Clause 27. The isolated polynucleotide of clause 25, wherein the CBR variant polypeptide emits light having a spectral maximum between about 650 nm to about 800 nm.

Clause 28. The isolated polynucleotide of clause 25, wherein the CBR variant polypeptide emits light having a spectral maximum between about 700 nm to about 775 nm.

Clause 29. The isolated polynucleotide of clause 25, wherein the CBR variant polypeptide emits light having a spectral maximum of about 725 nm.

Clause 30. The isolated polynucleotide any one of the preceding clauses, wherein the CBR variant polypeptide has altered substrate specificity compared to a CBR polypeptide of SEQ ID NO: 1.

Clause 31. The isolated polynucleotide of clause 30, wherein the CBR variant polypeptide has a change in relative specificity relative to the CBR variant polypeptide in the presence of a luciferin compared to a luciferin derivative.

Clause 32. The isolated polynucleotide of clause 30, wherein the CBR variant polypeptide has a change in relative specificity relative to the CBR variant polypeptide in the presence of a luciferin derivative compared to a different luciferin derivative.

Clause 33. The isolated polynucleotide of clause 31 or 32, wherein the luciferin derivative comprises:

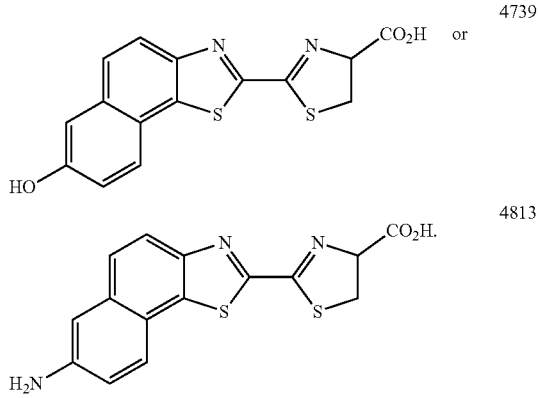

4739

4813

Clause 34. The isolated polynucleotide of any one of the preceding clauses, wherein the variant CBR polypeptide has luciferase activity.

Clause 35. The isolated polynucleotide of any one of the preceding clauses, wherein the variant CBR polypeptide has a Km for PBI-4813 of at least about 0.01 μM to at least about 5.00 μM.

Clause 36. The isolated polynucleotide of clause 35, wherein the variant CBR polypeptide has a Km for PBI-4813 of at least about 0.50 μM to at least about 3.00 μM.

Clause 37. The isolated polynucleotide of clause 35, wherein the variant CBR polypeptide has a Km for PBI-4813 of at least about 0.82 μM or 2.41 μM.

Clause 38. The isolated polynucleotide of any one of the preceding clauses, wherein the variant CBR polypeptide has a Km for PBI-4739 of at least about 0.01 μM to at least about 5.00 μM.

Clause 39. The isolated polynucleotide of clause 38, wherein the variant CBR polypeptide has a Km for PBI-4739 of at least about 1.50 μM to at least about 4.50 μM.

Clause 40. The isolated polynucleotide of clause 38, wherein the variant CBR polypeptide has a Km for PBI-4739 of at least about 2.33 µM or 3.95 µM.

Clause 41. The isolated polynucleotide of any one of the preceding clauses, wherein the variant CBR polypeptide has a relative Vmax that is at least 2 fold higher than the relative Vmax of a CBR polypeptide of SEQ ID NO: 1 using PBI-4813 as a substrate.

Clause 42. The isolated polynucleotide of any one of the preceding clauses, wherein the variant CBR polypeptide has a relative Vmax that is at least 2 fold higher than the relative Vmax of a CBR polypeptide of SEQ ID NO: 1 using PBI-4739 as a substrate.

Clause 43. The isolated polynucleotide of any one of the preceding clauses, wherein the sequence has been codon-optimized.

Clause 44. The isolated polynucleotide of any one of the preceding clauses, wherein the sequence comprises a polynucleotide of SEQ ID NOs: 6-9.

Clause 45. The isolated polynucleotide of any one of the preceding clauses, wherein the polynucleotide further encodes a polypeptide of interest linked to the CBR variant polypeptide, the polypeptide of interest and the CBR variant polypeptide capable of being expressed as a fusion protein.

Clause 46. The isolated polynucleotide of clause 45, wherein the polypeptide of interest comprises HALOTAG®.

Clause 47. A vector comprising the polynucleotide, or a fragment thereof, of any one of the preceding clauses.

Clause 48. The vector of clause 47, wherein the polynucleotide is operably linked to a promoter.

Clause 49. A cell comprising the polynucleotide of any one of clauses 1-46 or the vector of clause 47 or 48.

Clause 50. A non-human transgenic animal comprising the cell of clause 49.

Clause 51. A non-human transgenic animal comprising the polynucleotide of any one of clauses 1-46 or the vector of clause 47 or 48.

Clause 52. A CBR variant polypeptide encoded by the polynucleotide of any one clauses 1-46.

Clause 53. A circularly permuted luciferase comprising the polypeptide encoded by the polynucleotide of any one of clauses 1-46 or a fragment thereof.

Clause 54. A fusion protein comprising a CBR variant polypeptide encoded by the polynucleotide of any one of clauses 1-46.

Clause 55. A near-infrared bioluminescence system comprising the polynucleotide of any one of clauses 1-46 and a luciferin derivative.

Clause 56. The near-infrared bioluminescence system of clause 55, wherein the luciferin derivative comprises:

Clause 57. A method of producing a CBR variant polypeptide comprising growing the cell of clause 47 under conditions that permit expression of the CBR variant polypeptide.

Clause 58. A method of producing a CBR variant polypeptide comprising introducing the vector of clause 47 or 48 into a cell under conditions which permit expression of the CBR variant polypeptide.

Clause 59. A kit comprising the polynucleotide of any one of clauses 1-46 or the vector of clause 47 or 48.

Clause 60. A kit comprising the CBR variant polypeptide of clause 46.

Clause 61. The kit of clause 59 or 60 further comprising at least one of:

(a)

and (b) a buffer reagent.

Clause 62. A bioluminescence resonance energy transfer (BRET) system comprising: a first fusion protein including a first target protein and a bioluminescence donor molecule, wherein the bioluminescence donor molecule is a CBR variant encoded by the polynucleotide of any one of clauses 1-46; a second fusion protein including a second target protein and a fluorescent acceptor molecule; and a CBR substrate.

Clause 63. The BRET system of clause 62, wherein the CBR substrate is a luciferin or luciferin derivative.

Clause 64. The BRET system of clause 63, wherein the luciferin derivative comprises:

Clause 65. A method for measuring bioluminescence using at least one of the polynucleotide of any one of clauses 1-46; the vector of any one of clauses 47 or 48; the cell of clause 49; the animal of any of clauses 50 or 51; the CBR variant polypeptide of clause 52; the circularly permuted luciferase of clause 53; the fusion protein of clause 54, or the near-infrared bioluminescence system of clause 55 or 56.

Clause 66. The method of clause 65, wherein the bioluminescence is measured in a live, intact non-human animal.

Clause 67. A method of measuring the enzymatic activity of a luminogenic protein, the method comprising: contacting a luminogenic protein, a deprotecting enzyme, and a protected luminophore; and detecting light produced from the composition, wherein the luminogenic protein is a CBR variant encoded by the polynucleotide of any one of clauses 1-46 and the luminophore is a luciferin derivative comprising:

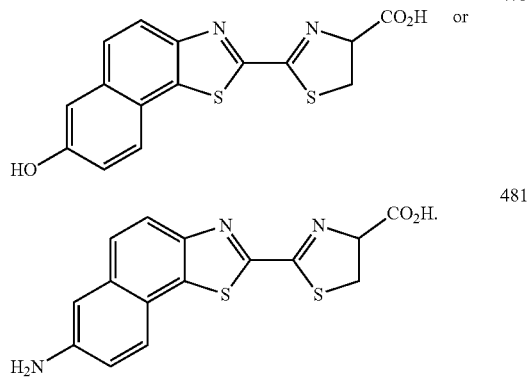

Clause 68. The method of clause 67, wherein the enzymatic activity is measured in a live, intact non-human animal.

Clause 69. A method for measuring the activity of a non-luminescent enzyme of interest, the method comprising: (a) providing a luminogenic molecule wherein the molecule is a substrate for the non-luminescent enzyme of interest and a pro-substrate of a CBR variant encoded by the polynucleotide of any one of clauses 1-46; (b) contacting the luminogenic molecule with at least one non-luminescent enzyme of interest and at least one CBR variant to produce a reaction mixture; and (c) determining activity of the non-luminescent enzyme of interest by measuring luminescence of the reaction mixture.

Clause 70. The method of clause 69, wherein the luminogenic molecule is a modification of

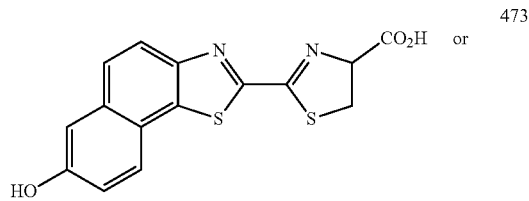

-continued

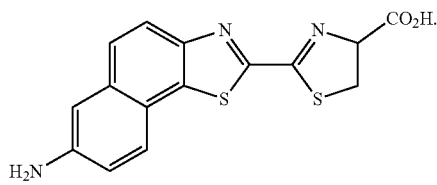

Clause 71. The method of any one of clauses 69 and 70 wherein the non-luminescent enzyme of interest is a protease enzyme, a cytochrome P450 enzyme, a monoamine oxidase enzyme, or a glutathione S-transferase enzyme.

Clause 72. The method of any one of clauses 69 to 71 wherein the activity of the non-luminescent enzyme is measured in a live, intact animal.

Clause 73. A method to detect the presence of at least two molecules in a sample or a cell, the method comprising: contacting the sample or cell with a first reporter molecule comprising a CBR variant encoded by the polynucleotide of any one of clauses 1-46, wherein the first reporter molecule is operatively linked to a first component of the sample or cell; contacting the sample with a second reporter molecule, wherein the second reporter molecule is operatively linked to a second component of the sample or cell; and detecting the presence of the first and second reporter molecules to determine the presence and/or amounts of the first and second components in the sample or cell.

Clause 74. A method to detect an interaction between a first protein and a second protein in a sample, the method comprising:
(a) contacting a sample with:

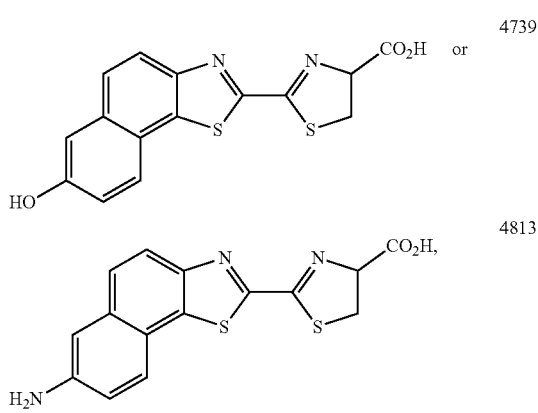

wherein the sample comprises:
(i) a first polynucleotide encoding a first fusion protein, wherein the first fusion protein comprises a first fragment of a luminescent enzyme and a first protein; and
(ii) a second polynucleotide encoding a second fusion protein, wherein the second fusion protein comprises a second fragment of the luminescent enzyme and a second protein; and
(b) detecting luminescence in the sample,
wherein the detection of luminescence indicates an interaction between the first protein and the second protein, wherein the luminescent enzyme is encoded by the isolated polynucleotide of any one of clauses 1-46.

Clause 75. The method of clause 74, wherein when the first protein and second protein interact, the first fragment of the luminescent enzyme and the second fragment of the luminescent enzyme reconstitute a full-length enzyme capable of stably binding the cell-permeable substrate.

Clause 76. A method to detect an interaction between a first protein and a second protein in a sample, the method comprising:
(a) contacting a sample with:

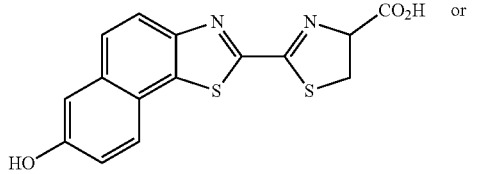

4739 or

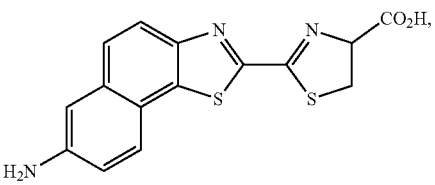

4813 wherein the sample comprises:
(i) a first polynucleotide encoding a first fusion protein, wherein the first fusion protein comprises a luminescent enzyme and a first protein, wherein the luminescent enzyme is encoded by the isolated polynucleotide of any one of clauses 1-46; and
(ii) a second polynucleotide encoding a second fusion protein, wherein the second fusion protein comprises a fluorescent acceptor molecule and a second protein; and
(b) detecting bioluminescence resonance energy transfer (BRET) in the sample, indicating an interaction or close proximity of the bioluminescent donor and the fluorescence acceptor.

We claim:

1. A method of measuring activity of a non-luminescent enzyme-of-interest, the method comprising:
   combining a luminogenic protein, a non-luminescent enzyme-of-interest, and a luminogenic molecule into a composition, wherein the luminogenic molecule is a pro-substrate for the luminogenic protein and a substrate for the non-luminescent enzyme-of-interest, and wherein the non-luminescent enzyme-of-interest is selected from a reductase, a glycosidase, a protease, an oxidase, a beta-lactamase, and a glutathione transferase; and
   determining activity of the non-luminescent enzyme-of-interest by detecting light produced from the composition, wherein the luminogenic protein is a click beetle red luciferase (CBR) variant having at least 80% amino acid sequence identity to SEQ ID NO: 1 and comprises at least one amino acid substitution at a position corresponding to position 4, 16, 34, 47, 51, 52, 55, 72, 73, 74, 79, 82, 83, 87, 89, 104, 109, 113, 117, 119, 124, 130, 131, 133, 136, 144, 146, 156, 159, 170, 179, 186, 200, 211, 218, 224, 225, 226, 228, 229, 234, 247, 251, 252, 253, 255, 280, 281, 285, 308, 309, 310, 319, 329, 334, 335, 337, 346, 348, 349, 350, 352, 354, 355, 358, 363, 370, 377, 390, 393, 394, 400, 401, 409, 412, 420, 422, 431, 437, 439, 444, 445, 453, 455, 467, 471, 473, 479, 484, 489, 496, 501, 503, 508, 516, 528, 531, 535, 537, 539, or combination thereof, of SEQ ID NO: 1, and wherein the variant click beetle red luciferase (CBR) polypeptide has at least one of enhanced luminescence, altered light emission wavelength, altered substrate specificity, or a combination thereof, as compared to a click beetle red luciferase (CBR) polypeptide of SEQ ID NO: 1.

2. The method of claim 1, wherein the pro-substrate for the luminogenic protein comprises one of the following luciferin derivatives:

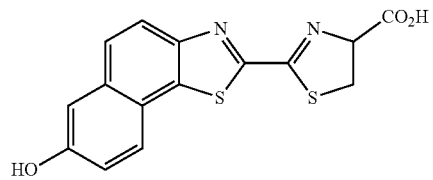

4739

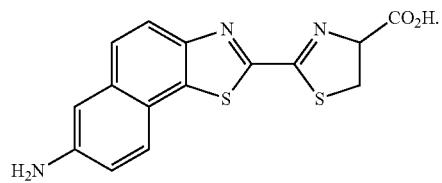

4813

3. The method of claim 1, wherein the CBR variant polypeptide comprises an amino acid substitution at a position corresponding to positions 251 and 444, and further comprising an amino acid substitution at position 389 of SEQ ID NO: 1.

4. The method of claim 3, wherein the CBR variant polypeptide further comprises an amino acid substitution at position 51 of SEQ ID NO: 1.

5. The method of claim 1, wherein the CBR variant polypeptide comprises an amino acid substitution at a position corresponding to positions 334 and further comprising an amino acid substitution at position 351 of SEQ ID NO: 1.

6. The method of claim 5, wherein the CBR variant polypeptide further comprises an amino acid substitution at a position corresponding to positions 51 and 444 of SEQ ID NO: 1.

7. The method of claim 1, wherein the CBR variant polypeptide comprises a polypeptide sequence of SEQ ID NO: 2, SEQ ID NO: 3, or SEQ ID NO: 4.

* * * * *